(12) United States Patent
Lerner et al.

(10) Patent No.: US 7,189,841 B2
(45) Date of Patent: Mar. 13, 2007

(54) METHOD FOR TAPPING THE IMMUNOLOGICAL REPERTOIRE

(75) Inventors: Richard A. Lerner, La Jolla, CA (US); Joseph A. Sorge, Wilson, WY (US); Gregory P. Winter, Cambridge (GB); Lutz Riechmann, Cambridge (GB)

(73) Assignees: Scripps Research Institute, La Jolla, CA (US); Medical Research Council, London (GB); Stratagene, La Jolla, CA (US)

( * ) Notice: Subject to any disclaimer, the term of this patent is extended or adjusted under 35 U.S.C. 154(b) by 86 days.

(21) Appl. No.: 10/910,463

(22) Filed: Aug. 2, 2004

(65) Prior Publication Data

US 2006/0019260 A1 Jan. 26, 2006

Related U.S. Application Data

(60) Division of application No. 09/726,649, filed on Nov. 28, 2000, now Pat. No. 6,969,586, which is a division of application No. 07/941,762, filed on Sep. 4, 1992, now Pat. No. 6,291,161, which is a continuation of application No. 07/809,083, filed on Dec. 9, 1991, now abandoned, which is a continuation of application No. 07/446,332, filed on Dec. 4, 1989, now abandoned, which is a continuation-in-part of application No. 07/353,241, filed on May 17, 1989, now abandoned, and a continuation-in-part of application No. 07/353,235, filed on May 16, 1989, now abandoned.

(51) Int. Cl.
*C07H 21/04* (2006.01)

(52) U.S. Cl. .................... 536/24.33; 435/91.2

(58) Field of Classification Search .............. None
See application file for complete search history.

(56) References Cited

U.S. PATENT DOCUMENTS

| 4,356,270 A | 10/1982 | Itakura |
| 4,642,334 A | 2/1987 | Moore et al. |
| 4,656,134 A | 4/1987 | Ringold |
| 4,659,567 A | 4/1987 | Tramontano et al. |
| 4,683,195 A | 7/1987 | Mullis et al. |
| 4,683,202 A | 7/1987 | Mullis |
| 4,704,692 A | 11/1987 | Landner et al. |
| 4,711,845 A | 12/1987 | Gelfand et al. |
| 4,714,681 A | 12/1987 | Reading |
| 4,800,159 A | 1/1989 | Mullis et al. |
| 4,806,471 A | 2/1989 | Molin et al. |
| 4,816,397 A | 3/1989 | Boss et al. |
| 4,889,818 A | 12/1989 | Gelfand et al. |
| 4,937,193 A | 6/1990 | Hinchliffe et al. |
| 4,946,786 A | 8/1990 | Tabor et al. |
| 4,959,317 A | 9/1990 | Sauer |
| 4,965,188 A | 10/1990 | Mullis et al. |
| 4,978,743 A | 12/1990 | Selbeck et al. |
| 4,983,728 A | 1/1991 | Herzog et al. |
| 5,023,171 A | 6/1991 | Ho et al. |
| 5,126,258 A | 6/1992 | Lerner |
| 5,229,272 A | 7/1993 | Paul |
| 6,331,415 B1 | 12/2001 | Cabilly et al. |

FOREIGN PATENT DOCUMENTS

| EP | 012523 | 4/1984 |
| EP | 0125023 | 11/1984 |
| EP | 0171496 | 2/1986 |
| EP | 0200 362 A2 | 3/1986 |
| EP | 0173494 | 3/1986 |
| EP | 0201184 | 11/1986 |
| EP | 0239400 | 9/1987 |
| EP | 0120694 | 7/1993 |
| EP | 0194276 | 8/1993 |
| EP | 0368684 | 3/1994 |
| EP | 0239400 | 8/1994 |
| GB | 2137631 | 10/1984 |
| JP | 61-104788 | 5/1986 |
| JP | 63-152984 | 6/1988 |
| WO | WO 88/01649 | 3/1988 |
| WO | WO 88/06630 | 9/1988 |
| WO | WO-A-8806630 | 9/1988 |
| WO | WO 88/09344 | 12/1988 |
| WO | WO-A-8809344 | 12/1988 |
| WO | WO 89/00999 | 2/1989 |
| WO | WO 89/01526 | 2/1989 |
| WO | WO-A-8901526 | 2/1989 |
| WO | WO 90/14424 | 11/1990 |
| WO | WO 90/14430 | 11/1990 |
| WO | WO 90/14443 | 11/1990 |
| WO | WO 97/08320 | 3/1997 |

OTHER PUBLICATIONS

Hartman et al., The EMBO Journal, vol. 3, No. 12, 1984, pp. 3023-3030.*

(Continued)

*Primary Examiner*—James Ketter
(74) *Attorney, Agent, or Firm*—Howrey LLP

(57) ABSTRACT

The present invention relates to a method for isolating from the immunological gene repertoire a gene coding for a receptor having the ability to bind a preselected ligand. Receptors produced by the gene isolated by the method, particularly catalytic receptors, are also contemplated.

5 Claims, 26 Drawing Sheets

OTHER PUBLICATIONS

Short et al NAR 16: 7582. 1988.
Jonda et al Science 241: 1188. 1988.
Pollach et al Science 234: 1570. 1986.
Tramantano et al Science 234: 1566. 1986.
Short et al NAR 16(15): 7583, 1988.
Lavich et al Bus RC 160(3): 1250, 1989.
Shem et al Science 240: 1038, 1988.
Sastry, L. et al., "Cloning of the immunological repertoire in *Escherichis coli* for generation of monoclonal catalytic antibodies: Construction of a heavy chain variable region-specific cDNA library", Proc. Natl. Acad. Sci., USA, vol. 86: Aug. 1989 pp. 5728-5732.
Orlandi, R., et al., "Cloning immunoglobulin variable domains for expression by the polymerase chain reaction", Proc. Natl. Acad. Sci., USA, vol. 10:May 15, 1989, pp. 3833-3837.
Larrick, J.W. et al., "Rapid cloning of rearranged Immunoglobulin genes from human hybridoma cells using mixed primers and the polymerase chain reaction", Biochem. & Bioph. Res. Comm., vol. 3:, May 15, 1989, pp. 1250-1256.
Huse, W.D., "Generation of a large combinatorial library of the Immunoglobulin repertoire in Phage lambda", Science, vol. 246, Dec. 8, 1989, pp. 1275-1281.
Aviv and Leder, "Purification of Biologically Active Globin Messenger RNA by by Chromatography on Oligothymidylic acid-Cellulose", Proc. Nat. Acad. Sci. USA 69: 1408-1412 (1972).
Berent, et al., "Comparison of Oligonucleotide and Long DNA Fragments as Probes in DNA and RNA Dot, Southern, Northern, Colony and Plaque Hybridizations", BioTechniques 3: 208-220 (1985).
Better, et al., "*Escherichia coli* Secretion of an Active Chimeric Antibody Fragment", Science 240: 1041-1043 (1988).
Bird, et al., "Single-Chain Antigen-Binding Proteins", Science 242:423-426 (1988).
Bolton, et al., "The Labelling of Proteins to High Specific Radioactivity by Conjugation to a .sup.125 I-Containing Acylating Agent", Biochem. 133: 529-539 (1973).
Broudeur, and Riblet, "The immunoglobulin heavy chain variable . . . ", Eur. J. Immunol. 14: 922-930 (1984).
Brown, et al., "Chemical Synthesis and Cloning of a Tyrosine tRNA Gene", Methods in Enzymol. 68: 109-151 (1979).
Chang, et al., "Cloning and expression of recombinant, functional ricin B chain", PNAS 84: 5640-5644 (1987).
Chomczynski, Sacchi, "Single Step Method of RNA Isolation by Acid Goanidinium Thiocyanate-Phenol-Chloroform Extraction", Anal. Biochem. 162: 156-159 (1987).
Cohen, et al., "Nonchromosomal Antibiotic Resistance in Bacteria: Genetic Transformation of *Escherichia coli* by R-Factor DNA", Proc. Nat. Acad. Sci. USA 69: 2110-2114 (1972).
Delaloye, et al., "Detection of Colorectal Carcinoma by Emission-computerized Tomography", Clin. Inv. 77:301-311 (1986).
Dildrop and Renate, "A new classification of mouse V.sub.H sequences", Immunology Today 5: 85-86 (1984).
DiLella, et al., "Cloning range Segments of Genomic DNA Using Cosmid Vectors", Methods in Enzymol. 152: 199-212 (1987).
Field, et al., "Purification of a RAS-Responsive Adenylyl Cyclase Complex from Saccharomyces cerevisiae by Use of an Epitope Addition Method", Molecular Cell Biology 8: 2159-2165 (1988).
Frischauf, et al., "Construction and Characterization of a Genomic Library", Methods in Enzymol. 152: 190-199 (1987).
Frischauf, et al., "Digestion of DNA: Size Fractionation", Methods in Enzymol. 152: 183-189 (1987).
Garrett, et al., "Lethal Action of Bacteriophage .lambda. S Gene", J. Virology 44: 886-892 (1982).
Gearheart, et al., "IgG antibodies to phosphorylcholine exhibit more diversity than their IgM counterparts" Nature 291: 29-34 (1981).
Ginsberg, et al., "Immunochemical and Amino-terminal Sequence Comparison of Two Cytoadhesins Indicates They Contain Similar or Identical .beta. Subunits and Distinct .alpha. subunits", J. Biol. Chem. 262: 5437-5440 (1987).
Gold, et al., "Translational Initiation in Prokaryotes", Ann. Rev. Microbiol. 35: 365-403 (1981).

Graham, et al., "A New Technique for the Assay of Infectivity of Human Adenovirus 5 DNA", Virology 52: 456-467 (1973).
Green, et al., "Immunogenic Structure of the Influenze Virus Hemagglutinin", Cell 28: 477-487 (1982).
Guarente, et al., "Improved Methods for Maximizing Expression of a Cloned Gene: a Bacterium That Synthesizes Rabbit .beta.-Globin", Cell 20: 543-553 (1980).
Guarente, et al., "A technique for Expression Eukaryotic Genes in Bacteria", Science 209: 1428-1430 (1980).
Gussow, et al. "Generating Binding Activities from *Escherichia coli* by Expression of a Repertoire of Immunoglobulin Variable Domains", Cold Spring Harbor Symposia on Quantitative Biology vol. LIV, Cold Spring Harbor Laboratory Press (1989).
Edgar Haber, In vivo Diagnostic and Therapeutic Uses of Monoclonal Antibodies In Cardiology, Ann. Review Med. 37: 249-261 (1986).
Herrmann, and Frischauf "Isolation of Genomic DNA", Methods in Enzymol 152: 180-183 (1987).
Holmes, and Quigley, A Rapid Boiling Method for the Preparation of Bacterial Plasmids Anal. Biochem. 114: 193-197 (1981).
Huse, et al., "Generation of a Large Combinatorial Library of the Immunoglobulin Repertoire in Phage Lambda" Science 246: 1275-1281 (1988).
Janda, et al., "Induction of an Antibody That Catalyzes the Hydrolysis of an Amide Bond" Science 241: 1188-1191 (1988).
Janda, et al., "Catalytic Antibodies with Lipase Activity and R or S Substrate Selectivity", Science 244: 437-440 (1989).
Jiang, Rapid detection of ras oncogenes in human tumors & applications to colon, Oncogene 4: 923-928 (1989).
Joyce, and Inouye, "A novel technique for the rapid preparation of mutant RNA's", Nucleic Acid Research 17: 711-722 (1989).
Krieg, and Melton, "Functional messenger RNA's are produced by SPG in vitro transcription of cloned cDNA's", Nucleic Acids Research 12: 7057-7070 (1984).
Lai, et al., "Conserved organization of the human murine T-cell receptor .beta. gene families". Nature 331: 543-546 (1988).
Lei, et al., "Characterization of the Erwinia carotovora pelB Gene and Its Product Pectate Lyase", J. Bac. 169: 4379-4383 (1987).
Larrick, et al., "Rapid Cloning of Rearranged Immunoglobulin Genes From Human Hybridoma Cells Using Mixed Primers and The Polymerase Chain Reaction", Biochem. Biophys. Research Comm. 3: 1250-1256 (1989).
Li, et al., Alteration of the amino terminus of the mature sequence of a protein can severely affect protein export in *Escherichia coli* , Proc. Natl. Acad. Sci. USA 85: 7685-7689 (1988).
Loh, et al., "Polymerase Chain Reaction with Single-Sided Specificity: Analysis of T Cell Receptor .delta. Chain", Science 243: 217-220 (1989).
Martin, and Castro, "Base pairing involving deoxylnosine: implications for probe design", Nucleic Acids Research 13: 8927-8938 (1985).
Marx, Jean , "Learning How To Bottle the Immune System" Science 246: 1250-1251 (1989).
McLeod, et al., "Identification of the Crossover Site during FLP-Mediated Recombination in the Saccharomyces cerevisiae Plasmid 2.mu.m Circle", Mol. Cell. Biol. 6: 3357-3367 (1985).
Morrison, Sherie L., "Transfectomas Provide Novel Chimeric Antibodies", Science 229: 1202-1207 (1985).
Mouva, et al., "Amino Acid Sequence of the Signal Peptide of ompA Protein, a Major Outer Membrane Protein of *Escherichia coli*", J. Biol. Chem. 255: 27-29 (1980).
Mullinax, et al., "Identification of human antibody fragment clones specific for tetanus toxoid in a bacteriophage .lambda. immunoexpression library", Proc. Natl. Acad. Sci. USA 87: 8095-8099 (1990).
Narang, et al., "Improved Phosphotriester Method for the Synthesis of Gene Fragments", Methods in Enzymol. 68: 90-98 (1979).
Neuberger, et al., "Recombinant antibodies possessing novel effector functions" Nature 312: 604-608 (1984).
Niman, et al., "Generation of protein-reactive antibodies by short peptides is an event of high frequency: Implications for the structural basis of immune recognition" Proc. Natl. Acad. Sci. USA 80: 4949-4953 (1983).

Ohtsuka, et al., "An Alternative Approach to Deoxyoligonucleotides as Hybridization Probes by Insertion of Deoxyinosine at Ambiguous Codon Positions", J. Biol. Chem. 360: 2605-2608 (1985).
Orlandi, et al., "Cloning immunoglobulin variable domains for expression by the polymerase chain reaction" Proc. Natl Acad.Sci. USA 86: 3833-3837 (1989).
Pollack, et al., "Selective Chemical Catalysis By An Antibody" Science 234: 1570-1573 (1986).
Raab, et al., Dominance in Lambda S Mutations and Evidence for Translational Control J. Mol. Biol. 199: 95-105 (1988).
Reader, et al., "Lysis Defective Mutants of Bacteriophage Lambda: Genetics and Physiology of S Cistron Mutants", Virology 43: 607-622 (1971).
Roberts, et al. "A general method for maximizing the expression of a cloned gene" Proc. Natl. Acad. Sci. USA 76: 760-764 (1979).
Roberts, et al. "Synthesis of simian virus 40 t antigen in *Escherichia coli*", Proc. Natl. Acad. Sci. USA 76: 5596-5600 (1979).
Ruoslahti and Pierschbacher, "New Perspectives in Cell Adhesion: RGD and Integrins" Science 238: 491-496 (1987).
Saiki, et al., "Enzymatic Amplification of .beta.-Globin Genomic Sequences and Restriction Site Analysis for Diagnosis of Sickle Cell Anemia", Science 230: 1350-1354 (1985).
Saiki, et al., Primer-directed Enzymatic Amplification of DNA with a Thermostable DNA Polymerase Science 239: 487-491 (1988).
Sanger, et al., "DNA sequencing with chain-terminating inhibitors", Proc. Natl. Acad. Sci. USA 74: 5463-5467 (1977).
Sastry, et al., "Cloning of the Immunological Repertoire in *Escherichia coli* for Generation of Monoclonal Catalytic Antibodies: Construction of a Heavy Chain Variable Region-specific cDNA Library" Proc. Natl. Acad. Sci. USA 86: 5728-5732 (1989).
Senecoff, et al."The FLP recombinase of the yeast 2-.mu.m plasmid: Characterization of its recombination site", Proc. Natl. Acad. Sci. USA 82: 7270-7274 (1985).
Shine, et al., "Determinant of cistron specificity in bacterial ribosomes", Nature 254: 34-38 (1975).
Short, et al., "ZAP: A Bacteriophage .lambda. expression Vector With in vivo Excision Properties", Nucleic Acids Research 16: 7583-7597 (1988).
Skerra, et al., "Assembly of A Functional Immunoglobulin F.sub.v Fragment In *Escherichia coli*" Science 240: 1038-1040 (1988).
Sommer and Tautz, "Minimal homology requirements for PCR primers", Nucl. Acids Res. 17: 6749 (1989).
Iverson, Sorge, et al., "A Combinatorial System for Cloning and Expressing the Catalytic Antibody Repertoire in *Escherichia coli*", Cold Spring Harbor Laboratory Press vol. LIV pp. 273-281 (1989).
Sorge, et al., "Amphotropic Retrovirus Vector Systems for Human Cell Gene Transfer", Mol. Cell Biol. 4: 1730-1737 (1984).
Southern E.M., "Detection of Specific Sequences Among DNA Fragments Separated by Gel Electrophoresis", J. Mol. Biol. 98: 503-517 (1975).
Studier, and Moffatt, "Use of Bacteriophage T7 RNA Polymerase to Direct Selective High-level Expression of Cloned Genes", J. Mol. Biol. 189: 113-130 (1986).
Suzuki, et al., "cDNA and amino acid sequences of the cell adhesion protein receptor recognizing vitronectin reveal a transmembrane domain and homologies with other adhesion protein receptors", Proc. Natl. Acad. Sci. USA 83: 8614-8618 (1986).
Takahashi, et al., "Molecular cloning of the human cholecystokinin gene by use of a synthetic probe containing deoxyinosine", Proc. Natl. Acad. Sci. USA 82: 1931-1935 (1985).
Tramontano, et al., "Catalytic Antibodies", Science 234: 1566-1569 (1986).
Tuniguchi, and Weissmann, "Site-directed Mutations in the Initiator Region of the Bacteriophage Q.beta. Coat Cistron and Their Effect on Ribosome Binding", J. Mol. Biol. 118: 533-565 (1978).
Vitetta, et al., "Immunotoxins: A New Approach to Cancer Therapy", Science 219: 644-650 (1983).
Ward, et al., "Binding Activities of A Repertoire of Single Immunoglobulin Variable Domains Secreted From *Escherichia coli*", Nature 341: 544-546 (1989).
Whal, et al., "Improved Radio imaging and tumor Localization with monoclonal F(ab).sub.2", J. Nucl. Med. 24: 316 (1983).

Wigler, et al., "DNA-mediated transfer of the adenine phosphoribosyltransferase locus into mammalian cells", Proc. Natl. Acad. Sci. USA 76: 1373-1376 (1979).
Winter, and Milstein, "Man-made antibodies", Nature 349: 293-299 (1991).
Zalcberg, John R. "Tumor localization using radiolabeled monoclonal antibodies", Am.J. Clin. Oncol. 8: 481-489 (1985).
Akowitz and Manuelidis, "A novel cDNA/PCR strategy for efficient cloning of small amounts of undefined RNA", Gene 81: 295-306 (1989).
Belyavsky, et al., "PCR-based cDNA library construction: general cDNA libraries at the level of a few cells", Nucleic Acids Research 17: 2929-2932 (1989).
Larrick, et al., "Generation of Specific Human Monoclonal Antibodies By In Vitro Expansion of Human B Cells: A Novel recombinant DNA Approach", In Vitro Immunization in Hybridoma Technology, p. 231-246 (1988).
Moore, Gordon, "Genetically Engineered Antibodies", clin. Chem. 35: 1849-1853 (1989).
Ohara, et al., "One-sided polymerase chain reaction: The amplification of cDNA", Proc. Natl. Acad. Sci. USA 86: 5673-5677 (1989).
Rathburn, et al., "Making antigen-receptor genes", Nature 342: 863-864 (1989).
Biotechnology Newswatch, "Antibody genes cloned in bacteria, bypassing tumor cells animals", p. 4 (Jan. 15, 1990).
Ho, et al., "Site-directed mutagenesis by overlap extension using the polymerase chain reaction", Gene 77: 51-59 (1989).
Barbas, et al., "Assembly of combinatorial antibody libraries on phage surfaces: The gene III site", Proc. Natl. Acad. Sci. USA 88: 7978-7982 (1991).
Chang, et al., "Expression of Antibody Fab Domains on Bacteriophage Surfaces", J. Immun. 147: 3610-3614 (1991).
Clackson, et al., "Making antibody fragments using phage display libraries", Nature 352: 624-628 (1991).
Hoogenboom, et al., "Multi-subunit proteins on the surface of filamentous phage: methodologies for displaying antibody (Fab) heavy and light chains", Nucleic Acids Research 19: 4133-4137 (1991).
Kang, et al., "Linkage of recognition and replication functions by assembling combinatorial antibody Fab libraries along phage surfaces", Proc. Natl. Acad. Sci. USA 88: 4363-4366 (1991).
McCafferty, et al., "Phage antibodies: filamentous phage displaying antibody variable domains", Nature 348: 552-555 (1990).
Huse, Antibody Engineering: A Practical Guide "Combinatorial Antibody Expression Libraries in Filamentous Phage" p. 103-120.
Weisberg and Landy "Site-specific Recombination of Phage Lambda", Lambda II, Cold Spring Harbor Laboratory Press pp. 211-217 (1983).
Kabat, et al., Sequences of Proteins of Immunological Interest 4th Edition U.S. Dept. of Health and Human Services pp. 494-525 (1987).
Amit, A., et al, "Three-Dimensional Structure of an Antigen-Antibody Complex at 2.8 A Resolution",Science 233:747-753 (1986).
Amzel, L., et aL, "Three-Dimensional Structure of Immunoglobulins", Ann. Rev. Biochem. 48:961-97 (1979).
Baldwin, E., et aL, "Generation of a Catalytic Antibody by Site-Directed Mutagenesis", Science 245:1104-1107 (1989).
Better, M., et aL, "*Escherichia coli* Secretion of an Active Chimeric Antibody Fragment", Science240:1041-1043 (1988).
Bosslet, et al, "Immunohistochemical Localization and Molecular Characteristics of Three Monoclonal Antibody-Defined Epitopes Detectable on Carcinoembryonic Antigen (CEA)", J. Cancer 36: 75-84 (1985).
Bosslet, K., et al, "Quantitative considerations supporting the irrelevance of circulating serum CEA for the immunoscintigraphic visualization of CEA expressing carcinomas", Eur. J. Nuc. Med. 14:523-528 (1988).
Bosslet, K., et al, "A monoclonal antibody with binding and inhibiting activity towards human pancreatic carcinoma cells," Cancer Immunol Immunother. 23:185-191 (1986).
Boulianne, G., et al, "Production of Functional Chimaeric Mouse/Human Antibody", Nature312:643-646 (1984).

Bremer, et al, "Characterization of a Glycospingolipid Antigen Defined by the MonoclonalAntibody MBrl Expressed in Normal and Neoplastic Epithelial Cells of Human Mammary Gland,"J.BioL Chem. 259 (23):14773-14777 (1984).

Bruggemann, M., et al, "Comparison of the Effector Functions of Human Immunoglobulins UsingMatched Set of Chimeric Antibodies,"J. Exp. Med. 166:1351-1361 (1987).

Bruggemann, M., et al, "Construction, Function and Immunogenicity of Recombinant Monoclonal Antibodies", Behring Inst. Mitt. 87:21-24 (1990).

Carter, P., et al, "Improved oligonucleotide site-directed mutagenesis using MI 3 vectors", Nuc. Acids Res. 13(12):4431-4443 (1985).

Chaidaroglou, A., et al, "Function of Arginine-1 66 in the Active Site of Escherichia coli Alkaline Phosphatase", Biochem. 27:8338-8343 (1988).

Chiang, Y., et al, "Direct cDNA Cloning of the Rearranged Immunoglobulin Variable Region", Biotechniques 7(4):360-366 (1989).

Cioe, L., et al, "Cloning and Nucleotide Sequence of a Mouse Erythrocyte B-Spectrin cDNA", Blood 70(4):915-920 (1987).

Cioe, L., et al, "Detection and Characterization of a Mouse a-Spectrin cDNA Clone by Its Expression in Escherichia coli", Proc. Natl. Acad. Sci. USA 82: 1367-1371 (1985).

Colman, P., et al, "Three-dimensional structure of a complex of antibody with influenza virus neuraminidase", Nature 326:358-363 (1987).

Dagert, M., et al, "Prolonged Incubation Calcium Chloride Improves the Competence of Escherichia coli Cells" , Gene, 6:23-28 (1979).

Dolby, T., et al, "Cloning and Partial Nucleotide Sequence of Human Immunoglobulin p-chain CDNA from B cells and Mouse-Human Hybridomas", Proc. Natl. Acad. Sci. USA 77(10):6027-6031 (1980).

Edmundson, A., et al, "Rotational Allomerism and Divergent Evolution of Domains in Immunoglobulin Light Chains", Biochemistry 14(18):3953-3961 (1975).

Fields, S., et al, "Novel genetic system to detect protein-protein interactions", Nature 340:245-246 (1989).

Galfre, G., et aL, "Preparation of Monoclonal Antibodies: Strategies and Procedures", Meth.Enzym. 73:3-47 (1981).

Glockshuber, R., et al, "The Disulfide Bonds in Antibody Variable Domains: Effects on Stability, Folding in Vitro, and Functional Expression in Escherichia coli", Biochemistry 31 (5):1270-1279 (1992).

Green, N., et al, "Immunogenic Structure of the Influenza Virus Hemagglutinin", Cell 28:477-487 (1982).

Griffiths, G., et al, "The Analysis of Structural Diversity in the Antibody Response", Hybridoma Technology in the Biosciences and Medicine 103-115 Ed. T.A. Springer, Plenum Press (1985).

Grodberg, J., et aL, "ompT Encodes the Escherichia coli Outer Membrane Protease that Cleaves T7 RNA Polymerase during Purification", J. BacterioL 170(3):1245-1253 (1988).

Gronenborn, B., "Overproduction of Phage Lambda Repressor under Control of the lac Promoter of Escherichia coli, " Mol Gen. Genet. 148:243-250 (1976).

Gubler, U., et al,"A simple and very efficient method for generating cDNA libraries", Gene 25:263-269 (1983).

Hanahan, D., "Studies on Transformation of Escherichia coli with Plasmids", J. MoL Biol 166:557-580 (1983).

Herrmann, B., et al, Isolation of Genomic DNA, Methods in Enzymol 152:180-197 (1987).

Holmes, D., et al, "A Rapid Boiling Method for the Preparation of Bacterial Plasmids", Analytical Biochem. 114:193-197 (1981).

Honjo, T., Immunoglobulin Genes, "Ann. Rev. Immuno", 1:499-528 (1983).

Hunkapiller, T., et al, "The Growing Immunoglobulin Gene Superfamily", Nature 323: 15-16 (1986).

Huston, et al, "Protein engineering of antibody binding sites: recovery of specific activity in an anti-digoxin single-chain Fv analogue produced in Escherichia coli", Proc. Natl. Acad. Sci. USA 85:5879-5883 (1988).

Inbar, D., et al, "Localization of Antibody-Combining Sites within the Variable Portions of Heavy and Light Chains", Proc. Natl. Acad. Sci USA 69(9):2659-2662 (1972).

Janda, et al, Induction of an Antibody that Catalyzes the Hydrolysis of an Amide Bond, Science 241:1188-1191 (1988).

Janda, et al, "Catalytic Antibodies with Lipase Activity and R or S Substrate Selectivity", Science 244:437-440 (1989).

Jaton, et al, "Recovery of Antibody Activity upon Reoxidation of Completely Reduced Polyalanyl Chain and Its Fd Fragment Derived from Anti-2,4-dinitrophenyl Antibody", Biochemistry 7(12):4185-4195 (1968).

Jones, P., et al, "Replacing the complementarity-determining regions in a human antibody with those from a mouse", Nature 321:522-525 (1986).

Joyce, G., et al, "A novel technique for the rapid preparation of mutant RNA's", Nucleic Acids Research 17(2):711-722 (1989).

Kaczmarek, L., et al, "Cell-Cycle-Dependent Expression of Human Ornithine Decarboxylase", J. Cellular Physiol 132:545-551 (1987).

Kearney, J., et al, "A New Mouse Myeloma Cell Line That Has lost Immunoglobulin Expression but Permits the Construction of Antibody-Secreting Hybrid Cell Lines", J. Immunol 123(4):I 5481550 (1979).

Kokubu, F., et al, "Complete structure and organization of immunoglobulin heavy chain constant region genes in a phylogenetically primitive vertebrate", EMBO J. 7(7):1979-1988 (1988).

Kramer, B., et al, "Different Base/Base Mismatches Are Corrected with Different Efficiencies by the Methyl-Directed DNA Mismatch-Repair System of E. coli", Cell 38:879-887 (1984).

Krieg, P., et al, "Functional messenger RNA's are produced by SPG in vitro transcription of cloned cDNA's", Nucleic Acids Research 12(18):7057-7070 (1984).

Laemmli, U., "Cleavage of Structural Proteins during the Assembly of the Head of Bacteriophage T4", Nature 227:680-685 (1970).

Lai, E., et al, Conserved organization of the human and murine T-cell receptor B-gene families, Nature 331:543-546 (1988).

Land, H., et al, "5'-Terminal sequences of eucaryotic MRNA can be cloned with high efficiency," Nucleic Acids Research 9(10):2251-2267 (1981).

Larrick, et al, "Rapid Cloning of Rearranged Immunoglobulin Genes from Human Hybridoma Cells Using Mixed Primers and the Polymerase Chain Reaction", Biochem,Biophys.Res.Comm. 60(3):1250-1256 (1989).

Larrick, J., et al, Progress in Biotechnology, In Vitro Immunization in Hybridome Technology Elsevier Science Publishers, Amsterdam 231-246 (1988).

Lee, C., et al, "Generation of CDNA Probes Directed by Amino Acid Sequence: Cloning of Urate Oxidase", Science 239:1288-1291 (1988).

Lei, S., et al, "Characterization of the Erwinia carotovora pelb Gene and Its Product Pectate Lyase", J. Bac 169(9):4379-4383 (1987).

Mack, D., et al, "A Sensitive Method for the Identification of Uncharacterized Viruses Related to Known Virus Groups: Hepadnavirus Model System", Proc. Natl. Acad. Sci. USA 85:6977-6981 (1988).

Maniatis, et al, Molecular Cloning: A Laboratory Manual Cold Spring Harbor Laboratory (1982).

Mariuzza, R., et al, "Preliminary Crystallographic Study of the Complex Between the Fab Fragment of a Monoclonal Anti-lysozyme Antibody and its Antigen", J. Mol Biol 170:1055-1058 (1983).

Martin, F., et al, Base pairing involving deoxyinosine; implications for probe design, Nuc Acids Research 13(24):8927-8938 (1985).

McCormack, W., et al, "Comparison of Latent and Nominal Rabbit lg Vhal Allotype CDNA Sequences", Journal of Immunology 141(6):2063-2071 (1988).

Menard, S., et al, "Generation of Monoclonal Antibodies reacting with Normal and Cancer Cells of Human Breast", Cancer Res., 43:1295-1300 (1983).

Miller, R., et al, "Monoclonal Antibody Therapeutic Trials in Seven Patients with T-Cell Lymphoma", Blood 62(5):988-995 (1983).

Morrison, S., et al., "Chimeric Human Antibody Molecules: Mouse Antigen-Binding Domains with Human Constant Region Domains", Proc. Natl. Acad. Sci. USA 81:6851-6855 (1984).
Morrison, S., "Transfectomas Provide Novel Chimeric Antibodies", Science 229:1202-1207 (1985).
Narang, S., et al., "Improved Phosphotriester Method for the Synthesis of Gene Fragments", Meth. Enzymol 68:90-98 (1979).
Neuberger, M., et al, "A Hapten-Specific Chimaeric IgE Antibody with Human Physiological Effector Function", Nature 314:268-270 (1985).
Neuberger, M., et al, "Expression and regulation of immunoglobulin heavy chain gene transfected into lymphoid cells", EMBO J., 2:1373-1378.
Neuberger, M., et al., "Protein Engineering of Antibody Molecules", Protein Engineering Ch 19:31-317 Academy Press (1986).
Neuberger, M., et al, "The expression of immunoglobulin genes", Immunology Today 9(9):278-281 (1988).
Neuberger, M., et al., "Antibody Engineering", Proc. 8th Invit Biotech. Symp. Soc. Francaise de Microbial 792-799 (1988).
Neuberger, M., et al "Making novel antibodies by expressing transfected immunoglobulin genes", Trends in Biochemical Sciences 10(9):347-349 (1985).
Neuberger, M., et al, "Construction of novel antibodies by use of DNA transfection: design of plasmid vectors," Phi Trans. R.S. Lond. A317:425-432 (1986).
Ochi, A., et al"Transfer of a cloned immunoglobulin light-chain gene to mutant hybridoma cells restores specific antibody production", Nature 302:340-342 (1983).
Oi, V., et al., "Immunoglobulin gene expression in transformed lymphoid cells", Proc. Natl. Acad. Sci. USA 80:825-829 (1983).
Padian, E., et al, "Structure of an antibody-antigen complex: Crystal structure of the HyHEL-1 0 Fab-lysozyme complex", Proc. Natl. Acad. Sci USA 86:5938-5942 (1989).
Porter, R., et al, "Subunits of Immunoglobulins and their Relationship to Antibody Specificity", J. Cellular Physiol 67(3) Supp. 1:51 (1966).
Potter, H., et al, "Enhancer-dependent expression of human K immunoglobulin genes introduced into mouse pre-B lymphocytes by electroporation" Proc. Natl. Acad. Sci USA 81:7161-7165 (1984).
Proba, K., et al., "A Natural Antibody Missing a Cysteine in VH: Consequences for Thermodynamic Stability and Folding", J. Mol Biol 265:161-172 (1997).
Proba, K., et al, "Antibody scfv Fragments without Disulfide Bonds Made by Molecular Evolution", J. Mol. Biol. 275:245-253 (1998).
Riechmann, L., et al., "Reshaping human antibodies for therapy", Nature 332:323-327 (1988).
Rockey, J., "Equine Antihapten Antibody", J. Exp. Med., 125:249-275 (1967).
Rossman, M., et al., "Structure of a human common cold virus and functional relationship to other picornaviruses", Nature 317:145-153 (1985).
Roth, M., et al., "Selection of Variable-Joining Region Combinations in the Chain of the T Cell Receptor", Science 241:1354:1358 (1985).
Saiki, R., et al., "Enzymatic Amplification of B-Gobin Genomic Sequences and Restriction Site Analysis for Diagnosis of Sickle Cell Anemia", Science 230:1350-1354 (1985).
Satow, Y., et al., "Phosphocholine Binding Immunoglobulin Fab McPC603, An X-ray Diffraction Study at 2-7 A.", J. Mol. Biol. 190:593-604 (1986).
Scharf, S., et al., "Direct Cloning and Sequence Analysis of Enzymatically Amplified Genomic Sequences", Science 233:1076-1078 (1986).
Schwager, J., et al., "Amino acid sequence of heavy chain from Xenopus laevis IgM deduced from cDNA sequence: Implications for evaluation of immunoglobulin domains", Proc. Natl. Acad. Sci. USA 85:2245-2249 (1988).
Sharon, J., et al., "Expression of a VHCK Chimaeric Protein in Mouse Myeloma Cells", Nature 309:364-367 (1984).
Sheriff, S., et al., "Three-dimensional structure of an antibody-antigen complex", Proc. Natl. Acad. Sci. USA 84:8075-8079 (1987).

Shine, J., et al., "Determinant of cistron specificity in bacterial ribosomes", Nature 254:34-38 (1975).
Short, J., et al., "ZAP: A Bacteriophage lambda expression Vector with in vivo Excision Properties", Nucleic Acids Research 16(15):7583-7600 (1988).
Southern, P., et al., "Transformation of Mammalian Cells to Antibiotic Resistance with a Bacterial Gene Under Control of the SV40 Early Region Promoter", J. Mol. Appl. Genet. 1:327-341 (1982).
Staden, R., "The current status and portability of our sequence handling software", Nucleic Acids Res. 14(I):217-231 (1986).
Stevenson, G., "The Binding of Haptens by the Polypeptide Chains of Rabbit Antibody Molecules", Biochem. J., 133:827-836 (1973).
Takeda, S., et al., "Construction of Chimaeric Processed Immunoglobulin Genes Containing Mouse Variable and Human Constant Region Sequences", Nature 314:452-454 (1985).
Taniguchi, T., et al., "Site-directed Mutations in the Initiator Region of the Bacteriophage Beta Coat Cistron and Their Effect on Ribosome Binding", J. Mol. Biol. 118:533-565 (1978).
Tonegawa, S., "Somatic Generation of Antibody Diversity", Nature 302:575-581 (1983).
Verhoeyen, M., et al., "Reshaping human antibodies: grafting an antilysozyme activity", Science 239:1534-1536 (1988).
Wigler, M., et al., "DNA-mediated transfer of the adenine phosphoribosyltransferase locus into mammalian cells", Proc. Natl. Acad. Sci USA 76(3):1373-1376 (1979).
Winter, G., "The use of synthetic oligodeoxynucleotide primers in cloning and sequencing segment 8 of influenza virus (A/PR/8/34)", Nucl. Acids Res. 9:237-245 (1981).
Winter, G, "Restructering Enzymes and Antibodies", Investigation and Exploitation of Antibody Combining Sites, pp. 129-140, Reid et al., eds., Plenum Publishing Corporation (1985).
Yanisch-Perron, C., et al., "Improved M13 phage cloning vectors and host strains: nucleotide sequences of the M13mp18 and pUC19 vectors", Gene 33:103-119 (1985).
Yon, J., et al., "Precise gene fusion by PCR", Nucl. Acids Res. 17(12):4895 (1989).
Zaloberg, J., "Tumor localization using radiolabeled monoclonal antibodies", Am. J. Clin. Oncol. 8:481-489 (1985).
Zoller, M., et al., "Oligonucleotide-directed mutagenesis using M13-derived vectors: an efficient and general procedure for the production of point mutations in any fragment of DNA", Nucl. Acids Res. 10(20):6457-6500 (1982).
Chothia et al., "Conformations of immunoglobulin hypervariable regions", Nature 342:877-883 (1989).
Chothia et al., "The Predicted Structure of Immunoglobulin D1.3 and Its Comparison with the Crystal Structure", Science 233:756-758 (1986).
Chothia et al., "Canonical Structures for the Hypervariable Regions of Immunoglobulins", J. Mol. Biol., 196:901-917 (1987).
Larrick, J., "Rapid Cloning of Rearranged Immunoglobulin Genes from Human Hybridoma Cells Using Mixed Primers and the Polymerase Chain Reaction", Biochem. Biophys. Res. Comm. 160(3):1250-1256 (1988).
Interlocutory Decision European Patent No. 368,684; Sep. 3, 1994 EP in Opposition Proceedings (Art.102(3) and 106(3) EPC May 29, 2000 from Oral Proceedings held Oct. 14, 1999 in file of EP No. 368,684.
Roth et al., "Selection of Variable-Joining Region Combinations in the Chain of the T Cell Receptor", Science 241:1354-1358 (1988).
Ruoslahti et al., New Perspectives in Cell Adhesion.
Saiki et al., "Primer-Diected Enzymatic Amplification of DNA with a Thermostable DNA Polymerase", Science 239:487-491 (1988).
Sanger et al., "DNA sequencing with chain-terminating inhibitors", PNAS (USA) 74(12):5463-5467 (1977).
Sastry et al., PNAS (USA) 86:5728-5732 (1989).
Verhoeyen et al., "Engineering of Antibodies", Bioassays 8(2):74-78 (1988).
Cohen et al., "Nonchromosomal Antibiotic resistance in Bacteria: Genetic Transformation of *Escherichia coli* by R-Factor DNA", PNAS (USA) 69(8):2110-2114 (1972).
Gearhart et al., "IgG antibodies to phosphorylcholine exhibit more diversity than their IgM counterparts," Nature 391:29-34 (1981).
Ginsberg et al., Virology 52:456-467 (1973).

Kabat et al. "Sequences of Proteins of Immunological Interest", 4th ed. U.S. Health and Human Services pp. 494-525 (1987).

Neuberger et al., "Antibody Engineering", Proc. 8th Invit. Biotech Symposium. Soc. Francoise de Microbial. 792-799 (1988).

Skerra et al., "Assembly of a functional Immunoglobulin Fv Fragment in *Escherichia coli*", Science 240:1038-1041 (1988).

Sorge et al., "Amphotropic Retrovirus Vector System for Human Cell Gene Transfer", Mol. Cell. Biol. 4(9):1730-1737 (1984).

Studier et al., "Use of Bacteriophage T7 RNA Polymerase to direct selective high-level expression of cloned genes", J. Mol. Biol. 189:113-130 (1986).

Suzuki et al., PNAS (USA) 83:8614-8618 (1986).

Tramontano et al., "Catalytic Antibodies", Science 234:1566-1569 (1986).

Bird et al., "Single-Chain Antigen-Binding Proteins", Science 242:423-426 (1988).

Appeal Brief of Opposition to EP-B-0368 684, filed by MorphoSys and submitted to the Technical Appeal Board of European patent Office on Oct. 9, 2000.

Chua et al., "Germ-Line Affinity and Germ-Line Variable-Region Genes in the B Cell Response", J. Immunol. 138(4):1281-1288 (1987).

Kimura et al., J. Immunol. 140(4):1212-1217 (1988).

Roitt et al., "The Generation of Antibody Diversity", Immunology, Gower Medical Publishing pp. 9.1-9.11 (1985).

Kabat et al., "Antibody Complementarity and Antibody Structure", J. Immunol., 141 (7-Suppl.):S25-S36.

Fischauf, "Digestion of DNA: Size Fractionation", Meth. Enzymol. 152:183-189 (1987).

Larrick et al., In Vitro Immunization in Hybridoma Technology, C.A.K. Borrebaeck, ed., Elsevier Science Publishers, Amsterdam, pp. 231-246 (1988).

Movva et al., "Amino Acid Sequence of the Signal Peptide of ompA Protein, a Major Outer membrane Protein of *Escherichia coli*", J. Biol. Chem. 255(1):27-29 (1980).

Niman et al., PNAS (USA) 80:4949-4953 (1983).

Ohtsuka et al., J. Biol. Chem. 260(5):2605-2608 (1985).

Pollack et al., "Selective Chemical Catalysis by an Antibody", Science 234:1570-1573 (1986).

Mullinax et al., Proc. Natl. Acad. Sci. USA, 87:8095-8099 (1990).

Ward et al., Nature, 341:544-546 (1989).

Caton et al., Proc. Natl. Acad. Sci. USA, 87:6450-6454 (1990).

* cited by examiner

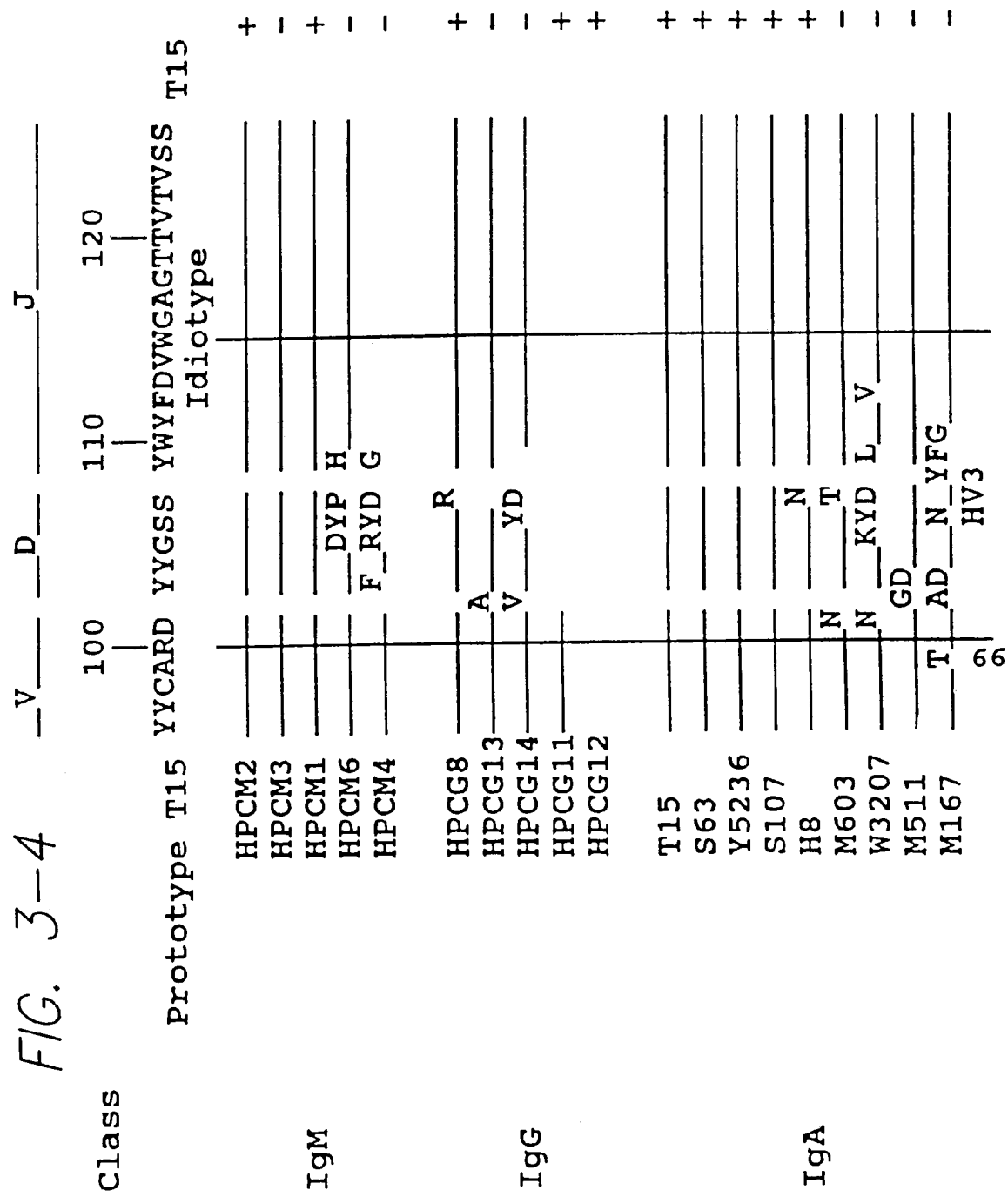

FIG. 5

```
Subclass I (A)
L39  CTCGAGTCAGGACCTGGCCTCGTGAAACCTTCTCAGTCTCTGTCTCCATCACCAGTGCTTATTACTGGAACTGGATCCGGCAGTT Subclass II (A)
L11  CTCGAGTCTGGGCCTnAAACTGGCAAAACCTGGGGCCTCAGTGAAGATGTCCTGCAAGGCTTCTGGCCACACCTTGACTAGTTACTGGATACACTGGGTAAAAnAGAGGCC
#L03  CTCGAGTCTGGACCTnAGCTGGACCTGGTAAAGCCTGGGGTTCAGTGAAGATGTCCTGCAAGGCTTCTGGATACACATTCACnAGCTATGTTATACACTGGGTGAAGCAGAAGCCT
L32  CTCGAGTCTGGACCTGGACCTGAACTGGTAAAGCCTGGGACTTCAGTGAAGATGTCCTGCAAGGCTTCTGGATACACATTCACCAGCTATGTTATGCGCTGGGTGAAGCAGAAGCC Subclass II (B)
L37  CTCGAGTCAGGGGCTGAACTGGTAAGGCCTGGGGTTTCAGTGAAGTTGTCCTGCAAGGCTTCTGGCTACACCTTCACnAGCTACTATATGTACTGGGTGAAGCAGAGGCC
L06  CTCGAGTCTGGGGCTAAGGCTGGTAAGGCCTGGAGCTTnAGTnAAGCTGTCCTGnAGGGCTTCTGGCTACTCCTTCACnAGCTACTGGGTGAAGCAGAGAGGCC Subclass II (C)
L33  CTCGAGTCTGGGGCTGAGGCTGGTGAGGCCTGGAGCTTCAGTnAAGCCTGCAAGGCCTCTGCAAGGCCTCTCGTACTCCTTCACCAGTCCTGATAACTGGGTGAAGCAGAGGCTGG Subclass III (B)
L36  CTCGAGTCAGGAGGTGGCCTGGTGCCTGGTGCAGCCTGGAGGATCCCTGAAACTCTCCTGTGCAGCCTCAGGATTCGATTTnAGnAGATACTGGATGAATTGGGTCCGGCAGCTCCA
#L02  CTCGAGTCTGGAGGTGGCCTGGTGCCTGGTGCAGCCTGGAGGATCCCTGAATCCCTGAAACTCTCCTGTGCAGCCTCAGGATTCGATTTnAGnAGATAATGGATGAGTTGGGTTCGGCAGGCTCC
#L31  CTCGAGTCTGGAGGTGGCCTGGTGCCTGGTGCAGCCTGGAGGATCCCTGAAAGTCTCCTGTGCAGCCTCAGGATTCGATTTnAGnAGATACTGGATGAGTTGGGTCCGGCAGCTCCA
#L34  CTCGAGTCTGGAGGTGGCCTGGTGCCTGGTGCAGCCTGGAGGATCCCTCAAACTCTCCTGTGCAGCCTCAGGATTCGATTTnAGnAGATACTGGATGAGTTGGGTCCGGCAGCTCCA
L50  CTCGAGTCAGGAGGAGGTGGCCTGGTGCAGCCTGGAGGAGCCCTGAAACTCTCCTGTGCAGCCTCAGGATTCGATTTnAGnAGATACTGGATGAGTTGGGTCCGGCAGCTCCAG Subclass III (C)
L10  CTCGAGTCTGGGGGAGGCTTAGTnCAGCCTGGAGGGTCCCGGAAACTCTCCTGTGCAGCCCTCTGGATTCACTTTnAGnAGTTTTGGAATGCACTGGATTCGTCAGGCTCC
L08  CTCGAGTCTGGGGGAGGCTTAGTnAGCCTGGAGGGTCCCGGAAACTCTGGAGGGTCCCGGAAACTCTCCTGTGCAGCCTCTGGATTCACTTTnAGnAGCTTTGGAATGCACTGGGTTACGTCAGGCTC Subclass V (A)
L38  CTCGAGTCAGGGCCTGAACTGGTGAGGCCTGGGCCTTCAGTGAGGCGTTCAGTnAAGATGTCCTGCAAGGCTTCAGGCTATTCCTTCACCAGGCTACTGATGCACTGGGTGAAACAGAGGCC Miscellaneous
47   CTCGAGTCAGGGCTGAACTGGTGAAGCCTGGGGCTTCAGTAAAGATGTCCTGCAAGGCTTCTGGCTACACCTCTTCTTCCTTCGGCTGCTGGATAAAGAAGGCCT
#L35  CTCGAGTCTGGACCTGGACCTnAGCTGGTGAAGCCTGGGGTTCAGTTAAAATATCCTGCAAGGGTTAACTCATTTTCTnTCTACTTTGTGAACTGGGTGATGCAGAGCCAT
#L48  CTCGAGTCAGGGCCTGAACTGGTGAAGCCTGGGGTTCAGTAAGTTGTCCTGAAGGCTTCGTCGAAGGCTACACCTTCACCATCATAGTACTGGGTGAAGCAGAGGCCTGG
```

FIG. 6A-1

V_H EXPRESSION VECTOR:

SHINE-DALGARNO MET

GGCCGCAAATTCTATTTCAAGGAGACAGTCATAATG
CGTTTAAGATAAAGTTCCTCTGTCAGTATTAC

LEADER SEQUENCE

AAATACCTATTGCCTACGGCAGCCGCT
TTTATGGATAACGGATGCCGTCGGCGA

LEADER SEQUENCE

GGATTGTTATTACTCGCTGCCCAACCAG
CCTAACAATAATGAGCGACGGGTTGGTC

FIG. 6A-2

| LINKER | | LINKER | |
|---|---|---|---|
| NCOI | V_H BACKBONE | XHOI | SPEI |

CCATGGCCCAGGTGAAACTGCTCGAGATTTCTAGACTAGT
GGTACCGGGTCCACTTTGACGAGCTCTAAAGATCTGATCA

STOP   LINKER

TyrProTyrAspValProAspTyrAlaSer
TACCCGTACGACGTTCCGGACTACGGTTCTTAATAGAATTCG
ATGGGCATGCTGCAAGGCCTGATGCCAAGAATTATCTTAAGCAGCT

FIG. 6B-1

$V_L$ EXPRESSION VECTOR:

SHINE-DALGARNO

GGCCGCAAATTCTATTTCAAGGAGACAGTCATA
CGTTTAAGATAAAGTTCCTCTGTCAGTAT

MET         LEADER SEQUENCE

ATGAAATACCTATTGCCTACGGCAGCCGCTGGA
TACTTTATGGATAACGGATGCCGTCGGCGACCT

LEADER SEQUENCE

TTGTTATTACTCGCTGCCCAACCAG
AACAATAATGAGCGACGGGTTGGTC

FIG. 6B-2

LINKER

| NCOI | $V_H$ BACKBONE |

CCATGGCCCAGGTGAAACTG
GGTACCGGGTCCACTTTGAC

LINKER

| XHOI | SPEI | STOP |

CTCGAGAATTCTAGACTAGTTAATAG
GAGCTCTTAAGATCTGATCAATTATCAGCT

FIG. 10

ECOR I      SHINE-DALGARNO    MET

TGAATTCTAAACTAGTCGCCAAGGAGACAGTCATAATGAAAT
ACTTAAGATTTGATCAGCGGTTCCTCTGTCAGTATTACTTTA

LEADER SEQUENCE

ACCTATTGCCTACGGCAGCCGGCTGGATTGTGTTATTACTCGCTGCCCAACCAG
TGGATAACGGATGCCCGTCGGCCGACCTAACACAATAATGAGCGACGGGTTGGTC

NCO I    SAC I      XBA I     Not I

CCATGGCCGAGCTCGTCAGTTCTAGAGTTAAGGGCCG
GGTACCGGCTCGAGCAGTCAAGATCTCAATTCCCGGGCAGCT

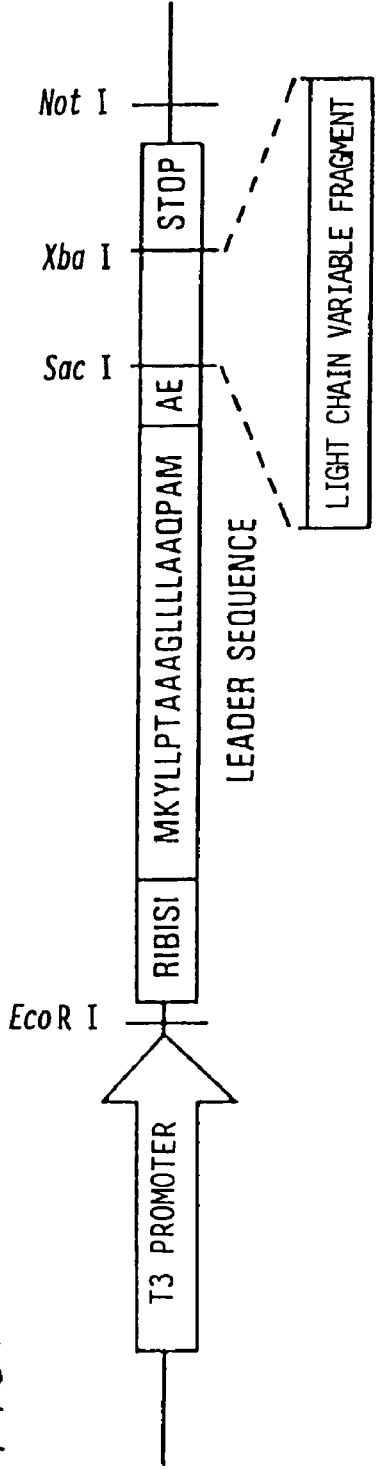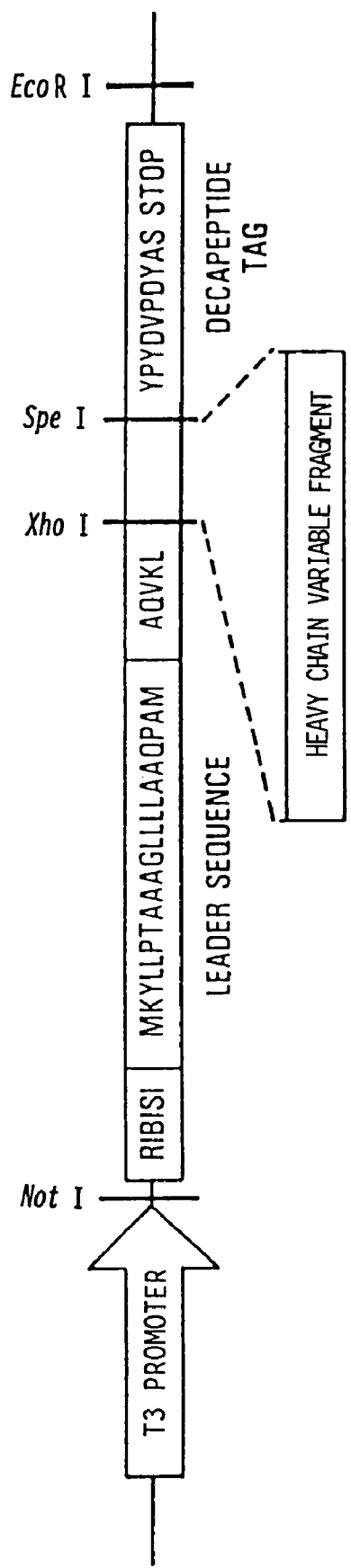
FIG. 11-1
FIG. 11-2

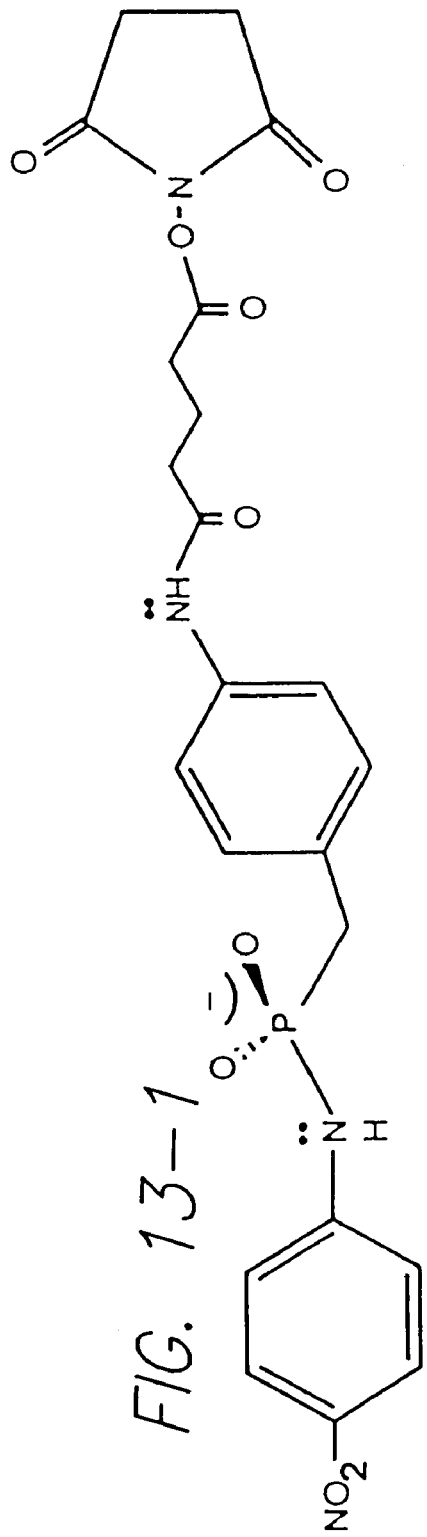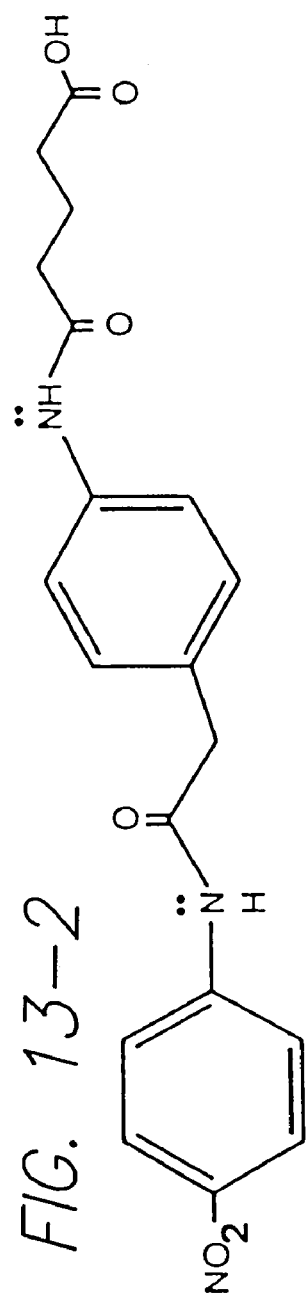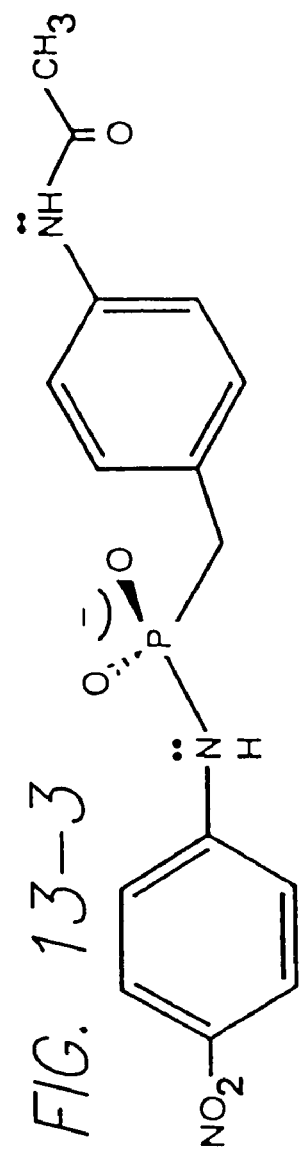
FIG. 13-1      FIG. 13-2      FIG. 13-3

A

SupF

```
5' TCGAGCGCCGATCCGCTTCCCGATAAGGGAGCAGGCCAGTAAAAGCATTA
3'     CGCGGCTAGGCGAAGGGCTATTCCCTCGTCCGGTCATTTTCGTAAT

CCTGTGGTGGGGTTCCCGAGCGGCCAAAGGGAGCAGACTCTAAATCTGCC
    GGACACCACCCCAAGGGCTCGCCGGTTTCCCTCGTCTGAGATTTAGACGG

GTCATCGACTTCGAAGGTTCGAATCCTTCCCCCACCACCATCACTTTCAA
    CAGTAGCTGAAGCTTCCAAGCTTAGGAAGGGGGTGGTGGTAGTGAAAGTT

AAGTCCGACTAGTTACCCGTACGACGTTCCGGACTACGCTTCTTAATAG      3'
    TTCAGGCTGATCAATGGGCATGCACGAAGGCCTCATGTGAAGAATTATCTTAA 5'
```

B

SupF

```
5'     CGCCCGATCCGCTTCCCGATAAGGGAGCAGGCCAGTAAAAGCATTACCTG
3' TCGTGCGGGCTAGGCGAAGGGCTATTCCCTCGTCCGGTCATTTTCGTAATGGAC

TGGTGGGGTTCCCAGCGGCCAAAGGGAGCAGACTCTAAATCTGCCGTCA
    ACCACCCCAAGGGTCGCCGGTTTCCCTCGTCTGAGATTTAGACGGCAGT

TCGACTTCGAAGGTTCGAATCCTTCCCCCACCACCATCACTTTCAAAAGT
    AGCTGAAGCTTCCAAGCTTAGGAAGGGGGTGGTGGTAGTGAAAGTTTTCA

CCGACTAGGGCCT       3'
    GGCTGATCCCGGAGATC   5'
```

FIGURE 18 ated United States Patent documentation.

SEQUENCE LISTING

<160> NUMBER OF SEQ ID NOS: 120

<210> SEQ ID NO 1
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: HPCM2-hybridoma

<400> SEQUENCE: 1

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Tyr Tyr Gly Ser Ser Tyr Trp Tyr Phe Asp Val
            100                 105                 110

Trp Gly Ala Gly Thr Thr Val Thr Val Ser Ser
        115                 120

<210> SEQ ID NO 2
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: HPCM3-hybridoma

<400> SEQUENCE: 2

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
           35                  40                  45

Ala Ala Ser Arg Asn Lys Ala Asn Asp Tyr Thr Thr Glu Tyr Ser Ala
        50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Tyr Tyr Gly Ser Ser Tyr Trp Tyr Phe Asp Val
                100                 105                 110

Trp Gly Ala Gly Thr Thr Val Thr Val Ser Ser
            115                 120

<210> SEQ ID NO 3
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: HPCM1-hybridoma

<400> SEQUENCE: 3

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
           35                  40                  45

Ala Ala Ser Arg Asn Lys Ala Asn Asp Tyr Thr Thr Glu Tyr Ser Ala
        50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Tyr Tyr Gly Ser Ser Tyr Trp Tyr Phe Asp Val
                100                 105                 110

Trp Gly Ala Gly Thr Thr Val Thr Val Ser Ser
            115                 120

<210> SEQ ID NO 4
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: HPCM6-hybridoma

<400> SEQUENCE: 4

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
           35                  40                  45

Ala Ala Ser Arg Asn Lys Ala Asn Asp Tyr Thr Thr Glu Tyr Ser Ala
        50                  55                  60

Ser Val Lys Gly Arg Phe Ile Val Ser Arg Asp Thr Ser Gln Ser Ile

```
                65                  70                  75                  80
Leu Tyr Leu Gln Met Asn Ala Leu Arg Ala Glu Asp Thr Ala Ile Tyr
                    85                  90                  95

Tyr Cys Ala Arg Asp Tyr Tyr Asp Tyr Pro His Trp Tyr Phe Asp Val
            100                 105                 110

Trp Gly Ala Gly Thr Thr Val Thr Val Ser Ser
            115                 120

<210> SEQ ID NO 5
<211> LENGTH: 107
<212> TYPE: PRT
<213> ORGANISM: Mus musculus

<400> SEQUENCE: 5

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Phe
                85                  90                  95

Tyr Cys Ala Arg Asp Phe Tyr Arg Tyr Asp Gly
            100                 105

<210> SEQ ID NO 6
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: HPCG8-hybridoma

<400> SEQUENCE: 6

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Phe Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Tyr Tyr Gly Ser Arg Tyr Trp Tyr Phe Asp Val
            100                 105                 110

Trp Gly Ala Gly Thr Thr Val Thr Val Ser Ser
            115                 120

<210> SEQ ID NO 7
<211> LENGTH: 123
```

```
<212> TYPE: PRT
<213> ORGANISM: Mus musculus
<220> FEATURE:
<221> NAME/KEY: VARIANT
<222> LOCATION: (1)..(123)
<223> OTHER INFORMATION: HPCG13-hybridoma

<400> SEQUENCE: 7

Glu Val Lys Leu Val Glu Ser Gly Gly Gly Leu Val Gln Pro Gly Gly
1               5                   10                  15

Ser Leu Arg Leu Ser Cys Ala Leu Ser Gly Phe Leu Phe Ser Asp Phe
            20                  25                  30

Tyr Met Glu Trp Val Arg Gln Thr Pro Gly Lys Arg Leu Glu Trp Ile
        35                  40                  45

Ala Ala Ser Arg Asn Lys Val Tyr Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Ala Tyr Tyr Gly Ser Tyr Trp Tyr Phe Asp Val
            100                 105                 110

Trp Gly Ala Gly Thr Thr Val Thr Val Ser Ser
        115                 120

<210> SEQ ID NO 8
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: HPCG14-hybridoma

<400> SEQUENCE: 8

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Ala Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Phe Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Val Tyr Tyr Gly Tyr Asp Trp Tyr Phe Asp Val
            100                 105                 110

Trp Gly Ala Gly Thr Thr Val Thr Val Ser Ser
        115                 120

<210> SEQ ID NO 9
<211> LENGTH: 101
<212> TYPE: PRT
<213> ORGANISM: Mus musculus
<220> FEATURE:
<221> NAME/KEY: VARIANT
<222> LOCATION: (1)..(101)
<223> OTHER INFORMATION: HPCG11-hybridoma
```

```
<400> SEQUENCE: 9

Glu Val Lys Leu Val Glu Ser Gly Gly Gly Leu Val Gln Pro Gly Gly
1               5                   10                  15

Ser Leu Arg Leu Ser Cys Ala Thr Ser Gly Ile Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Ser Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp
            100

<210> SEQ ID NO 10
<211> LENGTH: 88
<212> TYPE: PRT
<213> ORGANISM: Mus musculus
<220> FEATURE:
<221> NAME/KEY: VARIANT
<222> LOCATION: (1)..(88)
<223> OTHER INFORMATION: HPCG12-hybridoma

<400> SEQUENCE: 10

Glu Val Lys Leu Val Glu Ser Gly Gly Gly Leu Val Gln Pro Gly Gly
1               5                   10                  15

Ser Leu Arg Leu Ser Cys Ala Thr Ser Gly Ile Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu
                85

<210> SEQ ID NO 11
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: T15-myeloma
<220> FEATURE:
<221> NAME/KEY: VARIANT
<222> LOCATION: (1)..(123)
<223> OTHER INFORMATION: T15-myeloma protein

<400> SEQUENCE: 11

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
```

```
                    50                  55                  60
Ser Val Lys Gly Arg Phe Ile Val Ser Arg Asp Thr Ser Gln Ser Ile
 65                  70                  75                  80

Leu Tyr Leu Gln Met Asn Ala Leu Arg Ala Glu Asp Thr Ala Ile Tyr
                     85                  90                  95

Tyr Cys Ala Arg Asp Tyr Tyr Gly Ser Ser Tyr Trp Tyr Phe Asp Val
                100                 105                 110

Trp Gly Ala Gly Thr Thr Val Thr Val Ser Ser
            115                 120
```

<210> SEQ ID NO 12
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: S63-myeloma protein

<400> SEQUENCE: 12

```
Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Ser Asp Phe
                20                  25                  30

Tyr Met Glu Trp Val Arg Gln Pro Pro Gly Lys Arg Leu Glu Trp Ile
             35                  40                  45

Ala Ala Ser Arg Asn Lys Ala Asn Asp Tyr Thr Thr Glu Tyr Ser Ala
         50                  55                  60

Ser Val Lys Gly Arg Phe Ile Val Ser Arg Asp Thr Ser Gln Ser Ile
 65                  70                  75                  80

Leu Tyr Leu Gln Met Asn Ala Leu Arg Ala Glu Asp Thr Ala Ile Tyr
                     85                  90                  95

Tyr Cys Ala Arg Asp Tyr Tyr Gly Ser Ser Tyr Trp Tyr Phe Asp Val
                100                 105                 110

Trp Gly Ala Gly Thr Thr Val Thr Val Ser Ser
            115                 120
```

<210> SEQ ID NO 13
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: Y5236-myeloma protein

<400> SEQUENCE: 13

```
Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Ser Asp Phe
                20                  25                  30

Tyr Met Glu Trp Val Arg Gln Pro Pro Gly Lys Arg Leu Glu Trp Ile
             35                  40                  45

Ala Ala Ser Arg Asn Lys Ala Asn Asp Tyr Thr Thr Glu Tyr Ser Ala
         50                  55                  60

Ser Val Lys Gly Arg Phe Ile Val Ser Arg Asp Thr Ser Gln Ser Ile
 65                  70                  75                  80

Leu Tyr Leu Gln Met Asn Ala Leu Arg Ala Glu Asp Thr Ala Ile Tyr
                     85                  90                  95
```

```
Tyr Cys Ala Arg Asp Tyr Tyr Gly Ser Ser Tyr Trp Tyr Phe Asp Val
            100                 105                 110

Trp Gly Ala Gly Thr Thr Val Thr Val Ser Ser
        115                 120

<210> SEQ ID NO 14
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: S107-myeloma protein

<400> SEQUENCE: 14

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Tyr Tyr Gly Ser Ser Tyr Trp Tyr Phe Asp Val
            100                 105                 110

Trp Gly Ala Gly Thr Thr Val Thr Val Ser Ser
        115                 120

<210> SEQ ID NO 15
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: H8-myeloma protein

<400> SEQUENCE: 15

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Tyr Tyr Gly Ser Asn Tyr Trp Tyr Phe Asp Val
            100                 105                 110

Trp Gly Ala Gly Thr Thr Val Thr Val Ser Ser
        115                 120
```

```
<210> SEQ ID NO 16
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: M603-myeloma protein

<400> SEQUENCE: 16

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Gly Asn Lys Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asn Tyr Tyr Gly Ser Thr Tyr Trp Tyr Phe Asp Val
            100                 105                 110

Trp Gly Ala Gly Thr Thr Val Thr Val Ser Ser
        115                 120

<210> SEQ ID NO 17
<211> LENGTH: 123
<212> TYPE: PRT
<213> ORGANISM: Mus musculus
<220> FEATURE:
<221> NAME/KEY: VARIANT
<222> LOCATION: (1)..(123)
<223> OTHER INFORMATION: W3207-myeloma protein

<400> SEQUENCE: 17

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Phe Gln Met Asn Ala Leu Arg Ala Glu Asp Thr Ala Ile Tyr
                85                  90                  95

Tyr Cys Ala Arg Asn Tyr Tyr Lys Tyr Asp Leu Trp Tyr Val Asp Val
            100                 105                 110

Trp Gly Ala Gly Thr Thr Val Thr Val Ser Ser
        115                 120

<210> SEQ ID NO 18
<211> LENGTH: 124
<212> TYPE: PRT
<213> ORGANISM: Mus musculus
<220> FEATURE:
<221> NAME/KEY: VARIANT
```

```
<222> LOCATION: (1)..(123)
<223> OTHER INFORMATION: M511-myeloma protein

<400> SEQUENCE: 18
```

| | | | | | | | | | | | | | | |
|---|---|---|---|---|---|---|---|---|---|---|---|---|---|---|
| Glu | Val | Lys | Leu | Val | Glu | Ser | Gly | Gly | Gly | Leu | Val | Gln | Pro | Gly | Gly |
| 1 | | | | 5 | | | | | 10 | | | | | 15 | |

Ser Leu Arg Leu Ser Cys Ala Thr Ser Gly Phe Thr Phe Ser Asp Phe
            20                  25                  30

Tyr Met Glu Trp Val Arg Gln Ser Pro Gly Lys Arg Leu Glu Trp Ile
         35                  40                  45

Ala Ala Ser Arg Asn Lys Ala Asn Asp Tyr Thr Thr Glu Tyr Ser Ala
 50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
             85                  90                  95

Tyr Cys Ala Arg Asp Gly Asp Tyr Gly Ser Ser Tyr Trp Tyr Phe Asp
            100                 105                 110

Val Trp Gly Ala Gly Thr Thr Val Thr Val Ser Ser
        115                 120

```
<210> SEQ ID NO 19
<211> LENGTH: 125
<212> TYPE: PRT
<213> ORGANISM: Mus musculus
<220> FEATURE:
<221> NAME/KEY: VARIANT
<222> LOCATION: (1)..(123)
<223> OTHER INFORMATION: M167-myeloma

<400> SEQUENCE: 19
```

Glu Val Val Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Thr Pro Gly Lys Arg Leu Glu Trp Ile
         35                  40                  45

Ala Ala Ser Arg Ser Lys Ala His Asp Tyr Thr Arg Glu Tyr Ser Ala
 50                  55                  60

Ser Val Lys Gly Arg Phe Ile Val Ser Arg Asp Thr Ser Gln Ser Val
65                  70                  75                  80

Leu Tyr Leu Gln Met Asn Ala Leu Arg Ala Glu Asp Thr Ala Thr Tyr
             85                  90                  95

Tyr Cys Thr Arg Asp Ala Asp Tyr Gly Asn Ser Tyr Phe Gly Tyr Phe
            100                 105                 110

Asp Val Trp Gly Ala Gly Thr Thr Val Thr Val Ser Ser
        115                 120                 125

```
<210> SEQ ID NO 20
<211> LENGTH: 110
<212> TYPE: DNA
<213> ORGANISM: Mus musculus

<400> SEQUENCE: 20
ctcgagtcag gacctggcct cgtgaaacct tctcagtctc tgtctctcac ctgctctgtc     60
actggctact ccatcaccag tgcttattac tggaactgga tccggcagtt              110

<210> SEQ ID NO 21
```

```
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A,T,C, or G

<400> SEQUENCE: 21
ctcgagtctg ggcctnaact ggcaaaacct ggggcctcag tgaagatgtc ctgcaaggct      60
tctggccaca ccttgactag ttactggata cactgggtaa aanagaggcc                110

<210> SEQ ID NO 22
<211> LENGTH: 110
<212> TYPE: DNA
<213> ORGANISM: Mus musculus
<220> FEATURE:
<221> NAME/KEY: misc_feature
<222> LOCATION: (1)..(108)
<223> OTHER INFORMATION: n=A, T, C or G
<220> FEATURE:
<221> NAME/KEY: misc_feature
<222> LOCATION: (1)..(110)
<223> OTHER INFORMATION: n=A, T, C or G

<400> SEQUENCE: 22
ctcgagtctg gacctnagct ggtaaagcct ggggttcagt gaagatgtcc tgcaaggctt      60
ctggatacac attcacnagc tatgttatac actgggtgaa gcagaagcct                110

<210> SEQ ID NO 23
<211> LENGTH: 110
<212> TYPE: DNA
<213> ORGANISM: Mus musculus

<400> SEQUENCE: 23
ctcgagtctg gacctgaact ggtaaagcct gggacttcag tgaagatgtc ctgcaaggct      60
tctggataca cattcaccag ctatgttatg cgctgggtga agcagaagcc                110

<210> SEQ ID NO 24
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A, T, C or G

<400> SEQUENCE: 24
ctcgagtcag gggctgaact ggtgaagcct ggggtttcag tgaagttgtc ctgcaaggct      60
tctggctaca ccttcacnag ctactatatg tactgggtga agcagaggcc                110

<210> SEQ ID NO 25
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A, T, C or G

<400> SEQUENCE: 25
ctcgagtctg gggctaagct ggtaaggcct ggagcttnag tnaagctgtc ctgnagggct      60
tctggctact ccttcacnag ctactggatg aactgggtga agcagaggcc                110
```

<210> SEQ ID NO 26
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n= A, T, C or G

<400> SEQUENCE: 26
ctcgagtctg gggctgagct ggtgaggcct ggagcttcag tnaagctgtc ctgcaaggcc    60
tctcgtactc cttcaccagc tcctgataac tgggtgaagc agaggcctgg              110

<210> SEQ ID NO 27
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A, T, C or G

<400> SEQUENCE: 27
ctcgagtcag gaggtggcct ggtgcagcct ggaggatccc tgaaactctc ctgtgcagcc    60
tcaggattcg atttnagnag atactggatg aattgggtcc ggcagctcca              110

<210> SEQ ID NO 28
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A, T, C or G

<400> SEQUENCE: 28
ctcgagtctg gaggtggcct ggtgcagcct ggaggatccc tgaatctccc ctgtgcagcc    60
tcaggattcg atttnagnag ataatggatg agttgggttc ggcaggctcc              110

<210> SEQ ID NO 29
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A, T, C or G

<400> SEQUENCE: 29
ctcgagtctg gaggtggcct ggtgcagcct ggaggatccc tgaaagtctc ctgtgcagcc    60
tcaggattcg atttnagnag atactggatg agttgggtcc ggcagctcca              110

<210> SEQ ID NO 30
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A, T, C or G

<400> SEQUENCE: 30
ctcgagtctg gaggtggcct ggtgcagcct ggaggatccc tcaaactctc ctgtgcagcc    60
tcaggattcg atttnagnag atactggatg agttgggtcc ggcagctcca              110

```
<210> SEQ ID NO 31
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A, T, C or G

<400> SEQUENCE: 31
ctcgagtcag gaggtggcct ggtgcagcct ggaggagccc tgaaactctc ctgtgcagcc        60
tcaggattcg atttnagnag atactggatg agttgggtcc gcagctccag                  110

<210> SEQ ID NO 32
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A, T, C or G

<400> SEQUENCE: 32
ctcgagtctg ggggaggctt agtncagcct ggagggtccc ggaaactctc ctgtgcagcc        60
tctggattca ctttnagnag ttttggaatg cactggattc gtcaggctcc                  110

<210> SEQ ID NO 33
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A, T, C or G

<400> SEQUENCE: 33
ctcgagtctg ggggaggctt agtnnagcct ggagggtccc ggaaactctc ctgtgcagcc        60
tctggattca ctttnagnag ctttggaatg cactgggtta cgtcaggctc                  110

<210> SEQ ID NO 34
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A, T, C or G

<400> SEQUENCE: 34
ctcgagtctg gggctgaact ggtgaggcct gggcgttcag tnaagatgtc ctgcaaggct        60
tcaggctatt ccttcaccag ctactggatg cactgggtga acagaggcc                   110

<210> SEQ ID NO 35
<211> LENGTH: 110
<212> TYPE: DNA
<213> ORGANISM: Mus musculus

<400> SEQUENCE: 35
ctcgagtcag gggctgaact ggcaaaacct ggggcctcag taaagatgtc ctgcaaggct        60
tctggctaca cctcttcttc cttctggctg cactggataa aagaaggcct                  110

<210> SEQ ID NO 36
<211> LENGTH: 110
```

<210> SEQ ID NO 36
<211> LENGTH: 110
<212> TYPE: DNA
<213> ORGANISM: Mus musculus
<220> FEATURE:
<221> NAME/KEY: misc_feature
<222> LOCATION: (1)..(110)
<223> OTHER INFORMATION: n=A, T, C or G

<400> SEQUENCE: 36

```
ctcgagtctg gacctnagct ggtgaagcct ggggttcagt taaaatatcc tgcaaggctt      60
ctggttactc attttctntc tactttgtga actgggtgat gcagagccat                 110
```

<210> SEQ ID NO 37
<211> LENGTH: 110
<212> TYPE: DNA
<213> ORGANISM: Mus musculus

<400> SEQUENCE: 37

```
ctcgagtcag gggctgaact ggtgaagcct ggggttcagt aagttgtcct gaaggcttct      60
ggctacacct tcaccggcta ctatatgtac tgggtgaagc agaggcctgg                 110
```

<210> SEQ ID NO 38
<211> LENGTH: 172
<212> TYPE: DNA
<213> ORGANISM: Unknown
<220> FEATURE:
<223> OTHER INFORMATION: Synthetic

<400> SEQUENCE: 38

```
ggccgcaaat tctatttcaa ggagacagtc ataatgaaat acctattgcc tacggcagcc      60
gctggattgt tattactcgc tgcccaacca gccatggccc aggtgaaact gctcgagatt     120
ctagactagt tacccgtacg acgttccgga ctacggttct aatagaattc g              172
```

<210> SEQ ID NO 39
<211> LENGTH: 136
<212> TYPE: DNA
<213> ORGANISM: Unknown
<220> FEATURE:
<223> OTHER INFORMATION: Synthetic

<400> SEQUENCE: 39

```
ggccgcaaat tctatttcaa ggagacagtc ataatgaaat acctattgcc tacggcagcc      60
gctggattgt tattactcgc tgcccaacca gccatggccc aggtgaaact gctcgagatt     120
ctagactagt taatag                                                     136
```

<210> SEQ ID NO 40
<211> LENGTH: 131
<212> TYPE: DNA
<213> ORGANISM: Unknown
<220> FEATURE:
<223> OTHER INFORMATION: Synthetic

<400> SEQUENCE: 40

```
tgaattctaa actagtcgcc aaggagacag tcataatgaa atacctattg cctacggcag      60
ccgctggatt gttattactc gctgcccaac cagccatggc cgagctcgtc agttctagag     120
ttaagcggcc g                                                          131
```

<210> SEQ ID NO 41
<211> LENGTH: 131
<212> TYPE: DNA
<213> ORGANISM: Unknown
<220> FEATURE:

<223> OTHER INFORMATION: Synthetic

<400> SEQUENCE: 41
tgaattctaa actagtcgcc aaggagacag tcataatgaa atacctattg cctacggcag    60
ccgctggatt gttattactc gctgcccaac cagccatggc cgagctcgtc agttctagag   120
ttaagcggcc g                                                        131

<210> SEQ ID NO 42
<211> LENGTH: 22
<212> TYPE: DNA
<213> ORGANISM: Unknown
<220> FEATURE:
<223> OTHER INFORMATION: Synthetic

<400> SEQUENCE: 42
aggtccagct gctcgagtct gg                                             22

<210> SEQ ID NO 43
<211> LENGTH: 22
<212> TYPE: DNA
<213> ORGANISM: Unknown
<220> FEATURE:
<223> OTHER INFORMATION: Synthetic

<400> SEQUENCE: 43
aggtccagct gctcgagtca gg                                             22

<210> SEQ ID NO 44
<211> LENGTH: 22
<212> TYPE: DNA
<213> ORGANISM: Unknown
<220> FEATURE:
<223> OTHER INFORMATION: Synthetic

<400> SEQUENCE: 44
aggtccagct tctcgagtct gg                                             22

<210> SEQ ID NO 45
<211> LENGTH: 22
<212> TYPE: DNA
<213> ORGANISM: Unknown
<220> FEATURE:
<223> OTHER INFORMATION: Synthetic

<400> SEQUENCE: 45
aggtccagct tctcgagtca gg                                             22

<210> SEQ ID NO 46
<211> LENGTH: 22
<212> TYPE: DNA
<213> ORGANISM: Unknown
<220> FEATURE:
<223> OTHER INFORMATION: Synthetic

<400> SEQUENCE: 46
aggtccaact gctcgagtct gg                                             22

<210> SEQ ID NO 47
<211> LENGTH: 22
<212> TYPE: DNA
<213> ORGANISM: Unknown
<220> FEATURE:
<223> OTHER INFORMATION: Synthetic

<400> SEQUENCE: 47
aggtccaact gctcgagtca gg                                              22

<210> SEQ ID NO 48
<211> LENGTH: 22
<212> TYPE: DNA
<213> ORGANISM: Unknown
<220> FEATURE:
<223> OTHER INFORMATION: Synthetic

<400> SEQUENCE: 48
aggtccaact tctcgagtct gg                                              22

<210> SEQ ID NO 49
<211> LENGTH: 22
<212> TYPE: DNA
<213> ORGANISM: Unknown
<220> FEATURE:
<223> OTHER INFORMATION: Synthetic

<400> SEQUENCE: 49
aggtccaact tctcgagtca gg                                              22

<210> SEQ ID NO 50
<211> LENGTH: 20
<212> TYPE: DNA
<213> ORGANISM: Unknown
<220> FEATURE:
<223> OTHER INFORMATION: 5' degenerate primer contaning inosine at 4
      degenerate positions
<220> FEATURE:
<221> NAME/KEY: misc_feature
<222> LOCATION: (1)..(20)
<223> OTHER INFORMATION: n=inosine

<400> SEQUENCE: 50
aggtnnanct nctcgagtct                                                 20

<210> SEQ ID NO 51
<211> LENGTH: 20
<212> TYPE: DNA
<213> ORGANISM: Unknown
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n=inosine

<400> SEQUENCE: 51
aggtnnanct nctcgagtca                                                 20

<210> SEQ ID NO 52
<211> LENGTH: 19
<212> TYPE: DNA
<213> ORGANISM: Unknown
<220> FEATURE:
<223> OTHER INFORMATION: Synthetic

<400> SEQUENCE: 52
gcccaaggat gtgctcacc                                                  19

<210> SEQ ID NO 53
<211> LENGTH: 39
<212> TYPE: DNA
<213> ORGANISM: Unknown
<220> FEATURE:
<223> OTHER INFORMATION: Synthetic

<400> SEQUENCE: 53
ctattagaat tcaacggtaa cagtggtgcc ttggcccca            39

<210> SEQ ID NO 54
<211> LENGTH: 39
<212> TYPE: DNA
<213> ORGANISM: Unknown
<220> FEATURE:
<223> OTHER INFORMATION: Synthetic

<400> SEQUENCE: 54
ctattaacta gtaacggtaa cagtggtgcc ttggcccca            39

<210> SEQ ID NO 55
<211> LENGTH: 19
<212> TYPE: DNA
<213> ORGANISM: Unknown
<220> FEATURE:
<223> OTHER INFORMATION: Synthetic

<400> SEQUENCE: 55
ctcagtatgg tggttgtgc                                  19

<210> SEQ ID NO 56
<211> LENGTH: 26
<212> TYPE: DNA
<213> ORGANISM: Unknown
<220> FEATURE:
<223> OTHER INFORMATION: Synthetic

<400> SEQUENCE: 56
gctactagtt ttgatttcca ccttgg                          26

<210> SEQ ID NO 57
<211> LENGTH: 23
<212> TYPE: DNA
<213> ORGANISM: Unknown
<220> FEATURE:
<223> OTHER INFORMATION: Synthetic

<400> SEQUENCE: 57
cagccatggc cgacatccag atg                             23

<210> SEQ ID NO 58
<211> LENGTH: 30
<212> TYPE: DNA
<213> ORGANISM: Unknown
<220> FEATURE:
<223> OTHER INFORMATION: Synthetic

<400> SEQUENCE: 58
aattttacta gtcaccttgg tgctgctggc                      30

<210> SEQ ID NO 59
<211> LENGTH: 39
<212> TYPE: DNA
<213> ORGANISM: Unknown
<220> FEATURE:
<223> OTHER INFORMATION: Synthetic

<400> SEQUENCE: 59
tatgcaacta gtacaaccac aatccctggg cacaattttt           39

<210> SEQ ID NO 60

```
<211> LENGTH: 32
<212> TYPE: DNA
<213> ORGANISM: Unknown
<220> FEATURE:
<223> OTHER INFORMATION: Synthetic

<400> SEQUENCE: 60
ccagttccga gctcgttgtg actcaggaat ct                                 32

<210> SEQ ID NO 61
<211> LENGTH: 32
<212> TYPE: DNA
<213> ORGANISM: Unknown
<220> FEATURE:
<223> OTHER INFORMATION: Synthetic

<400> SEQUENCE: 61
ccagttccga gctcgtgttg acgcagccgc cc                                 32

<210> SEQ ID NO 62
<211> LENGTH: 32
<212> TYPE: DNA
<213> ORGANISM: Unknown
<220> FEATURE:
<223> OTHER INFORMATION: Synthetic

<400> SEQUENCE: 62
ccagttccga gctcgtgctc acccagtctc ca                                 32

<210> SEQ ID NO 63
<211> LENGTH: 32
<212> TYPE: DNA
<213> ORGANISM: Unknown
<220> FEATURE:
<223> OTHER INFORMATION: Synthetic

<400> SEQUENCE: 63
ccagttccga gctccagatg acccagtctc ca                                 32

<210> SEQ ID NO 64
<211> LENGTH: 32
<212> TYPE: DNA
<213> ORGANISM: Unknown
<220> FEATURE:
<223> OTHER INFORMATION: Synthetic

<400> SEQUENCE: 64
ccagatgtga gctcgtgatg acccagactc ca                                 32

<210> SEQ ID NO 65
<211> LENGTH: 32
<212> TYPE: DNA
<213> ORGANISM: Unknown
<220> FEATURE:
<223> OTHER INFORMATION: Synthetic

<400> SEQUENCE: 65
ccagatgtga gctcgtcatg acccagtctc ca                                 32

<210> SEQ ID NO 66
<211> LENGTH: 32
<212> TYPE: DNA
<213> ORGANISM: Unknown
<220> FEATURE:
<223> OTHER INFORMATION: Synthetic

<400> SEQUENCE: 66
```
ccagatgtga gctcgtgata acccaggatg aa        32

<210> SEQ ID NO 67
<211> LENGTH: 32
<212> TYPE: DNA
<213> ORGANISM: Unknown
<220> FEATURE:
<223> OTHER INFORMATION: Synthetic

<400> SEQUENCE: 67
gcagcattct agagtttcag ctccagcttg cc        32

<210> SEQ ID NO 68
<211> LENGTH: 33
<212> TYPE: DNA
<213> ORGANISM: Unknown
<220> FEATURE:
<223> OTHER INFORMATION: Synthetic

<400> SEQUENCE: 68
ccgccgtcta gaacactcat tcctgttgaa gct       33

<210> SEQ ID NO 69
<211> LENGTH: 33
<212> TYPE: DNA
<213> ORGANISM: Unknown
<220> FEATURE:
<223> OTHER INFORMATION: Synthetic

<400> SEQUENCE: 69
ccgccgtcta gaacattctg caggagacag act       33

<210> SEQ ID NO 70
<211> LENGTH: 32
<212> TYPE: DNA
<213> ORGANISM: Unknown
<220> FEATURE:
<223> OTHER INFORMATION: Synthetic

<400> SEQUENCE: 70
ccagttccga gctcgtgatg acacagtctc ca        32

<210> SEQ ID NO 71
<211> LENGTH: 34
<212> TYPE: DNA
<213> ORGANISM: Unknown
<220> FEATURE:
<223> OTHER INFORMATION: Synthetic

<400> SEQUENCE: 71
gcgccgtcta gaattaacac tcattcctgt tgaa      34

<210> SEQ ID NO 72
<211> LENGTH: 38
<212> TYPE: DNA
<213> ORGANISM: Unknown
<220> FEATURE:
<223> OTHER INFORMATION: Synthetic

<400> SEQUENCE: 72
ctattaacta gtaacggtaa cagtggtgcc ttgcccca  38

<210> SEQ ID NO 73
<211> LENGTH: 30
<212> TYPE: DNA

<213> ORGANISM: Unknown
<220> FEATURE:
<223> OTHER INFORMATION: Synthetic

<400> SEQUENCE: 73
aggcttacta gtacaatccc tgggcacaat 30

<210> SEQ ID NO 74
<211> LENGTH: 29
<212> TYPE: DNA
<213> ORGANISM: Unknown
<220> FEATURE:
<223> OTHER INFORMATION: Synthetic

<400> SEQUENCE: 74
gccgctctag aacactcatt cctgttgaa 29

<210> SEQ ID NO 75
<211> LENGTH: 22
<212> TYPE: DNA
<213> ORGANISM: Unknown
<220> FEATURE:
<223> OTHER INFORMATION: Synthetic
<220> FEATURE:
<221> NAME/KEY: misc_feature
<222> LOCATION: (1)..(22)
<223> OTHER INFORMATION: n=inosine

<400> SEQUENCE: 75
aggtnnanct nctcgagtct gc 22

<210> SEQ ID NO 76
<211> LENGTH: 22
<212> TYPE: DNA
<213> ORGANISM: Unknown
<220> FEATURE:
<223> OTHER INFORMATION: Synthetic
<220> FEATURE:
<221> NAME/KEY: misc_feature
<222> LOCATION: (1)..(22)
<223> OTHER INFORMATION: n=inosine

<400> SEQUENCE: 76
aggtnnanct nctcgagtca gc 22

<210> SEQ ID NO 77
<211> LENGTH: 35
<212> TYPE: DNA
<213> ORGANISM: Unknown
<220> FEATURE:
<223> OTHER INFORMATION: Synthetic

<400> SEQUENCE: 77
gtgccagatg tgagctcgtg atgacccagt ctcca 35

<210> SEQ ID NO 78
<211> LENGTH: 34
<212> TYPE: DNA
<213> ORGANISM: Unknown
<220> FEATURE:
<223> OTHER INFORMATION: Synthetic

<400> SEQUENCE: 78
tccttctaga ttactaacac tctcccctgt tgaa 34

<210> SEQ ID NO 79
<211> LENGTH: 31

```
<212> TYPE: DNA
<213> ORGANISM: Unknown
<220> FEATURE:
<223> OTHER INFORMATION: Synthetic

<400> SEQUENCE: 79
gcattctaga ctattaacat tctgtagggg c                                    31

<210> SEQ ID NO 80
<211> LENGTH: 37
<212> TYPE: DNA
<213> ORGANISM: Unknown
<220> FEATURE:
<223> OTHER INFORMATION: Synthetic

<400> SEQUENCE: 80
ctgcacaggg tcctgggccg agctcgtggt gactcag                              37

<210> SEQ ID NO 81
<211> LENGTH: 22
<212> TYPE: DNA
<213> ORGANISM: Unknown
<220> FEATURE:
<223> OTHER INFORMATION: Synthetic
<220> FEATURE:
<221> NAME/KEY: misc_feature
<222> LOCATION: (1)..(22)
<223> OTHER INFORMATION: n=inosine

<400> SEQUENCE: 81
agntgcannt gctcgagtct gg                                              22

<210> SEQ ID NO 82
<211> LENGTH: 43
<212> TYPE: DNA
<213> ORGANISM: Unknown
<220> FEATURE:
<223> OTHER INFORMATION: Synthetic

<400> SEQUENCE: 82
gtgggcatgt gtgagttgtg tcactagttg gggttttgag ctc                       43

<210> SEQ ID NO 83
<211> LENGTH: 30
<212> TYPE: DNA
<213> ORGANISM: Unknown
<220> FEATURE:
<223> OTHER INFORMATION: Synthetic

<400> SEQUENCE: 83
cggactagta caagatttgg gctctgcttt                                      30

<210> SEQ ID NO 84
<211> LENGTH: 22
<212> TYPE: DNA
<213> ORGANISM: Unknown
<220> FEATURE:
<223> OTHER INFORMATION: Synthetic
<220> FEATURE:
<221> NAME/KEY: misc_feature
<222> LOCATION: (1)..(22)
<223> OTHER INFORMATION: s=C or G, m= C or A, r= G or T, k= G or T, w= T
      or A

<400> SEQUENCE: 84
aggtsmarct kctcgagtcw gg                                              22
```

```
<210> SEQ ID NO 85
<211> LENGTH: 32
<212> TYPE: DNA
<213> ORGANISM: Unknown
<220> FEATURE:
<223> OTHER INFORMATION: Synthetic

<400> SEQUENCE: 85
ggccgcaaat tctatttcaa ggagacagtc at                              32

<210> SEQ ID NO 86
<211> LENGTH: 36
<212> TYPE: DNA
<213> ORGANISM: Unknown
<220> FEATURE:
<223> OTHER INFORMATION: Synthetic

<400> SEQUENCE: 86
aatgaaatac ctattgccta cggcagccgc tggatt                          36

<210> SEQ ID NO 87
<211> LENGTH: 31
<212> TYPE: DNA
<213> ORGANISM: Unknown
<220> FEATURE:
<223> OTHER INFORMATION: Synthetic

<400> SEQUENCE: 87
gttattactc gctgcccaac cagccatggc c                               31

<210> SEQ ID NO 88
<211> LENGTH: 38
<212> TYPE: DNA
<213> ORGANISM: Unknown
<220> FEATURE:
<223> OTHER INFORMATION: Synthetic

<400> SEQUENCE: 88
aggtgaaact gctcgagaat tctagactag gttaatag                        38

<210> SEQ ID NO 89
<211> LENGTH: 30
<212> TYPE: DNA
<213> ORGANISM: Unknown
<220> FEATURE:
<223> OTHER INFORMATION: Synthetic

<400> SEQUENCE: 89
tcgactatta actagtctag aattctcgag                                 30

<210> SEQ ID NO 90
<211> LENGTH: 29
<212> TYPE: DNA
<213> ORGANISM: Unknown
<220> FEATURE:
<223> OTHER INFORMATION: Synthetic

<400> SEQUENCE: 90
cagtttcacc tgggccatgg ctggttggg                                  29

<210> SEQ ID NO 91
<211> LENGTH: 40
<212> TYPE: DNA
<213> ORGANISM: Unknown
<220> FEATURE:
<223> OTHER INFORMATION: Synthetic
```

```
<400> SEQUENCE: 91
cagcgagtaa taacaatcca gcggctgccg taggcaatag                             40

<210> SEQ ID NO 92
<211> LENGTH: 38
<212> TYPE: DNA
<213> ORGANISM: Unknown
<220> FEATURE:
<223> OTHER INFORMATION: Synthetic

<400> SEQUENCE: 92
gtatttcatt atgactgtct ccttgaaata gaatttgc                               38

<210> SEQ ID NO 93
<211> LENGTH: 40
<212> TYPE: DNA
<213> ORGANISM: Unknown
<220> FEATURE:
<223> OTHER INFORMATION: Synthetic

<400> SEQUENCE: 93
aggtgaaact gctcgagatt tctagactag ttacccgtac                             40

<210> SEQ ID NO 94
<211> LENGTH: 33
<212> TYPE: DNA
<213> ORGANISM: Unknown
<220> FEATURE:
<223> OTHER INFORMATION: Synthetic

<400> SEQUENCE: 94
gacgttccgg actacggttc ttaatagaat tcg                                    33

<210> SEQ ID NO 95
<211> LENGTH: 28
<212> TYPE: DNA
<213> ORGANISM: Unknown
<220> FEATURE:
<223> OTHER INFORMATION: Synthetic

<400> SEQUENCE: 95
tcgacgaatt ctattaagaa ccgtagtc                                          28

<210> SEQ ID NO 96
<211> LENGTH: 38
<212> TYPE: DNA
<213> ORGANISM: Unknown
<220> FEATURE:
<223> OTHER INFORMATION: Synthetic

<400> SEQUENCE: 96
cggaacgtcg tacgggtaac tagtctagaa atctcgag                               38

<210> SEQ ID NO 97
<211> LENGTH: 34
<212> TYPE: DNA
<213> ORGANISM: Unknown
<220> FEATURE:
<223> OTHER INFORMATION: Synthetic

<400> SEQUENCE: 97
tgaattctaa actagtcgcc aaggagacag tcat                                   34

<210> SEQ ID NO 98
<211> LENGTH: 30
```

<210> SEQ ID NO 99
<211> LENGTH: 48
<212> TYPE: DNA
<213> ORGANISM: Unknown
<220> FEATURE:
<223> OTHER INFORMATION: Synthetic

<400> SEQUENCE: 98
gagctcgtca gttctagagt taagcggccg                                      30

<210> SEQ ID NO 99
<211> LENGTH: 48
<212> TYPE: DNA
<213> ORGANISM: Unknown
<220> FEATURE:
<223> OTHER INFORMATION: Synthetic

<400> SEQUENCE: 99
gtatttcatt atgactgtct ccttggcgac tagtttagaa ttcaagct                  48

<210> SEQ ID NO 100
<211> LENGTH: 40
<212> TYPE: DNA
<213> ORGANISM: Unknown
<220> FEATURE:
<223> OTHER INFORMATION: Synthetic

<400> SEQUENCE: 100
cagcgagtaa taacaatcca gcggctgccg taggcaatag                           40

<210> SEQ ID NO 101
<211> LENGTH: 27
<212> TYPE: DNA
<213> ORGANISM: Unknown
<220> FEATURE:
<223> OTHER INFORMATION: Synthetic

<400> SEQUENCE: 101
tgacgagctc ggccatggct ggttggg                                         27

<210> SEQ ID NO 102
<211> LENGTH: 24
<212> TYPE: DNA
<213> ORGANISM: Unknown
<220> FEATURE:
<223> OTHER INFORMATION: Synthetic

<400> SEQUENCE: 102
tcgacggccg cttaactcta gaac                                            24

<210> SEQ ID NO 103
<211> LENGTH: 28
<212> TYPE: DNA
<213> ORGANISM: Unknown
<220> FEATURE:
<223> OTHER INFORMATION: Synthetic

<400> SEQUENCE: 103
aataagcttg atctatcagt aatcgacc                                        28

<210> SEQ ID NO 104
<211> LENGTH: 31
<212> TYPE: DNA
<213> ORGANISM: Unknown
<220> FEATURE:
<223> OTHER INFORMATION: Synthetic

<400> SEQUENCE: 104
attagatctg aattctgacg tccgttatca g					31

<210> SEQ ID NO 105
<211> LENGTH: 56
<212> TYPE: DNA
<213> ORGANISM: Unknown
<220> FEATURE:
<223> OTHER INFORMATION: Synthetic

<400> SEQUENCE: 105
gatccgcttc ccgataaggg agcaggccag taaaagcatt acctgtggtg gggttc					56

<210> SEQ ID NO 106
<211> LENGTH: 51
<212> TYPE: DNA
<213> ORGANISM: Unknown
<220> FEATURE:
<223> OTHER INFORMATION: Synthetic

<400> SEQUENCE: 106
ccgagcggcc aaagggagca gactctaaat ctgccgtcat cgacttcgaa g					51

<210> SEQ ID NO 107
<211> LENGTH: 42
<212> TYPE: DNA
<213> ORGANISM: Unknown
<220> FEATURE:
<223> OTHER INFORMATION: Synthetic

<400> SEQUENCE: 107
gttcgaatcc ttcccccacc accatcactt tcaaaagtcc ga					42

<210> SEQ ID NO 108
<211> LENGTH: 56
<212> TYPE: DNA
<213> ORGANISM: Unknown
<220> FEATURE:
<223> OTHER INFORMATION: Synthetic

<400> SEQUENCE: 108
ctagtcggac ttttgaaagt gatggtggtg ggggaaggat tcgaaccttc gaagtc					56

<210> SEQ ID NO 109
<211> LENGTH: 52
<212> TYPE: DNA
<213> ORGANISM: Unknown
<220> FEATURE:
<223> OTHER INFORMATION: Synthetic
<220> FEATURE:
<221> NAME/KEY: misc_feature
<222> LOCATION: (1)..(52)
<223> OTHER INFORMATION: r= G or A

<400> SEQUENCE: 109
gatgacggca gatttagagt ctgctccctr ttggccgctc gggaacccca cc					52

<210> SEQ ID NO 110
<211> LENGTH: 42
<212> TYPE: DNA
<213> ORGANISM: Unknown
<220> FEATURE:
<223> OTHER INFORMATION: Synthetic

<400> SEQUENCE: 110
acaggtaatg cttttactgg cctgctccct tatcgggaag cg					42

```
<210> SEQ ID NO 111
<211> LENGTH: 9
<212> TYPE: DNA
<213> ORGANISM: Unknown
<220> FEATURE:
<223> OTHER INFORMATION: Synthetic

<400> SEQUENCE: 111 tcgagcgcc                                                                   9

<210> SEQ ID NO 112
<211> LENGTH: 9
<212> TYPE: DNA
<213> ORGANISM: Unknown
<220> FEATURE:
<223> OTHER INFORMATION: Synthetic

<400> SEQUENCE: 112 gatcggcgc                                                                   9

<210> SEQ ID NO 113
<211> LENGTH: 9
<212> TYPE: DNA
<213> ORGANISM: Unknown
<220> FEATURE:
<223> OTHER INFORMATION: Synthetic

<400> SEQUENCE: 113 ctagggcct                                                                   9

<210> SEQ ID NO 114
<211> LENGTH: 9
<212> TYPE: DNA
<213> ORGANISM: Unknown
<220> FEATURE:
<223> OTHER INFORMATION: Synthetic

<400> SEQUENCE: 114 ctagaggcc                                                                   9

<210> SEQ ID NO 115
<211> LENGTH: 5
<212> TYPE: DNA
<213> ORGANISM: Unknown
<220> FEATURE:
<223> OTHER INFORMATION: Synthetic

<400> SEQUENCE: 115 cgccc                                                                       5

<210> SEQ ID NO 116
<211> LENGTH: 13
<212> TYPE: DNA
<213> ORGANISM: Unknown
<220> FEATURE:
<223> OTHER INFORMATION: Synthetic

<400> SEQUENCE: 116
gatcgggcga gct                                                             13

<210> SEQ ID NO 117
<211> LENGTH: 41
<212> TYPE: DNA
<213> ORGANISM: Unknown
<220> FEATURE:
<223> OTHER INFORMATION: Synthetic
```

```
<400> SEQUENCE: 117
ctagttaccc gtacgacgtt ccggactacg cttcttaata g                    41

<210> SEQ ID NO 118
<211> LENGTH: 40
<212> TYPE: DNA
<213> ORGANISM: Unknown
<220> FEATURE:
<223> OTHER INFORMATION: Synthetic

<400> SEQUENCE: 118
aattctatta agaagcgtag tccggaacgt cgacgggtaa                      40

<210> SEQ ID NO 119
<211> LENGTH: 199
<212> TYPE: DNA
<213> ORGANISM: Unknown
<220> FEATURE:
<223> OTHER INFORMATION: Synthetic

<400> SEQUENCE: 119
tcgagcgccg atccgcttcc cgataaggga gcaggccagt aaaagcatta cctgtggtgg    60
ggttcccgag cggccaaagg gagcagactc taaatctgcc gtcatcgact tcgaaggttc   120
gaatccttcc cccaccacca tcactttcaa aagtccgact agttaccgt acgacgttcc    180 ggactacgct tcttaatag                                                199

<210> SEQ ID NO 120
<211> LENGTH: 162
<212> TYPE: DNA
<213> ORGANISM: Unknown
<220> FEATURE:
<223> OTHER INFORMATION: Synthetic

<400> SEQUENCE: 120
cgcccgatcc gcttcccgat aagggagcag gccagtaaaa gcattacctg tggtggggtt    60
cccagcggcc aaagggagca gactctaaat ctgccgtcat cgacttcgaa ggttcgaatc   120
cttcccccac caccatcact ttcaaaagtc gactagggc ct                       162
```

METHOD FOR TAPPING THE IMMUNOLOGICAL REPERTOIRE

CROSS REFERENCE TO RELATED APPLICATION

This application is a divisional of U.S. application Ser. No. 09/726,649, filed Nov. 28, 2000 now U.S. Pat. No. 6,969,586, which is a division of U.S. application Ser. No. 07/941,762, filed Sep. 4, 1992, now U.S. Pat. No. 6,291,161, which is a continuation of U.S. application Ser. No. 07/809,083, filed Dec. 9, 1991, now abandoned which is a continuation of U.S. application Ser. No. 07/446,332, filed Dec. 4, 1989, now abandoned which is a continuation-in-part application of U.S. application Ser. No. 07/353,241, filed May 17, 1989, now abandoned and a continuation-in-part of U.S. application Ser. No. 07/353,235, filed May 16, 1989, now abandoned the disclosures of which are hereby incorporated by reference.

TECHNICAL FIELD

The present invention relates to a method for isolating a gene coding for a receptor having a preselected activity.

BACKGROUND

The immune system of a mammal is one of the most versatile biological systems as probably greater than $1.0 \times 10^7$ antibody specificities can be produced. Indeed, much of contemporary biological and medical research is directed toward tapping this repertoire. During the last decade there has been a dramatic increase in the ability to harness the output of the vast immunological repertoire. The development of the hybridoma methodology by Kohler and Milstein has made it possible to produce monoclonal antibodies, i.e., a composition of antibody molecules of a single specificity, from the repertoire of antibodies induced during an immune response.

Unfortunately, current methods for generating monoclonal antibodies are not capable of efficiently surveying the entire antibody response induced by a particular immunogen. In an individual animal there are at least 5–10,000 different B-cell clones capable of generating unique antibodies to a small relatively rigid immunogens, such as, for example dinitrophenol. Further, because of the process of somatic mutation during the generation of antibody diversity, essentially an unlimited number of unique antibody molecules may be generated. In contrast to this vast potential for different antibodies, current hybridoma methodologies typically yield only a few hundred different monoclonal antibodies per fusion.

Other difficulties in producing monoclonal antibodies with the hybridoma methodology include genetic instability and low production capacity of hybridoma cultures. One means by which the art has attempted to overcome these latter two problems has been to clone the immunoglobulin-producing genes from a particular hybridoma of interest into a procaryotic expression system. See, for example, Robinson et al., PCT Publication No. WO 89/0099; Winter et al., European Patent Publication No. 0239400; Reading, U.S. Pat. No. 4,714,681; and Cabilly et al., European Patent Publication No. 0125023.

The immunologic repertoire of vertebrates has recently been found to contain genes coding for immunoglobulins having catalytic activity. Tramontano et al., Sci., 234:1566–1570 (1986); Pollack et al., Sci., 234:1570–1573 (1986); Janda et al., Sci., 241:1188–1191 (1988); and Janda et al., Sci., 244:437–440 (1989). The presence of, or the ability to induce the repertoire to produce, antibodies molecules capable of a catalyzing chemical reaction, i.e., acting like enzymes, had previously been postulated almost 20 years ago by W. P. Jencks in Catalysis in Chemistry and Enzymology, McGraw-Hill, N.Y. (1969).

It is believed that one reason the art failed to isolate catalytic antibodies from the immunological repertoire earlier, and its failure to isolate many to date even after their actual discovery, is the inability to screen a large portion of the repertoire for the desired activity. Another reason is believed to be the bias of currently available screening techniques, such as the hybridoma technique, towards the production high affinity antibodies inherently designed for participation in the process of neutralization, as opposed to catalysis.

BRIEF SUMMARY OF THE INVENTION

The present invention provides a novel method for screening a larger portion of the immunological repertoire for receptors having a preselected activity than has heretofore been possible, thereby overcoming the before-mentioned inadequacies of the hybridoma technique.

In one embodiment, an immunoglobulin heavy chain variable region $V_H$ gene library containing a substantial portion of the $V_H$ gene repertoire of a vertebrate is synthesized. In preferred embodiments, the $V_H$-coding gene library contains at least about $10^3$, preferably at least about $10^4$ and more preferably at least about $10^5$ different $V_H$-coding nucleic acid strands referred to herein as $V_H$-coding DNA homologs.

The gene library can be synthesized by either of two methods, depending on the starting material.

Where the starting material is a plurality of $V_H$-coding genes, the repertoire is subjected to two distinct primer extension reactions. The first primer extension reaction uses a first polynucleotide synthesis primer capable of initiating the first reaction by hybridizing to a nucleotide sequence conserved (shared by a plurality of genes) within the repertoire. The first primer extension reaction produces a plurality of different $V_H$-coding homolog complements (nucleic acid strands complementary to the genes in the repertoire).

The second primer extension reaction produces, using the complements as templates, a plurality of different $V_H$-coding DNA homologs. The second primer extension reaction uses a second polynucleotide synthesis primer that is capable of initiating the second reaction by hybridizing to a nucleotide sequence conserved among a plurality of $V_H$-coding gene complements.

Where the starting material is a plurality of complements of different $V_H$-coding genes provided by a method other than the first primer extension reaction, the repertoire is subjected to the above-discussed second primer extension reaction. That is, where the starting material is a plurality of different $V_H$-coding gene complements produced by a method such as denaturation of double strand genomic DNA, chemical synthesis and the like, the complements are subjected to a primer extension reaction using a polynucleotide synthesis primer that hybridizes to a plurality of the different $V_H$-coding gene complements provided. Of course, if both a repertoire of $V_H$-coding genes and their complements are present in the starting material, both approaches can be used in combination.

A $V_H$-coding DNA homolog, i.e., a gene coding for a receptor capable of binding the preselected ligand, is then segregated from the library to produce the isolated gene. This is typically accomplished by operatively linking for expression a plurality of the different $V_H$-coding DNA homologs of the library to an expression vector. The $V_H$-expression vectors so produced are introduced into a population of compatible host cells, i.e., cells capable of expressing a gene operatively linked for expression to the vector. The transformants are cultured under conditions for expressing the receptor coded for by the $V_H$-coding DNA homolog. The transformants are cloned and the clones are screened for expression of a receptor that binds the preselected ligand. Any of the suitable methods well known in the art for detecting the binding of a ligand to a receptor can be used. A transformant expressing the desired activity is then segregated from the population to produce the isolated gene.

In another embodiment, the present invention contemplates a gene library comprising an isolated admixture of at least about $10^3$, preferably at least about $10^4$ and more preferably at least $10 \, V_H$- and/or $V_L$-coding DNA homologs, a plurality of which share a conserved antigenic determinant. Preferably, the homologs are present in a medium suitable for in vitro manipulation, such as water, phosphate buffered saline and the like, which maintains the biological activity of the homologs.

A receptor having a preselected activity, preferably catalytic activity, produced by a method of the present invention, preferably a $V_H$ or $F_v$ as described herein, is also contemplated.

BRIEF DESCRIPTION OF THE DRAWINGS

In the drawings forming a portion of this disclosure:

FIG. 5 Nucleotide sequences are clones from the cDNA library of the PCR amplified $V_H$ regions in Lambda ZAP. The N-terminal 110 bases are listed here and the underlined nucleotides represent CDR1 (complementary determining region) (SEQ ID NOS:20–37).

FIG. 6 The sequence of the synthetic DNA insert inserted into Lambda ZAP to produce Lambda Zap II $V_H$ (Panel A (SEQ ID NO:38)) and Lambda Zap $V_L$ (Panel B (SEQ ID NO:39)) expression vectors. The various features required for this vector to express the $V_H$ and $V_L$-coding DNA homologs include the Shine-Dalgarno ribosome binding site, a leader sequence to direct the expressed protein to the periplasm as described by Mouva et al., J. Biol. Chem., 255:27, 1980, and various restriction enzyme sites used to operatively link the $V_H$ and $V_L$ homologs to the expression vector. The $V_H$ expression-vector sequence also contains a short nucleic acid sequence that codes for amino acids typically found in variable regions heavy chain ($V_H$ Backbone). This $V_H$ Backbone is just upstream and in the proper reading as the $V_H$ DNA homologs that are operatively linked into the Xho I and Spe I. The $V_L$ DNA homologs are operatively linked into the $V_L$ sequence (Panel B) at the Nco I and Spe I restriction enzyme sites and thus the $V_H$ Backbone region is deleted when the $V_L$ DNA homologs are operatively linked into the $V_L$ vector.

GATTTGATCAGCGGTTCCTCTGTCAGTATTACTTATACCTATTGCCTACG

GCAGCCGCTGGATTGTTATTACTCGCTGTATGGATAACGGATGCCGTCGG

CGACCTAACAATAATGAGCGACCCCAACCAGCCATGGCCGAGCTCGTCAG

TTCTAGAGTTAAGCGGCCGGGGTTGGTCGGTACCGGCTCGAGCAGTCAAG

ATCTCAATTCGCCGGC

AGCT into Lambda Zap II that has been digested with the restriction enzymes Sac I and Xho I. This sequence contains the Shine-Dalgarno sequence (Ribosome binding site), the leader sequence to direct the expressed protein to the periplasm and the appropriate nucleic acid sequence to allow the $V_L$ DNA homologs to be operatively linked into the SacI and Xba I restriction enzyme sites provided by this vector.

FIG. 10 The sequence of the synthetic DNA segment inserted into Lambda Zap II to produce the lambda $V_L$II-expression vector (SEQ ID NO:41). The various features and restriction endonuclease recognition sites are shown.

Figures 3, 11:
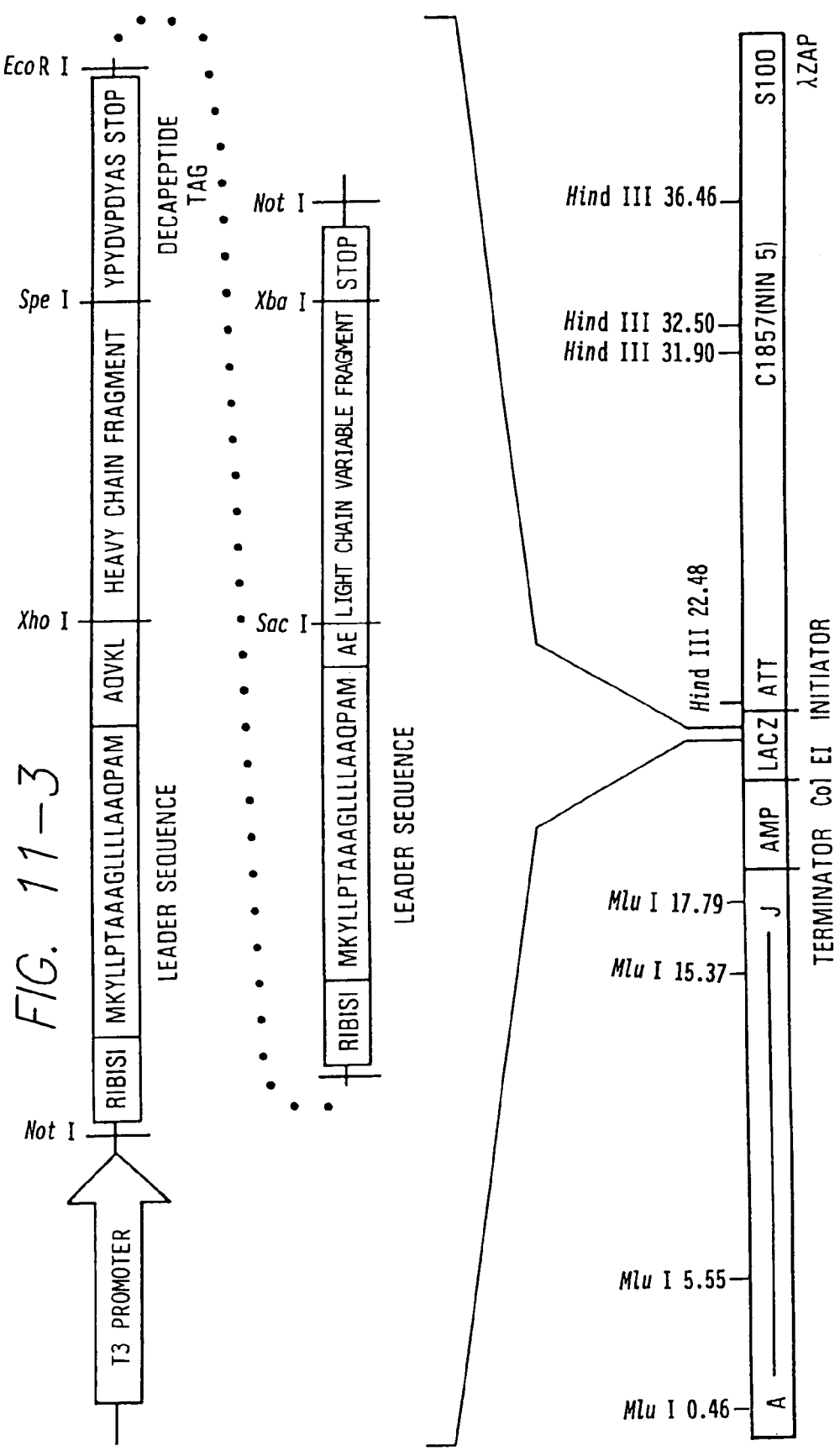

FIG. 11 The vectors for expressing $V_H$ and $V_L$ separately and in combination are shown. The various essential components of these vectors are shown. The light chain vector or $V_L$ expression vector can be combined with the $V_H$ expression vector to produce a combinatorial vector containing both $V_H$ and $V_L$ operatively linked for expression to the same promoter.

Figure 12:
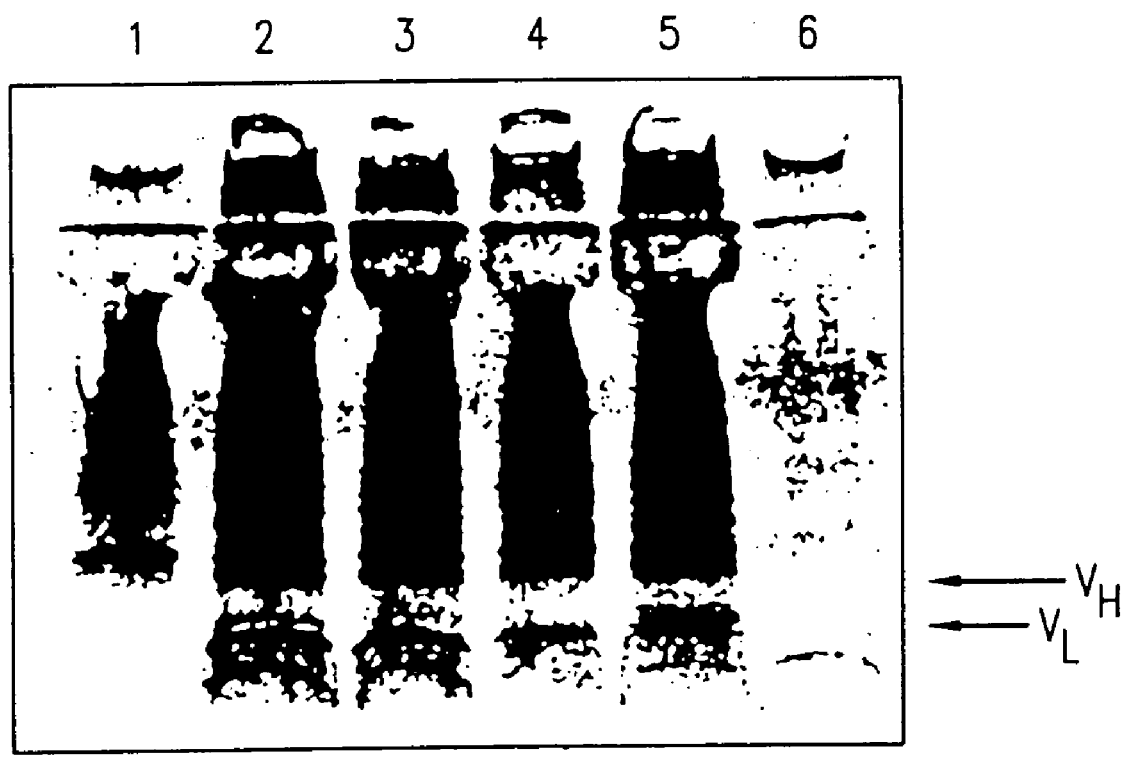

FIG. 12 The labelled proteins immunoprecipitated from E. coli containing a $V_H$ and a $V_L$ DNA homolog are shown. In lane 1, the background proteins immunoprecipitated from E. coli that do not contain a $V_H$ or $V_L$ DNA homolog are shown. Lane 2 contains the $V_H$ protein immunoprecipitated from E. coli containing only a $V_H$ DNA homolog. In lanes 3 and 4, the commigration of a $V_H$ protein a $V_L$ protein immunoprecipitated from E. coli containing both a $V_H$ and a $V_L$ DNA homolog is shown. In lane 5 the presence of $V_H$ protein and $V_L$ protein expressed from the $V_H$ and $V_L$ DNA homologs is demonstrated by the two distinguishable protein species. Lane 5 contains the background proteins immunoprecipitated by anti-E. coli antibodies present in mouse ascites fluid.

FIG. 13 The transition state analogue (formula 1) which induces antibodies for hydrolyzing carboxamide substrate (formula 2). The compound of formula 1 containing a glutaryl spacer and a N-hydroxysuccinimide-linker appendage is the form used to couple the hapten (formula 1) to protein carriers KLH and BSA, while the compound of formula 3 is the inhibitor. The phosphonamidate functionality is a mimic of the stereoelectronic features of the transition state for hydrolysis of the amide bond.

Figure 14:
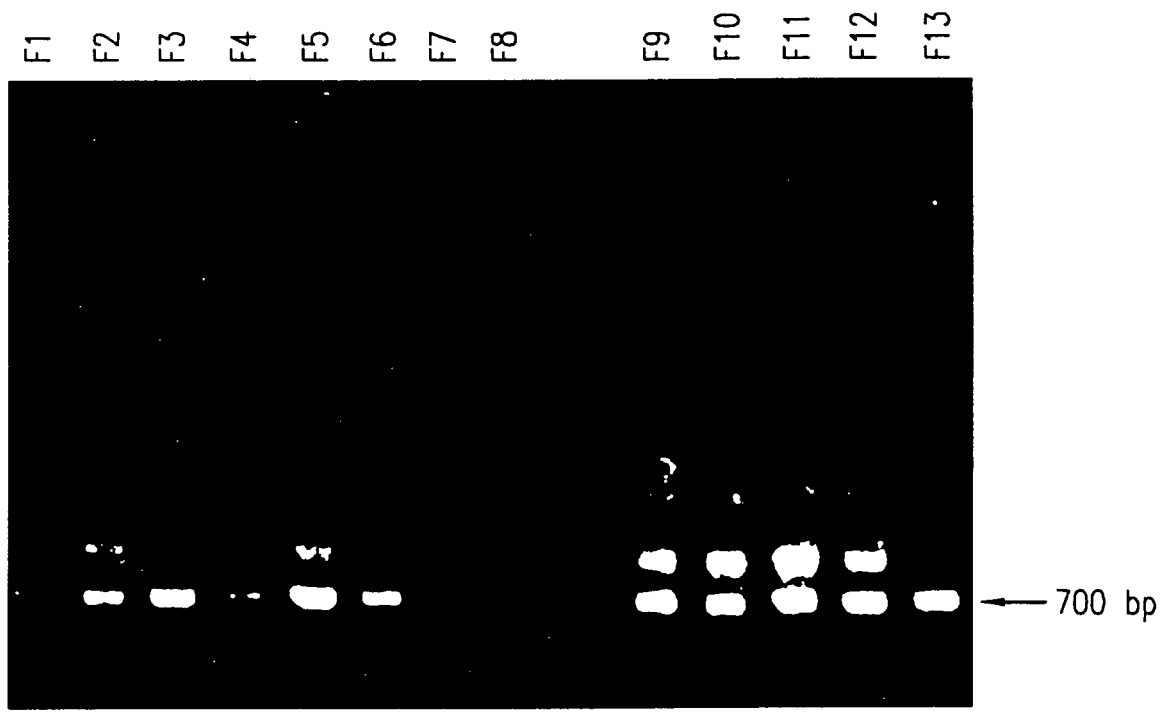

FIG. 14 PCR amplification of Fd and kappa regions from the spleen mRNA of a mouse immunized with NPN is illustrated. Amplification was performed as described in Example 18 using RNA cDNA hybrids obtained by the reverse transcription of the mRNA with primer specific for amplification of light chain sequences (Table 2 (SEQ ID NOS:60–84)) or heavy chain sequences (Table 1 (SEQ ID NOS:42–59)). Lanes F1–F8 represent the product of heavy chain amplification reactions with one of each of the eight 5' primers (primers 2–9, Table 1) and the unique 3' primer (primer 15, Table 2). Light chain (k) amplifications with the 5' primers (primers 3–6, and 12, respectively, Table 2) and the appropriate 3' primer (primer 13, Table 2) are shown in lanes F9–F13. A band of 700 bps is seen in all lanes indicating the successful amplification of Fd and k regions.

Figure 15:
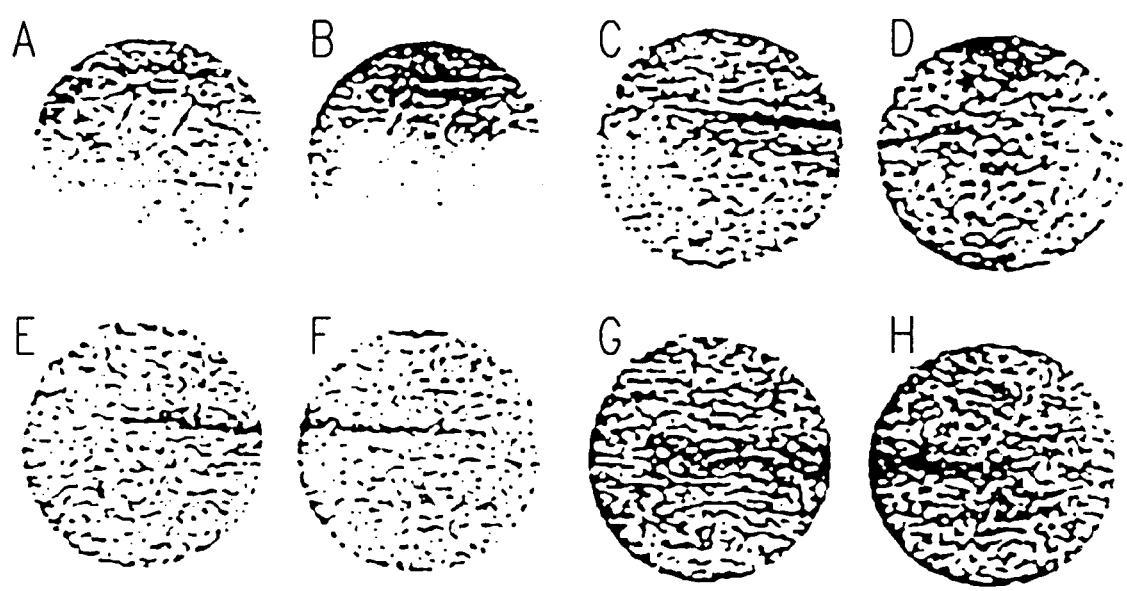

FIG. 15 The screening of phage libraries for antigen binding is depicted according to Example 18C. Duplicate plaque lifts of Fab (filters A, B), heavy chain (filters E, F) and light chain (filters G, H) expression libraries were screened against $^{125}$I-labelled BSA conjugated to NPN at a density of approximately 30,000 plaques per plate. Filters C and D illustrate the duplicate secondary screening of a cored positive from a primary filter A (arrows) as discussed in the text.

Screening employed standard plaque lift methods. XL1 Blue cells infected with phage were incubated on 150 mm plates for 4 h at 37°, protein expression induced by overlay with nitrocellulose filters soaked in 10 mM isopropyl thiogalactoside (IPTG) and the plates incubated at 25° for 8 h. Duplicate filters were obtained during a second incubation employing the same conditions. Filters were then blocked in a solution of 1% BSA in PBS for 1 h before incubation with rocking at 25° for 1 h with a solution of $^{125}$I-labelled BSA conjugated to NPN ($2\times10^6$ cpm ml$^{-1}$; BSA concentration at 0.1 M; approximately 15 NPN per BSA molecule) in 1% BSA/PBS. Background was reduced by pre-centrifugation of stock radiolabelled BSA solution at 100,000 g for 15 min and pre-incubation of solutions with plaque lifts from plates containing bacteria infected with a phage having no insert. After labeling, filters were washed repeatedly with PBS/ 0.05% Tween 20 before development of autoradiographs overnight.

Figure 16:
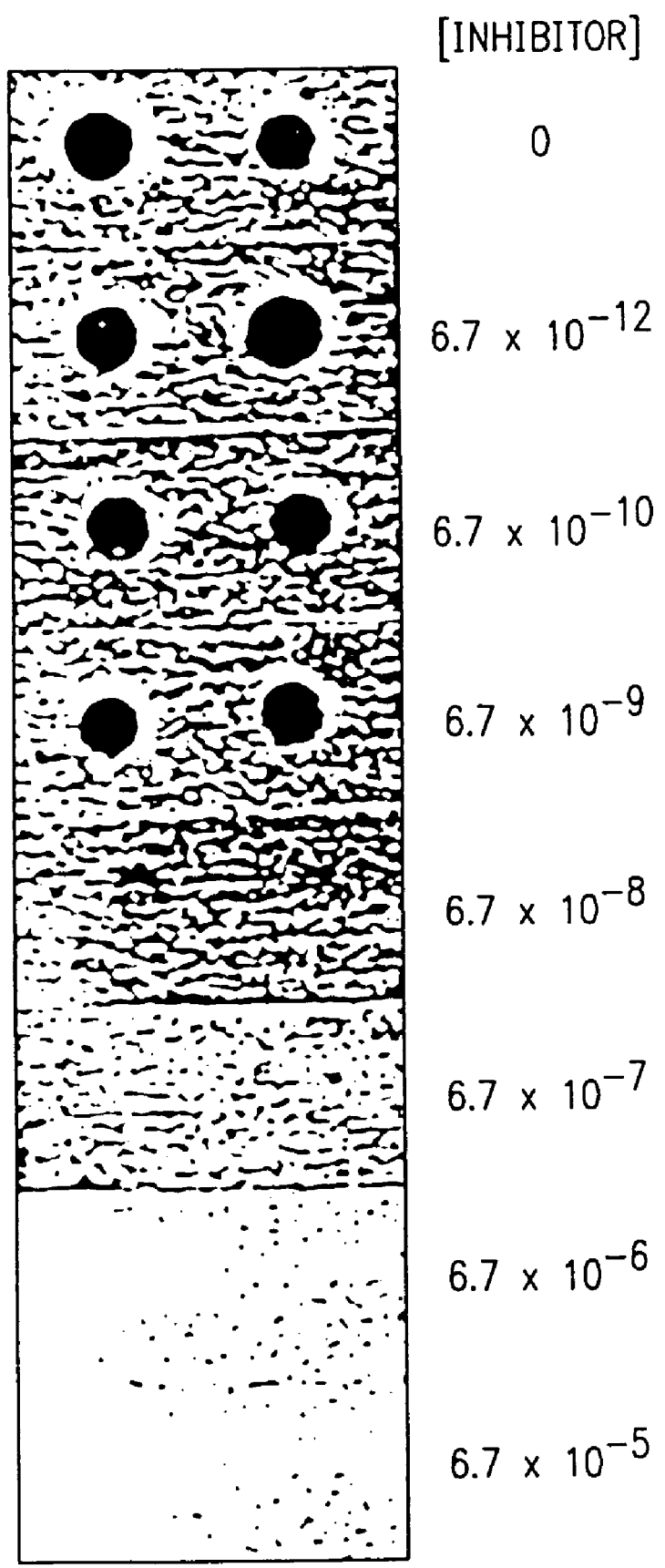

FIG. 16 The specificity of antigen binding as shown by competitive inhibition is illustrated according to Example 18C. Filter lifts from positive plaques were exposed to $^{125}$I-BSA-NPN in the presence of increasing concentrations of the inhibitor NPN.

In this study a number of phages correlated with NPN binding as in FIG. 15 were spotted (about 100 particles per spot) directly onto a bacterial lawns. The plate was then overlaid with an IPTG-soaked filter and incubated for 19 h at 25°. The filter were then blocked in 1% BSA in PBS prior to incubation in $^{125}$I-BSA-NPN as described previously in FIG. 15 except with the inclusion of varying amounts of NPN in the labeling solution. Other conditions and procedures were as in FIG. 15. The results for a phage of moderate affinity are shown in duplicate in the figure. Similar results were obtained for four other phages with some differences in the effective inhibitor concentration ranges.

Figure 17:
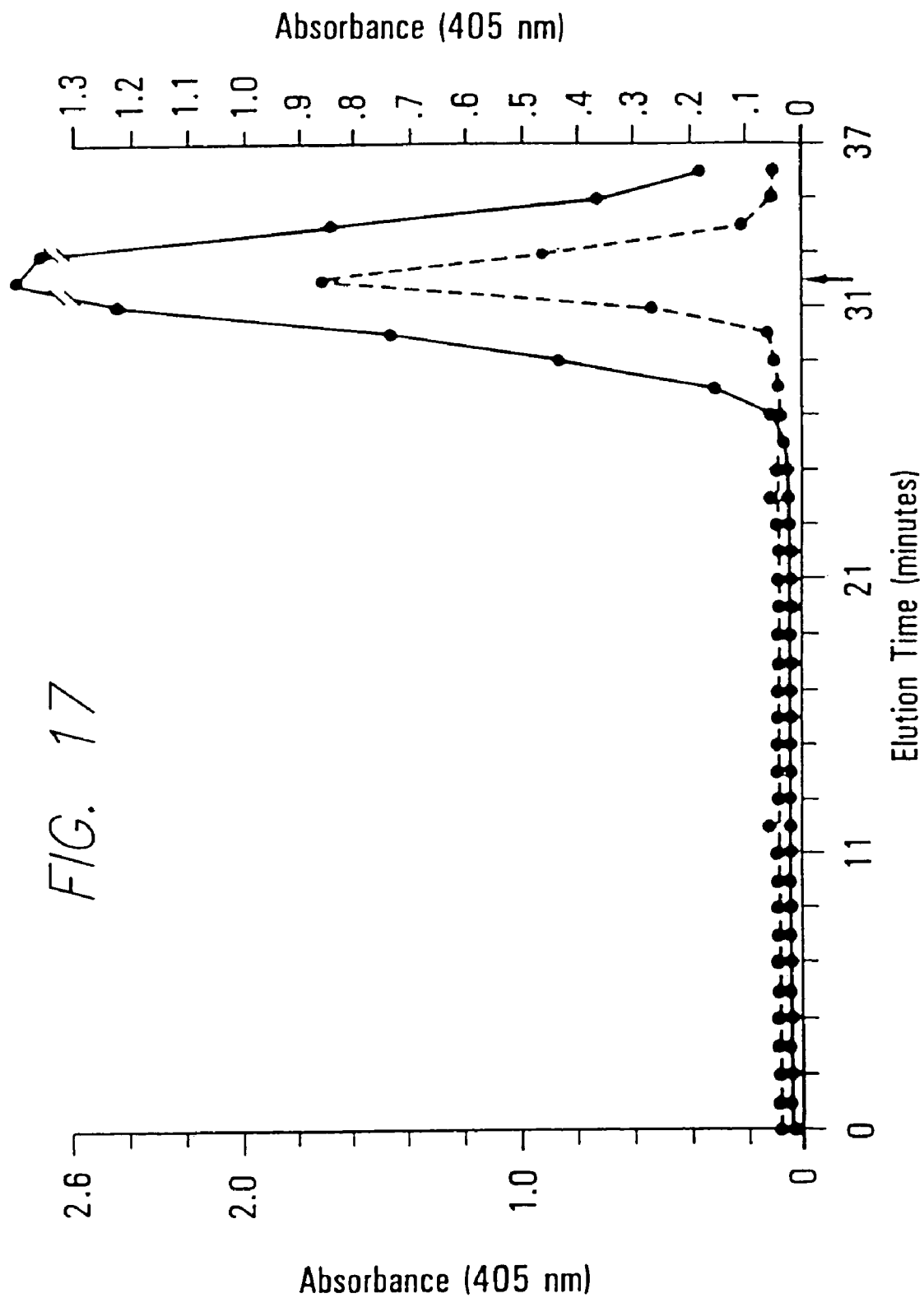

FIG. 17 The characterization of an antigen binding protein is illustrated according to Example 18D. The concentrated partially purified bacterial supernate of an NPN-binding clone was separated by gel filtration and aliquots from each fraction applied to microtitre plates coated with BSA-NPN. Addition of either anti-decapeptide (---) or anti-kappa chain (—) antibodies conjugated with alkaline phosphatase was followed by color development. The arrow indicates the position of elution of a known Fab fragment. The results show that antigen binding is a property of 50 kD protein containing both heavy and light chains.

Single plaques of two NPN-positive clones (FIG. 15) were picked and the plasmid containing the heavy and light chain inserts excised (19). 500 ml cultures in L-broth were inoculated with 3 ml of a saturated culture containing the excised plasmids and incubated for 4 h at 37°. Proteins synthesis was induced by the addition of IPTG to a final concentration of 1 mM and the cultures incubated for 10 h at 25%. 200 ml of cells supernate were concentrated to 2 ml and applied to a TSK-G4000 column. 50 ul aliquots from the eluted fractions were assayed by ELISA.

For ELISA analysis, microtitre plates were coated with BSA-NPN at 1 ug/ml, 50 ul samples mixed with 50 ul PBS-Tween 20 (0.05%)-BSA (0.1%) added and the plates incubated for 2 h at 25°. After washing with PBS-Tween 20-BSA, 50 ul of appropriate concentrations of a rabbit anti-decapeptide antibody (20) and a goat anti-mouse kappa light chain (Southern Biotech) antibody conjugated with alkaline phosphatase were added and incubated for 2 h at 25°. After further washing, 50 ul of p-nitrophenyl phosphate (1 mg/ml in 0.1M tris pH 9.5 containing 50 mM MgCl2) were added and the plates incubated for 15–30 min before reading the OD at 405 nm.

FIG. 18 The sequence of the synthetic DNA insert inserted into Lambda Zap II $V_H$ to produce the selectable $V_H$ expression vector (panel A (SEQ ID NO:119)) and Lambda Zap II $V_L$ II according to Example 17 to produce the selectable $V_L$ expression vector (panel B (SEQ ID NO:120)).

FIG. 19

(A) The major features of the selectable $V_L$ expression vector are shown in panel A. The feature of the synthetic DNA sequence from FIG. 18A (SEQ ID NO:119) is shown at the top along with the $T_3$ polymerase promoter from Lambda Zap II. The orientation of the insert in Lambda Zapp II is shown. The $V_H$ DNA homologs are inserted into the Xho I and Spe I restriction enzyme sites. The $V_H$ DNA homologs are inserted into the Xho I and Spe I site and the read through transcription produces the decapeptide epitope (tag) that is located just 3' of the cloning sites.

(B) The major features of the bacterial expression vector Lambda Zap II $V_H$ ($V_H$-expression vector) are shown. The synthetic DNA sequence from FIG. 6 (SEQ ID NO:38) is shown at the top along with the $T_3$ polymerase promoter from Lambda Zap II. The orientation of the insert in Lambda Zapp II is shown. The $V_H$ DNA homologs are inserted into the Xho I and Spe I restriction enzyme sites. The $V_H$ DNA are inserted into the Xho I and Spe I site and the read through transcription produces the decapeptide epitope (tag) that is located just 3' of the cloning sites.

Figure 20:
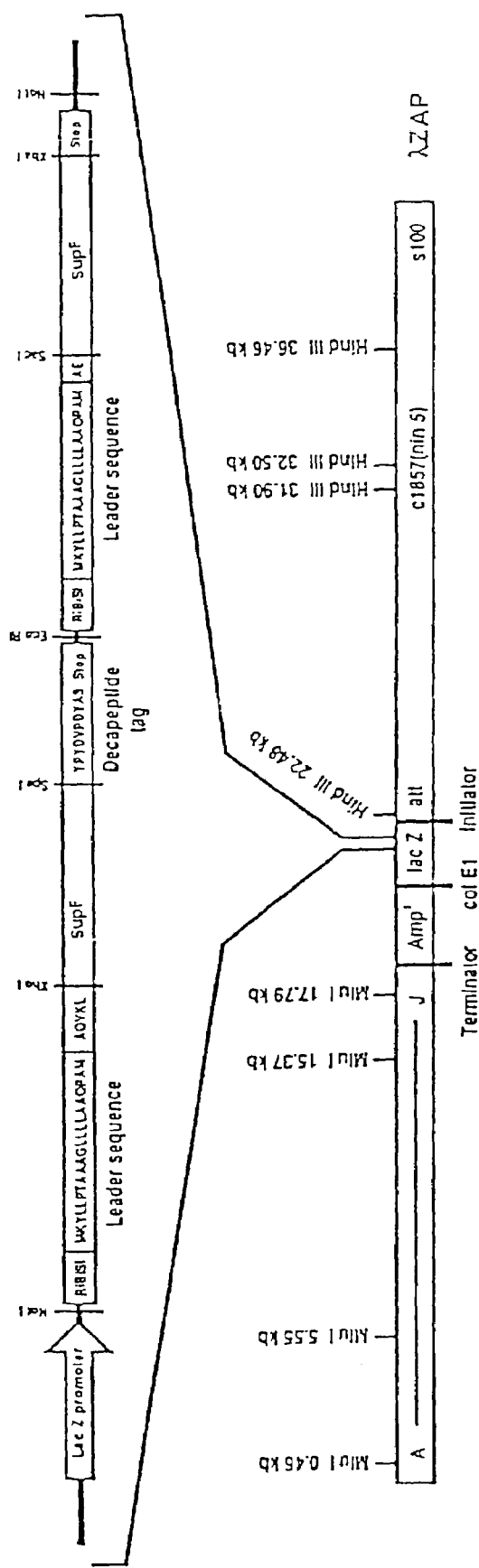

FIG. 20 One of the vectors for expression $V_H$ and $V_L$ in combination are shown. The various essential components of these vectors are shown. The selectable marker (sup F) is shown.

DETAILED DESCRIPTION OF THE INVENTION

A. Definitions

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide.

Base Pair (bp): a partnership of adenine (A) with thymine (T), or of cytosine (C) with guanine (G) in a double stranded DNA molecule. In RNA, uracil (U) is substituted for thymine.

Nucleic Acid: a polymer of nucleotides, either single or double stranded.

Gene: a nucleic acid whose nucleotide sequence codes for a RNA or polypeptide. A gene can be either RNA or DNA.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize to it with consequent hydrogen bonding.

Conserved: a nucleotide sequence is conserved with respect to a preselected (reference) sequence if it non-randomly hybridizes to an exact complement of the preselected sequence.

Hybridization: the pairing of substantially complementary nucleotide sequences (strands of nucleic acid) to form a duplex or heteroduplex by the establishment of hydrogen bonds between complementary base pairs. It is a specific, i.e. non-random, interaction between two complementary polynucleotide that can be competitively inhibited.

Nucleotide Analog: a purine or pyrimidine nucleotide that differs structurally from a, T, G, C, or U, but is sufficiently similar to substitute for the normal nucleotide in a nucleic acid molecule.

DNA Homolog: is a nucleic acid having a preselected conserved nucleotide sequence and a sequence coding for a receptor capable of binding a preselected ligand.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', $F(ab')_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: The phrase monoclonal antibody in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

B. Methods

The present invention provides a novel method for tapping the immunological repertoire by isolating from $V_H$-coding and $V_L$-coding gene repertoires genes coding for an antibody receptor heterodimer capable of binding a preselected ligand. Generally, the method combines the following elements:

1. Isolating nucleic acids containing a substantial portion of the immunological repertoire.

2. Preparing polynucleotide primers for cloning polynucleotide segments containing immunoglobulin $V_H$ and $V_L$ region genes.

3. Preparing a gene library containing a plurality of different $V_H$ and $V_L$ genes from the repertoire.

4. Expressing the $V_H$ and $V_L$ polypeptides in a suitable host, including prokaryotic and eukaryotic hosts, either separately or in the same cell, and either on the same or different expression vectors.

5. Screening the expressed polypeptides for the preselected activity, and segregating a $V_H$- and $V_L$-coding gene combination identified by the screening process.

An antibody produced by the present invention assumes a conformation having a binding site specific for as evidenced by its ability to be competitively inhibited, a preselected or predetermined ligand such as an antigen, enzymatic substrate and the like. In one embodiment, an antibody of this invention forms an antigen binding site which specifically binds to a preselected antigen to form an immunoreaction product (complex) having a sufficiently strong binding between the antigen and the binding site for the immunoreaction product to be isolated. The antibody typically has an affinity or avidity is generally greater than $10^5$ $M^{-1}$ more usually greater than $10^6$ and preferably greater than $10^8$ $M^{-1}$.

In another embodiment, an antibody of the subject invention binds a substrate and catalyzes the formation of a product from the substrate. While the topology of the ligand binding site of a catalytic antibody is probably more important for its preselected activity than its affinity (association constant or pKa) for the substrate, the subject catalytic antibodies have an association constant for the preselected substrate generally greater than $10^3$ $M^{-1}$, more usually greater than $10^5$ $M^{-1}$ or $10^6$ $M^{-1}$ and preferably greater than $10^7$ $M^{-1}$.

Preferably the antibody produced by the subject invention is heterodimeric and is therefore normally comprised of two different polypeptide chains, which together assume a conformation having a binding affinity, or association constant for the preselected antibody that is different, preferably higher, than the affinity or association constant of either of the polypeptides alone, i.e., as monomers. One or both of the different polypeptide chains is derived from the variable region of the light and heavy chains of an immunoglobulin. Typically, polypeptides comprising the light ($V_L$) and heavy ($V_H$) variable regions are employed together for binding the preselected antibody.

A $V_H$ or $V_L$ produced by the subject invention can be active in monomeric as well as multimeric forms, either homomeric or heteromeric, preferably heterodimeric. A $V_H$ and $V_L$ ligand binding polypeptide produced by the present invention can be advantageously combined in a heterodimer (antibody molecule) to modulate the activity of either or to produce an activity unique to the heterodimer. The individual ligand binding polypeptides will be referred to as $V_H$ and $V_L$ and the heterodimer will be referred to as an antibody molecule.

However, it should be understood that a $V_H$ binding polypeptide may contain in addition to the $V_H$, substantially all or a portion of the heavy chain constant region. A $V_L$ binding polypeptide may contain, in addition to the $V_L$, substantially all or a portion of the light chain constant region. A heterodimer comprised of a $V_H$ binding polypeptide containing a portion of the heavy chain constant region and a $V_L$ binding containing substantially all of the light chain constant region is termed a Fab fragment. The production of Fab can be advantageous in some situations because the additional constant region sequences contained in a Fab as compared to a $F_v$ could stabilize the $V_H$ and $V_L$ interaction. Such stabilization could cause the Fab to have higher affinity for antigen. In addition the Fab is more commonly used in the art and thus there are more commercial antibodies available to specifically recognize a Fab.

The individual $V_H$ and $V_L$ polypeptides will generally have fewer than 125 amino acid residues, more usually fewer than about 120 amino acid residues, while normally having greater than 60 amino acid residues, usually greater than about 95 amino acid residues, more usually greater than about 100 amino acid residues. Preferably, the $V_H$ will be from about 110 to about 125 amino acid residues in length while $V_L$ will be from about 95 to about 115 amino acid residues in length.

The amino acid residue sequences will vary widely, depending upon the particular idiotype involved. Usually, there will be at least two cysteines separated by from about 60 to 75 amino acid residues and joined by a disulfide bond. The polypeptides produced by the subject invention will normally be substantial copies of idiotypes of the variable regions of the heavy and/or light chains of immunoglobulins, but in some situations a polypeptide may contain random mutations in amino acid residue sequences in order to advantageously improve the desired activity.

In some situations, it is desirable to provide for covalent cross linking of the $V_H$ and $V_L$ polypeptides, which can be accomplished by providing cysteine resides at the carboxyl termini. The polypeptide will normally be prepared free of the immunoglobulin constant regions, however a small portion of the J region may be included as a result of the advantageous selection of DNA synthesis primers. The D region will normally be included in the transcript of the $V_H$.

In other situations, it is desirable to provide a peptide linker to connect the $V_L$ and the $V_H$ to form a single-chain antigen-binding protein comprised of a $V_H$ and a $V_L$. This single-chain antigen-binding protein would be synthesized as a single protein chain. Such single-chain antigen-binding proteins have been described by Bird et al., Science, 242: 423–426 (1988). The design of suitable peptide linker regions is described in U.S. Pat. No. 4,704,692 by Robert Landner.

Such a peptide linker could be designed as part of the nucleic acid sequences contained in the expression vector. The nucleic acid sequences coding for the peptide linker would be between the $V_H$ and $V_L$ DNA homologs and the restriction endonuclease sites used to operatively link the $V_H$ an $V_L$ DNA homologs to the expression vector.

Such a peptide linker could also be coded for nucleic acid sequences that are part of the polynucleotide primers used to prepare the various gene libraries. The nucleic acid sequence coding for the peptide linker can be made up of nucleic acids attached to one of the primers or the nucleic acid sequence coding for the peptide linker may be derived from nucleic acid sequences that are attached to several polynucleotide primers used to create the gene libraries.

Typically the C terminus region of the $V_H$ and $V_L$ polypeptides will have a greater variety of the sequences than the N terminus and, based on the present strategy, can be further modified to permit a variation of the normally occurring $V_H$ and $V_L$ chains. A synthetic polynucleotide can be employed to vary one or more amino in an hypervariable region.

1. Isolation of the Repertoire

To prepare a composition of nucleic acids containing a substantial portion of the immunological gene repertoire, a source of genes coding for the $V_H$ and/or $V_L$ polypeptides is required. Preferably the source will be a heterogeneous population of antibody producing cells, i.e. B lymphocytes (B cells), preferably rearranged B cells such as those found in the circulation or spleen of a vertebrate. (Rearranged B cells are those in which immunoglobulin gene translocation, i.e., rearrangement, has occurred as evidenced by the presence in the cell mRNA with the immunoglobulin gene V, D and J region transcripts adjacently located thereon.)

In some cases, it is desirable to bias the repertoire for a preselected activity, such as by using as a source of nucleic acid cells (source cells) from vertebrates in any one of various stages of age, health and immune response. For example, repeated immunization of a healthy animal prior to collecting rearranged B cells results in obtaining a repertoire enriched for genetic material producing a ligand binding polypeptide of high affinity. Conversely, collecting rearranged B cells from a healthy animal whose immune system has not been recently challenged results in producing a repertoire that is not biased towards the production of high affinity $V_H$ and/or $V_L$ polypeptides.

It should be noted the greater the genetic heterogeneity of the population of cells for which the nucleic acids are obtained, the greater the diversity of the immunological repertoire that will be made available for screening according to the method of the present invention. Thus, cells from different individuals, particularly those having an immunologically significant age difference, and cells from individuals of different strains, races or species can be advantageously combined to increase the heterogeneity of the repertoire.

Thus, in one preferred embodiment, the source cells are obtained from a vertebrate, preferably a mammal, which has been immunized or partially immunized with an antigenic ligand (antigen) against which activity is sought, i.e., a preselected antigen. The immunization can be carried out conventionally. Antibody titer in the animal can be monitored to determine the stage of immunization desired, which stage corresponds to the amount of enrichment or biasing of the repertoire desired. Partially immunized animals typically receive only one immunization and cells are collected therefrom shortly after a response is detected. Fully immunized animals display a peak titer, which is achieved with one or more repeated injections of the antigen into the host mammal, normally at 2 to 3 week intervals. Usually three to five days after the last challenge, the spleen is removed and the genetic repertoire of the spleenocytes, about 90% of which are rearranged B cells, is isolated using standard procedures. See, *Current Protocols in Molecular Biology*, Ausubel et al., eds., John Wiley & Sons, NY.

Nucleic acids coding for $V_H$ and $V_L$ polypeptides can be derived from cells producing IgA, IgD, IgE, IgG or IgM, most preferably from IgM and IgG, producing cells.

Methods for preparing fragments of genomic DNA from which immunoglobulin variable region genes can be cloned as a diverse population are well known in the art. See for example Herrmann et al., *Methods In Enzymol.*, 152:180–183, (1987); Frischauf, *Methods In Enzymol.*, 152:183–190 (1987); Frischauf, *Methods In Enzymol.*, 152:190–199 (1987); and DiLella et al., *Methods In Enzymol.*, 152:199–212 (1987). (The teachings of the references cited herein are hereby incorporated by reference.)

The desired gene repertoire can be isolated from either genomic material containing the gene expressing the variable region or the messenger RNA (mRNA) which represents a transcript of the variable region. The difficulty in using the genomic DNA from other than non-rearranged B lymphocytes is in juxtaposing the sequences coding for the variable region, where the sequences are separated by introns. The DNA fragment(s) containing the proper exons must be isolated, the introns excised, and the exons then spliced in the proper order and in the proper orientation. For the most part, this will be difficult, so that the alternative technique employing rearranged B cells will be the method of choice because the C D and J immunoglobulin gene regions have translocated to become adjacent, so that the sequence is continuous (free of introns) for the entire variable regions.

Where mRNA is utilized the cells will be lysed under RNase inhibiting conditions. In one embodiment, the first step is to isolate the total cellular mRNA by hybridization to an oligo-dT cellulose column. The presence of mRNAs coding for the heavy and/or light chain polypeptides can then be assayed by hybridization with DNA single strands of the appropriate genes. Conveniently, the sequences coding for the constant portion of the $V_H$ and $V_L$ can be used as polynucleotide probes, which sequences can be obtained from available sources. See for example, Early and Hood, *Genetic Engineering*, Setlow and Hollaender, eds., Vol. 3, Plenum Publishing Corporation, New York, (1981), pages 157–188; and Kabat et al., *Sequences of Immunological Interest*, National Institutes of Health, Bethesda, Md., (1987).

In preferred embodiments, the preparation containing the total cellular mRNA is first enriched for the presence of $V_H$ and/or $V_L$ coding mRNA. Enrichment is typically accomplished by subjecting the total mRNA preparation or partially purified mRNA product thereof to a primer extension reaction employing a polynucleotide synthesis primer of the present invention.

2. Preparation of Polynucleotide Primers

The term "polynucleotide" as used herein in reference to primers, probes and nucleic acid fragments or segments to be synthesized by primer extension is defined as a molecule comprised of two or more deoxyribonucleotides or ribonucleotides, preferably more than 3. Its exact size will depend on many factors, which in turn depends on the ultimate conditions of use.

The term "primer" as used herein refers to a polynucleotide whether purified from a nucleic acid restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be double stranded. If double stranded, the primer is first treated to separate its strands before being used to prepare extension products. Preferably, the primer is a polydeoxyribonucleotide. The primer must be sufficiently long to prime the synthesis of extension products in the presence of the agents for polymerization. The exact lengths of the primers will depend on may factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to nonrandomly hybridize with its respective template strand. Therefore, the primer sequence may not reflect the exact sequence of the template. For example, a non-complementary nucleotide fragment can be attached to the 5' end of the primer, with the remainder of the primer sequence being substantially complementary to the strand. Such noncomplementary fragments typically code for an endonuclease restriction site. Alternatively, noncomplementary bases or longer sequences can be interspersed into the primer, provided the primer sequence has sufficient complementarily with the sequence of the strand to be synthesized or amplified to non-randomly hybridize therewith and thereby form an extension product under polynucleotide synthesizing conditions.

The polynucleotide primers can be prepared using any suitable method, such as, for example, the phosphotriester on phosphodiester methods see Narang et al., *Meth. Enzymol.*, 68:90, (1979); U.S. Pat. No. 4,356,270; and Brown et al., *Meth. Enzymol.*, 68:109, (1979). The choice of a primer's nucleotide sequence depends on factors such as the distance on the nucleic acid from the region coding for the desired receptor, its hybridization site on the nucleic acid relative to any second primer to be used, the number of genes in the repertoire it is to hybridize to, and the like.

For example, to produce $V_H$-coding DNA homologs by primer extension, the nucleotide sequence of a primer is selected to hybridize with a plurality of immunoglobulin heavy chain genes at a site substantially adjacent to the $V_H$-coding region so that a nucleotide sequence coding for a functional (capable of binding) polypeptide is obtained. To hybridize to a plurality of different $V_H$-coding nucleic acid strands, the primer must be a substantial complement of a nucleotide sequence conserved among the different strands. Such sites include nucleotide sequences in the constant region, any of the variable region framework regions, preferably the third framework region, leader region, promoter region, J region and the like.

If the $V_H$-coding and $V_L$-coding DNA homologs are to be produced by polymerase chain reaction (PCR) amplification, two primers must be used for each coding strand of nucleic acid to be amplified. The first primer becomes part of the nonsense (minus or complimentary) strand and hybridizes to a nucleotide sequence conserved among $V_H$ (plus) strands within the repertoire. To produce $V_H$ coding DNA homologs, first primers are therefore chosen to hybridize to (i.e. be complementary to) conserved regions within the J region, CH1 region, hinge region, CH2 region, or CH3 region of immunoglobulin genes and the like. To produce a $V_L$ coding DNA homolog, first primers are chosen to hybridize with (i.e. be complementary to) a conserved region within the J region or constant region of immunoglobulin light chain genes and the like. Second primers become part of the coding (plus) strand and hybridize to a nucleotide sequence conserved among minus strands. To produce the $V_H$-coding DNA homologs, second primers are therefore chosen to hybridize with a conserved nucleotide sequence at the 5' end of the $V_H$-coding immunoglobulin gene such as in that area coding for the leader or first framework region. It should be noted that in the amplification of both $V_H$- and $V_L$-coding DNA homologs the conserved 5' nucleotide sequence of the second primer can be complementary to a sequence exogenously added using terminal deoxynucleotidyl transferase as described by Loh et al., Sci. Vol 243:217–220 (1989). One or both of the first and second primers can contain a nucleotide sequence defining an endonuclease recognition site. The site can be heterologous to the immunoglobulin gene being amplified and typically appears at or near the 5' end of the primer.

3. Preparing a Gene Library

The strategy used for cloning, i.e., substantially reproducing, the $V_H$ and/or $V_L$ genes contained within the isolated repertoire will depend, as is well known in the art, on the type, complexity, and purity of the nucleic acids making up the repertoire. Other factors include whether or not the genes are to be amplified and/or mutagenized.

In one strategy, the object is to clone the $V_H$- and/or $V_L$-coding genes from a repertoire comprised of polynucleotide coding strands, such as mRNA and/or the sense strand of genomic DNA. If the repertoire is in the form of double stranded genomic DNA, it is usually first denatured, typically by melting, into single strands. The repertoire is subjected to a first primary extension reaction by treating (contacting) the repertoire with a first polynucleotide synthesis primer having a preselected nucleotide sequence. The first primer is capable of initiating the first primer extension reaction by hybridizing to a nucleotide sequence, preferably at least about 10 nucleotides in length and more preferably at least about 20 nucleotides in length, conserved within the repertoire. The first primer is sometimes referred to herein as the "sense primer" because it hybridizes to the coding or sense strand of a nucleic acid. In addition, the second primer is sometimes referred to herein as the "anti-sense primer" because it hybridizes to a non-coding or anti-sense strand of a nucleic acid, i.e., a strand complementary to a coding strand.

The first primer extension is performed by mixing the first primer, preferably a predetermined amount thereof, with the nucleic acids of the repertoire, preferably a predetermined amount thereof, to form a first primer extension reaction admixture. The admixture is maintained under polynucleotide synthesizing conditions for a time period, which is typically predetermined, sufficient for the formation of a first primer extension reaction product, thereby producing a plurality of different $V_H$-coding DNA homolog complements. The complements are then subjected to a second primer extension reaction by treating them with a second polynucleotide synthesis primer having a preselected nucleotide sequence. The second primer is capable of initiating the second reaction by hybridizing to a nucleotide sequence, preferably at least about 10 nucleotides in length and more preferably at least about 20 nucleotides in length, conserved among a plurality of different $V_H$-coding gene complements such as those, for example, produced by the first primer extension reaction. This is accomplished by mixing the second primer, preferably a predetermined amount thereof, with the complement nucleic acids, preferably a predetermined amount thereof, to form a second primer extension reaction admixture. The admixture is maintained under polynucleotide synthesizing conditions for a time period, which is typically predetermined, sufficient for the formation of a first primer extension reaction product, thereby producing a gene library containing a plurality of different $V_H$-and/or $V_L$-coding DNA homologs.

A plurality of first primer and/or a plurality of second primers can be used in each amplification, or an individual pair of first and second primers can be used. In any case, the amplification products of amplifications using the same or different combinations of first and second primers can be combined to increase the diversity of the gene library.

In another strategy, the object is to clone the $V_H$- and/or $V_L$-coding genes from a repertoire by providing a polynucleotide complement of the repertoire, such as the anti-sense strand of genomic dsDNA or the polynucleotide produced by subjecting mRNA to a reverse transcriptase reaction. Methods for producing such complements are well known in the art. The complement is subjected to a primer extension reaction similar to the above-described second primer extension reaction, i.e., a primer extension reaction using a polynucleotide synthesis primer capable of hybridizing to a nucleotide sequence conserved among a plurality of different $V_H$-coding gene complements. The primer extension reaction is performed using any suitable method. Generally it occurs in a buffered aqueous solution, preferably at a pH of 7–9, most preferably about 8. Preferably, a molar excess (for genomic nucleic acid, usually about $10^6$:1 primer: template) of the primer is admixed to the buffer containing the template strand. A large molar excess is preferred to improve the efficiency of the process.

The deoxyribonucleotide triphosphates dATP, dCTP, dGTP, and dTTP are also admixed to the primer extension (polynucleotide synthesis) reaction admixture in adequate amounts and the resulting solution is heated to about 90 C–100 for about 1 to 10 minutes, preferably from 1 to 4 minutes. After this heating period the solution is allowed to cool to room temperature, which is preferable for primer hybridization. To the cooled mixture is added an appropriate agent for inducing or catalyzing the primer extension reaction, and the reaction is allowed to occur under conditions known in the art. The synthesis reaction may occur at from room temperature up to a temperature above which the inducing agent no longer functions efficiently. Thus, for example, if DNA polymerase is used as inducing agent, the temperature is generally no greater than about 40 C.

The inducing agent may be any compound or system which will function to accomplish the synthesis of primer extension products, including enzymes. Suitable enzymes for this purpose include, for example, E. coli, DNA polymerase I, Klenow fragment of E. coli DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The newly synthesized strand and its complementary nucleic acid strand form a double-stranded molecule which can be used in the succeeding steps of the process.

The first and/or second primer extension reaction discussed above can advantageously be used to incorporate into the receptor a preselected epitope useful in immunologically detecting and/or isolating a receptor. This is accomplished by utilizing a first and/or second polynucleotide synthesis primer or expression vector to incorporate a predetermined amino acid residue sequence into the amino acid residue sequence of the receptor.

After producing $V_H$- and/or $V_L$-coding DNA homologs for a plurality of different $V_H$- and/or $V_L$-coding genes within the repertoire, the homologs are typically amplified. While the $V_H$ and/or $V_L$-coding DNA homologs can be amplified by classic techniques such as incorporation into an autonomously replicating vector, it is preferred to first amplify the DNA homologs by subjecting them to a polymerase chain reaction (PCR) prior to inserting them into a vector. In fact, in preferred strategies, the first and/or second primer extension reactions used to produce the gene library are the first and second primer extension reactions in a polymerase chain reaction.

PCR is typically carried out by cycling i.e., simultaneously performing in one admixture, the above described first and second primer extension reactions, each cycle comprising polynucleotide synthesis followed by denaturation of the double stranded polynucleotides formed. Methods and systems for amplifying a DNA homolog are described in U.S. Pat. No. 4,683,195 and No. 4,683,202, both to Mullis et al.

In preferred embodiments only one pair of first and second primers is used per amplification reaction. The amplification reaction products obtained from a plurality of different amplifications, each using a plurality of different primer pairs, are then combined.

However, the present invention also contemplates DNA homolog production via co-amplification (using two pairs of primers), and multiplex amplification (using up to about 8, 9 or 10 primer pairs).

The $V_H$- and $V_L$-coding DNA homologs produced by PCR amplification are typically in double-stranded form and have contiguous or adjacent to each of their termini a nucleotide sequence defining an endonuclease restriction site. Digestion of the $V_H$-and $V_L$-coding DNA homologs having restriction sites at or near their termini with one or more appropriate endonucleases results in the production of homologs having cohesive termini of predetermined specificity.

In preferred embodiments, the PCR process is used not only to amplify the $V_H$- and/or $V_L$-coding DNA homologs of the library, but also to induce mutations within the library and thereby provide a library having a greater heterogeneity. First, it should be noted that the PCR processes itself is inherently mutagenic due to a variety of factors well known in the art. Second, in addition to the mutation inducing variations described in the above referenced U.S. Pat. No. 4,683,195, other mutation inducing PCR variations can be employed. For example, the PCR reaction admixture, i.e., the combined first and second primer extension reaction admixtures, can be formed with different amounts of one or more of the nucleotides to be incorporated into the extension product. Under such conditions, the PCR reaction proceeds to produce nucleotide substitutions within the extension product as a result of the scarcity of a particular base. Similarly, approximately equal molar amounts of the nucleotides can be incorporated into the initial PCR reaction admixture in an amount to efficiently perform X number of cycles, and then cycling the admixture through a number of cycles in excess of X, such as, for instance, 2X. Alternatively, mutations can be induced during the PCR reaction by incorporating into the reaction admixture nucleotide derivatives such as inosine, not normally found in the nucleic acids of the repertoire being amplified. During subsequent in vivo amplification, the nucleotide derivative will be replaced with a substitute nucleotide thereby inducing a point mutation.

4. Expressing the $V_H$ and/or $V_L$ DNA Homologs.

The $V_H$ and/or $V_L$-coding DNA homologs contained within the library produced by the above-described method can be operatively linked to a vector for amplification and/or expression.

As used herein, the term "vector" refers to a nucleic acid molecule capable of transporting between different genetic environments another nucleic acid to which it has been operatively linked. One type of preferred vector is an episome, i.e., a nucleic acid molecule capable of extra-chromosomal replication. Preferred vectors are those capable of autonomous replication and/or expression of nucleic acids to which they are linked. Vectors capable of directing the expression of genes to which they are operatively linked are referred to herein as "expression vectors".

The choice of vector to which a $V_H$- and/or $V_L$-coding DNA homolog is operatively linked depends directly, as is well known in the art, on the functional properties desired, e.g., replication or protein expression, and the host cell to be transformed, these being limitations inherent in the art of constructing recombinant DNA molecules. In preferred embodiments, the vector utilized includes a procaryotic replicon i.e., a DNA sequence having the ability to direct autonomous replication and maintenance of the recombinant DNA molecule extra chromosomally in a procaryotic host cell, such as a bacterial host cell, transformed therewith. Such replicons are well known in the art. In addition, those embodiments that include a procaryotic replicon also include a gene whose expression confers a selective advantage, such as drug resistance, to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the $V_H$- and/or $V_L$-coding homologs in a bacterial host cell, such as *E. coli* transformed therewith. A promoter is an expression control element formed by a DNA sequence that permits binding of RNA polymerase and transcription to occur. Promoter sequences compatible with bacterial hosts are typically provided in plasmid vectors containing convenience restriction sites for insertion of a DNA segment of the present invention. Typical of such vector plasmids are pUC8, pUC9, pBR322, and pBR329 available from BioRad Laboratories, (Richmond, Calif.) and pPL and pKK223 available from Pharmacia, (Piscataway, N.J.).

Expression vectors compatible with eucaryotic cells, preferably those compatible with vertebrate cells, can also be used. Eucaryotic cell expression vectors are well known in the art and are available from several commercial sources. Typically, such vectors are provided containing convenient restriction sites for insertion of the desired DNA homologue. Typical of such vectors are pSVL and pKSV-10 (Pharmacia), pBPV-1/PML2d (International Biotechnologies, Inc.), and pTDT1 (ATCC, No. 31255).

In preferred embodiments, the eucaryotic cell expression vectors used include a selection marker that is effective in an eucaryotic cell, preferably a drug resistant selection marker. A preferred drug resistance marker is the gene whose expression results in neomycin resistance, i.e., the neomycin phosphotransferase (neo) gene. Southern et al., *J. Mol. Appl. Genet.*, 1:327–341 (1982).

The use of retroviral expression vectors to express the genes of the $V_H$ and/or $V_L$-coding DNA homologs is also contemplated. As used herein, the term "retroviral expression vector" refers to a DNA molecule that includes a promoter sequences derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge et al., *Mol. Cel. Biol.*, 4:1730–1737 (1984).

A variety of methods have been developed to operatively link DNA to vectors via complementary cohesive termini. For instance, complementary cohesive termini can be engineered into the $V_H$- and/or $V_L$-coding DNA homologs during the primer extension reaction by use of an appropriately designed polynucleotide synthesis primer, as previously discussed. The vector, and DNA homolog if necessary, is cleaved with a restriction endonuclease to produce termini complementary to those of the DNA homolog. The complementary cohesive termini of the vector and the DNA homolog are then operatively linked (ligated) to produce a unitary double stranded DNA molecule.

In preferred embodiments, the $V_H$-coding and $V_L$-coding DNA homologs of diverse libraries are randomly combined in vitro for polycistronic expression from individual vectors. That is, a diverse population of double stranded DNA expression vectors is produced wherein each vector expresses, under the control of a single promoter, one $V_H$-coding DNA homolog and one $V_L$-coding DNA homolog, the diversity of the population being the result of different $V_H$- and $V_L$-coding DNA homolog combinations.

Random combination in vitro can be accomplished using two expression vectors distinguished from one another by the location on each of a restriction site common to both. Preferably the vectors are linear double stranded DNA, such as a Lambda Zap derived vector as described herein. In the first vector, the site is located between a promoter and a polylinker, i.e., 5' terminal (upstream relative to the direction of expression) to the polylinker but 3' terminal (downstream relative to the direction of expression). In the second vector, the polylinker is located between a promoter and the restriction site, i.e., the restriction site is located 3' terminal to the polylinker, and the polylinker is located 3' terminal to the promoter.

In preferred embodiments, each of the vectors defines a nucleotide sequence coding for a ribosome binding and a leader, the sequence being located between the promoter and the polylinker, but downstream (3' terminal) from the shared restriction site if that site is between the promoter and polylinker. Also preferred are vectors containing a stop codon downstream from the polylinker, but upstream from any shared restriction site if that site is downstream from the polylinker. The first and/or second vector can also define a nucleotide sequence coding for a peptide tag. The tag sequence is typically located downstream from the polylinker but upstream from any stop codon that may be present.

In preferred embodiments, the vectors contain selectable markers such that the presence of a portion of that vector, i.e. a particular lambda arm, can be selected for or selected against. Typical selectable markers are well known to those skilled in the art. Examples of such markers are antibiotic resistance genes, genetically selectable markers, mutation suppressors such as amber suppressors and the like. The selectable markers are typically located upstream of the promoter and/or downstream of the second restriction site. In preferred embodiments, one selectable marker is located upstream of the promoter on the first vector containing the $V_H$-coding DNA homologs. A second selectable marker is located downstream of the second restriction site on the vector containing the $V_L$-coding DNA homologs. This second selectable marker may be the same or different from the first as long as when the $V_H$-coding vectors and the $V_L$-coding vectors are randomly combined via the first restriction site the resulting vectors containing both $V_H$ and $V_L$ and both selectable markers can be selected.

Typically the polylinker is a nucleotide sequence that defines one or more, preferably at least two, restriction sites, each unique to the vector and preferably not shared by the other vector, i.e., if it is on the first vector, it is not on the second vector. The polylinker restriction sites are oriented to permit ligation of $V_H$- or $V_L$-coding DNA homologs into the vector in same reading frame as any leader, tag or stop codon sequence present.

Random combination is accomplished by ligating $V_H$-coding DNA homologs into the first vector, typically at a restriction site or sites within the polylinker. Similarly, $V_L$-coding DNA homologs are ligated into the second vector, thereby creating two diverse populations of expression vectors. It does not matter which type of DNA homolog, i.e., $V_H$ or $V_L$, is ligated to which vector, but it is preferred, for example, that all $V_H$-coding DNA homologs are ligated to either the first or second vector, and all of the $V_L$-coding DNA homologs are ligated to the other of the first or second vector. The members of both populations are then cleaved with an endonuclease at the shared restriction site, typically by digesting both populations with the same enzyme. The resulting product is two diverse populations of restriction fragments where the members of one have cohesive termini complementary to the cohesive termini of the members of the other. The restriction fragments of the two populations are randomly ligated to one another, i.e., a random, interpopulation ligation is performed, to produce a diverse population of vectors each having a $V_H$-coding and $V_L$-coding DNA homolog located in the same reading frame and under the control of second vector's promoter. Of course, subsequent recombinations can be effected through cleavage at the shared restriction site, which is typically reformed upon ligation of members from the two populations, followed by subsequent religations.

The resulting construct is then introduced into an appropriate host to provide amplification and/or expression of the $V_H$- and/or $V_L$-coding DNA homologs, either separately or in combination. When coexpressed within the same organism, either on the same or the different vectors, a functionally active Fv is produced. When the $V_H$ and $V_L$ polypeptides are expressed in different organisms, the respective polypeptides are isolated and then combined in an appropriate medium to form a Fv. Cellular hosts into which a $V_H$- and/or $V_L$-coding DNA homolog-containing construct has been introduced are referred to herein as having been "transformed" or as "transformants".

The host cell can be either procaryotic or eucaryotic. Bacterial cells are preferred procaryotic host cells and typically are a strain of *E. coli* such as, for example, the *E. coli* strain DH5 available from Bethesda Research Laboratories, Inc., Bethesda, Md. Preferred eucaryotic host cells include yeast and mammalian cells, preferably vertebrate cells such as those from a mouse, rat, monkey or human cell line.

Transformation of appropriate cell hosts with a recombinant DNA molecule of the present invention is accomplished by methods that typically depend on the type of vector used. With regard to transformation of procaryotic host cells, see, for example, Cohen et al., *Proceedings National Academy of Science*, USA, Vol. 69, P. 2110 (1972); and Maniatis et al., *Molecular Cloning, a Laboratory Manual*, Cold Spring Harbor Laboratory, Cold Spring Harbor, N.Y. (1982). With regard to the transformation of vertebrate cells with retroviral vectors containing rDNAs, see for example, Sorge et al., *Mol. Cell. Biol.*, 4:1730–1737 (1984); Graham et al., *Virol.*, 52:456 (1973); and Wigler et al., *Proceedings National Academy of Sciences*, USA, Vol. 76, P. 1373–1376 (1979).

5. Screening For Expression of $V_H$ and/or $V_L$ Polypeptides

Successfully transformed cells, i.e., cells containing a $V_H$-and/or $V_L$-coding DNA homolog operatively linked to a vector, can be identified by any suitable well known technique for detecting the binding of a receptor to a ligand or the presence of a polynucleotide coding for the receptor, preferably its active site. Preferred screening assays are those where the binding of ligand by the receptor produces a detectable signal, either directly or indirectly. Such signals include, for example, the production of a complex, formation of a catalytic reaction product, the release or uptake of energy, and the like. For example, cells from a population subjected to transformation with a subject rDNA can be cloned to produce monoclonal colonies. Cells form those colonies can be harvested, lysed and their DNA content examined for the presence of the rDNA using a method such as that described by Southern, *J. Mol. Biol.*, 98:503 (1975) or Berent et al., *Biotech.* 3:208 (1985).

In addition to directly assaying for the presence of a $V_H$- and/or $V_L$-coding DNA homolog, successful transformation can be confirmed by well known immunological methods, especially when the $V_H$ and/or $V_L$ polypeptides produced contain a preselected epitope. For example, samples of cells suspected of being transformed are assayed for the presence of the preselected epitope using an antibody against the epitope.

6. $V_H$- and/or $V_L$-Coding Gene Libraries

The present invention contemplates a gene library, preferably produced by a primer extension reaction or combination of primer extension reactions as described herein, containing at least about $10^3$, preferably at least about $10^4$ and more preferably at least about $10^5$ different $V_H$- and/or $V_L$-coding DNA homologs. The homologs are preferably in an isolated form, that is, substantially free of materials such as, for example, primer extension reaction agents and/or substrates, genomic DNA segments, and the like.

In preferred embodiments, a substantial portion of the homologs present in the library are operatively linked to a vector, preferably operatively linked for expression to an expression vector.

Preferably, the homologs are present in a medium suitable for in vitro manipulation, such as water, water containing buffering salts, and the like. The medium should be compatible with maintaining the biological activity of the homologs. In addition, the homologs should be present at a concentration sufficient to allow transformation of a host cell compatible therewith at reasonable frequencies.

It is further preferred that the homologs be present in compatible host cells transformed therewith.

D. Expression Vectors

The present invention also contemplates various expression vectors useful in performing, inter alia, the methods of the present invention. Each of the expression vectors is a novel derivative of Lambda Zap.

1. Lambda Zap II

Lambda Zap II is prepared by replacing the Lambda S gene of the vector Lambda Zap with the Lambda S gene from the Lambda gt10 vector, as described in Example 6.

2. Lambda Zap II $V_H$

Lambda Zap II $V_H$ is prepared by inserting the synthetic DNA sequences illustrated in FIG. 6A (SEQ ID NO:38) into the above-described Lambda Zap II vector. The inserted nucleotide sequence advantageously provides a ribosome binding site (Shine-Dalgarno sequence) to permit proper imitation of mRNA translation into protein, and a leader sequence to efficiently direct the translated protein to the periplasm. The preparation of Lambda Zap II $V_H$ is described in more detail in Example 9, and its features illustrated in FIGS. 6A and 7.

3. Lambda Zap II $V_L$

Figure 8:
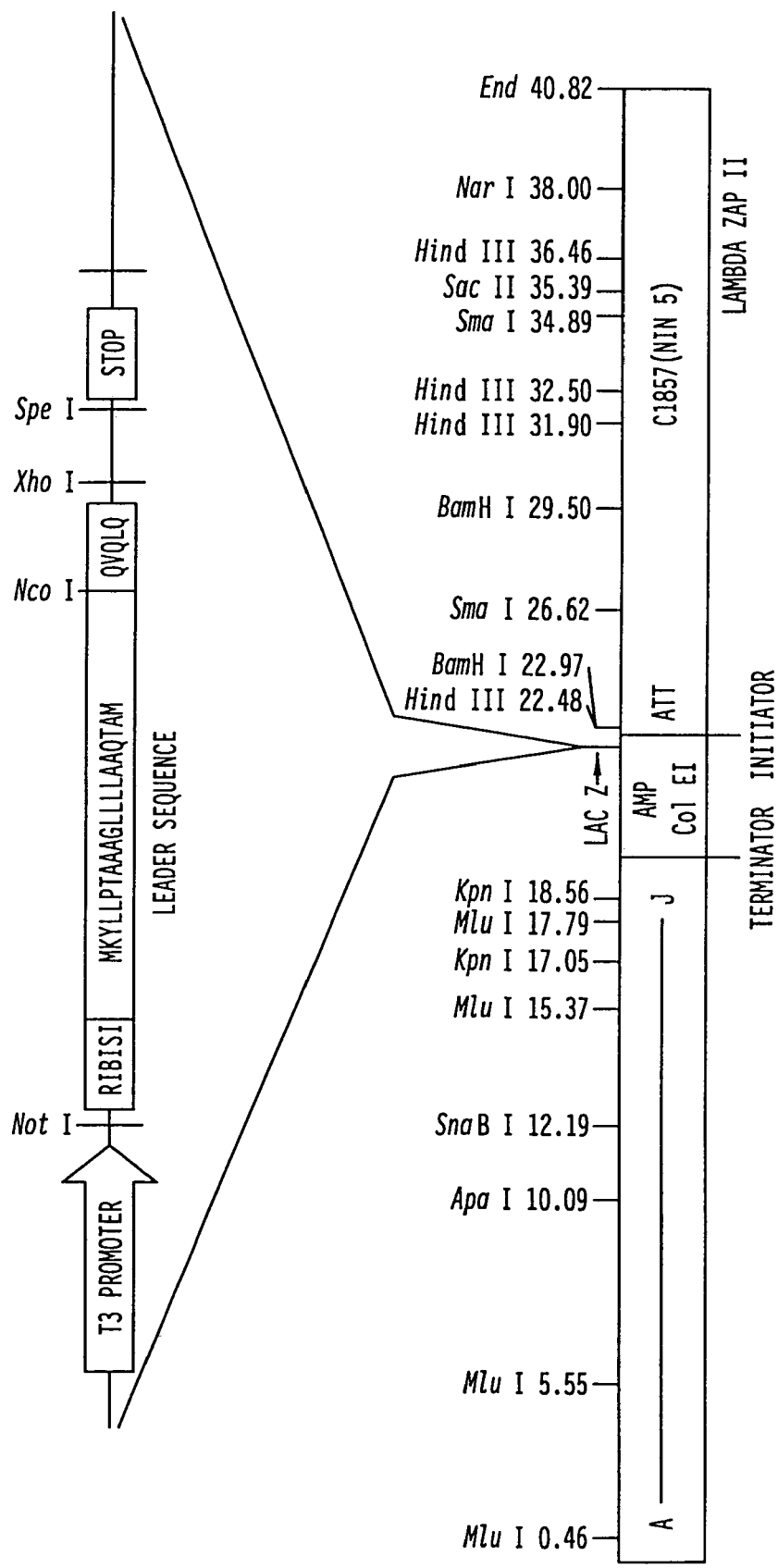
FIG. 8 The major features of the bacterial expression vector Lambda Zap II $V_L$ ($V_L$ expression vector) are shown. The synthetic sequence shown in FIG. 6 is shown at the top along with the $T_3$ polymerase promoter from Lambda Zap II. The orientation of the insert in Lambda Zap II is shown. The $V_L$ DNA homologs are inserted into the phagemid that is produced by the in vivo excision protocol described by Short et al., Nucleic Acids Res., 16:7583–7600, 1988. The $V_L$ DNA homologs are inserted into the Nco I and Spe I cloning sites of the phagemid.

Lambda Zap II $V_L$ is prepared as described in Example 12 by inserting into Lambda Zap II the synthetic DNA sequence illustrated in FIG. 6B. Important features of Lambda Zap II $V_L$ are illustrated in FIG. 8 (SEQ ID NO:39).

4. Lambda Zap II $V_L$ II

Lambda Zapp II $V_L$ II is prepared as described in Example 11 by inserting into Lambda Zap II the synthetic DNA sequence illustrated in FIG. 10.

The above-described vectors are compatible with *E. coli* hosts, i.e., they can express for secretion into the periplasm proteins coded for by genes to which they have been operatively linked for expression.

EXAMPLES

The following examples are intended to illustrate, but not limit, the scope of the invention.

1. Polynucleotide Selection

The nucleotide sequences encoding the immunoglobulin protein CDR's are highly variable. However, there are several regions of conserved sequences that flank the $V_H$ domains. For instance, contain substantially conserved nucleotide sequences, i.e., sequences that will hybridize to the same primer sequence. Therefore, polynucleotide synthesis (amplification) primers that hybridize to the conserved sequences and incorporate restriction sites into the DNA homolog produced that are suitable for operatively linking the synthesized DNA fragments to a vector were constructed. More specifically, the DNA homologs were inserted into Lambda ZAP II vector (Stratagene Cloning System, San Diego, Calif.) at the Xho I and EcoR I sites. For amplification of the $V_H$ domains, the 3' primer (primer 12 (SEQ ID NO:53) in Table 1), was designed to be complementary to the mRNA in the $J_H$ region. In all cases, the 5' primers (primers 1–10 (SEQ ID NOS:42–51), Table 1) were chosen to be complementary to the first strand cDNA in the conserved N-terminus region (antisense strand). Initially amplification was performed with a mixture of 32 primers (primer 1 (SEQ ID NO:84), Table 1) that were degenerate at five positions. Hybridoma mRNA could be amplified with mixed primers, but initial attempts to amplify mRNA from spleen yielded variable results. Therefore, several alternatives to amplification using the mixed 5' primers were compared.

The first alternative was to construct multiple unique primers, eight of which are shown in Table 1, corresponding to individual members of the mixed primer pool. The individual primers 2–9 of Table 1 (SEQ ID NOS:42–49) were constructed by incorporating either of the two possible nucleotides at three of the five degenerate positions.

The second alternative was to construct a primer containing inosine (primer 10 (SEQ ID NOS:50–51), Table 1) at four of the variable positions based on the published work of Takahashi, et al., *Proc. Natl. Acad. Sci. (U.S.A.)*, 82:1931–1935, (1985) and Ohtsuka et al., *J. Biol. Chem.*, 260: 2605–2608, (1985). This primer has the advantage that it is not degenerate and, at the same time minimizes the negative effects of mismatches at the unconserved positions as discussed by Martin et al., *Nuc. Acids Res.*, 13:8927 (1985). However, it was not known if the presence of inosine nucleotides would result in incorporation of unwanted sequences in the cloned $V_H$ regions. Therefore, inosine was not included at the one position that remains in the amplified fragments after the cleavage of the restriction sites. As a result, inosine was not in the cloned insert.

Additional, $V_H$ amplification primers including the unique 3' primer were designed to be complementary to a portion of the first constant region domain of the gamma 1 heavy chain mRNA (primers 15 and 16 (SEQ ID NOS:57–58), Table 1). These primers will produce DNA homologs containing polynucleotides coding for amino acids from the $V_H$ and the first constant region domains of the heavy chain. These DNA homologs can therefore be used to produce Fab fragments rather than an $F_V$.

As a control for amplification from spleen or hybridoma mRNA, a set of primers hybridizing to a highly conserved region within the constant region IgG, heavy chain gene were constructed. The 5' primer (primer 11 (SEQ ID NO:52), Table 1) is complementary to the cDNA in the $C_H2$ region whereas the 3' primer (primer 13 (SEQ ID NO:55), Table 1) is complementary to the mRNA in the $C_H3$ region. It is believed that no mismatches were present between these primers and their templates.

The nucleotide sequences encoding the $V_L$ CDRs are highly variable. However, there are several regions of conserved sequences that flank the $V_L$ CDR domains including the $J_L$, $V_L$ framework regions and $V_L$ leader/promoter. Therefore, amplification primers that hybridize to the conserved sequences and incorporate restriction sites that allowing cloning the amplified fragments into the pBluescript SK-vector cut with Nco I and Spe I were constructed. For amplification of the $V_L$ CDR domains, the 3' primer (primer 14 (SEQ ID NO:56) in Table 1), was designed to be complementary to the mRNA in the $J_L$ regions. The 5' primer (primer 15 (SEQ ID NO:57), Table 1) was chosen to be complementary to the first strand cDNA in the conserved N-terminus region (antisense strand).

A second set of amplification primers for amplification of the $V_L$ CDR domains the 5' primers (primers 1–8 (SEQ ID NOS:60–66 AND SEQ ID NO:121) in Table 2) were designed to be complementary to the first strand cDNA in the conserved N-terminus region. These primers also introduced a Sac I restriction endonuclease site to allow the $V_L$DNA homolog to be cloned into the $V_L$II expression vector. The 3' $V_L$ amplification primer (primer 9 (SEQ ID NO:67) in Table 2) was designed to be complementary to the mRNA in the $J_L$ regions and to introduce the Xba I restriction endonuclease site required to insert the $V_L$DNA homolog into the $V_L$II-expression vector (FIG. a).

Additional 3' $V_L$ amplification primers were designed to hybridize to the constant region of either kappa or lambda mRNA (primers 10 and 11 (SEQ ID NOS:68–69) in Table 2). These primers allow a DNA homolog to be produced containing polynucleotide sequences coding for constant region amino acids of either kappa or lambda chain. These primers make it possible to produce an Fab fragment rather than an $F_V$.

The primers used for amplification of kappa light chain sequences for construction of Fabs are shown at least in Table 2. Amplification with these primers was performed in 5 separate reactions, each containing one of the 5' primers (primers 3–6 (SEQ ID NOS:62–65), and 12 (SEQ ID NO:70)) and one of the 3' primers (primer 13). The remaining 3' primer (primer 9 (SEQ ID NO:67)) has been used to construct Fv fragments. The 5' primers contain a Sac I restriction site and the 3' primers contain a Xba I restriction site.

The primers used for amplification of heavy chain Fd fragments for construction of Fabs are shown at least in Table 1. Amplification was performed in eight separate reactions, each containing one of the 5' primers (primers 2–9 (SEQ ID NOS:42–49)) and one of the 3' primers (primer 15 (SEQ ID NO:57)). The remaining 5' primers that have been used for amplification in a single reaction are either a degenerate primer (primer I (SEQ ID NO:84)) or a primer that incorporates inosine at four degenerate positions (primer 10 (SEQ ID NOS:50–51), Table 1, and primers 17 and 18, Table 2 (SEQ ID NOS:75–76)). The remaining 3' primer (primer 14 (SEQ ID NO:72), Table 2) has been used to construct $F_V$ fragments. Many of the 5' primers incorporate a Xho I site, and the 3' primers include a Spe I restriction site.

$V_H$ amplification primers designed to amplify human heavy chain variable regions are shown in Table 2. The 5' heavy chain primer contains inosine residues at degenerate nucleotide positions allowing a single primer to hybridize to a large number of variable region sequences. Primers designed to hybridize to the constant region sequences of various IgG mRNAs are also shown in Table 2.

$V_L$ amplification primers designed to amplify human light chain variable regions of both the lambda and kappa isotypes are also shown in Table 2.

All primers and synthetic polynucleotides used herein and shown on Tables 1–4 were either purchased from Research Genetics in Huntsville, Ala. or synthesized on an Applied Biosystems DNA synthesizer, model 381A, using the manufacturer's instruction.

TABLE 1

| | | | |
|---|---|---|---|
| (1) | 5' AGGTSMARCTKCTCGAGTCWGG 3' | (SEQ ID NO:84) | degenerate 5' primer for the amplification of variable heavy chain region ($V_H$) |
| (2) | 5' AGGTCCAGCTGCTCGAGTCTGG 3' | (SEQ ID NO:42) | Unique 5' primer for the amplification of $V_H$ |
| (3) | 5' AGGTCCAGCTGCTCGAGTCAGG 3' | (SEQ ID NO:43) | Unique 5' primer for the amplification of $V_H$ |
| (4) | 5' AGGTCCAGCTTCTCGAGTCTGG 3' | (SEQ ID NO:44) | Unique 5' primer for the amplification of $V_H$ |
| (5) | 5' AGGTCCAGCTTCTCGAGTCAGG 3' | (SEQ ID NO:45) | Unique 5' primer for the amplification of $V_H$ |
| (6) | 5' AGGTGCAACTGCTCGAGTCTGG 3' | (SEQ ID NO:46) | Unique 5' primer for the amplification of $V_H$ |
| (7) | 5' AGGTCCAACTGCTCGAGTCAGG 3' | (SEQ ID NO:47) | Unique 5' primer for the amplification of $V_H$ |
| (8) | 5' AGGTCCAACTTCTCGAGTCTGG 3' | (SEQ ID NO:48) | Unique 5' primer for the amplification of $V_H$ |
| (9) | 5' AGGTCCAACTTCTCGAGTCAGG 3' | (SEQ ID NO:49) | Unique 5' primer for the amplification of $V_H$ |
| (10) | 5' AGGTIIAICTICTCGAGTCT3' | (SEQ ID NO:50) | 5' degenerate primer containing inosine at 4 degenerate positions |
| (10) | 5' AGGTIIAICTICTCGAGTC(A)3' | (SEQ ID NO:51) | 5' degenerate primer containing inosine at 4 degenerate positions |
| (11) | 5' GCCCAAGGATGTGCTCACC 3' | (SEQ ID NO:52) | 5' primer for amplification in the $C_H2$ region of mouse IgG1 |
| (12) | 5' CTATTAGAATTCAACGGTAACAGTGGTGCCTTGGCCCCA 3' | (SEQ ID NO:53) | 3' primer for amplification of $V_H$ |
| (12A) | 5' CTATTAACTAGTAACGGTAACAGTGGTGCCTTGGCCCCA 3' | (SEQ ID NO:54) | 3' primer for amplification of $V_H$ using 3' Spe I site |
| (13) | 5' CTCAGTATGGTGGTTGTGC 3' | (SEQ ID NO:55) | 3' primer for amplification in the $C_H3$ region of mouse IgG1 |
| (14) | 5' GCTACTAGTTTTGATTTCCACCTTGG 3' | (SEQ ID NO:56) | 3' primer for amplification of $V_L$ |
| (15) | 5' CAGCCATGGCCGACATCCAGATG 3' | (SEQ ID NO:57) | 5' primer for amplification of $V_L$ |
| (16) | 5' AATTTTACTAGTCACCTTGGTGCTGCTGGC 3' | (SEQ ID NO:58) | Unique 3' primer for amplification of $V_H$ including part of the mouse gamma 1 first constant |
| (17) | 5' TATGCAACTAGTACAACCACAATCCCTGGGCACAATTTT 3' | (SEQ ID NO:59) | Unique 3' primer for amplification of $V_H$ including part of mouse gamma 1 first constant region and hinge region |

TABLE 2

| | | | |
|---|---|---|---|
| (1) | 5' CCAGTTCCGAGCTCGTTGTGACTCAGGAATCT 3' | (SEQ ID NO:60) | Unique 5' primer for the amplification of $V_L$ |
| (2) | 5' CCAGTTCCGAGCTCGTGTTGACGCAGCCGCCC 3' | (SEQ ID NO:61) | Unique 5' primer for the amplification of $V_L$ |
| (3) | 5' CCAGTTCCGAGCTCGTGCTCACCCAGTCTCCA 3' | (SEQ ID NO:62) | Unique 5' primer for the amplification of $V_L$ |
| (4) | 5' CCAGTTCCGAGGTCCAGATGACCCAGTCTCCA 3' | (SEQ ID NO:63) | Unique 5' primer for the amplification of $V_L$ |
| (5) | 5' CCAGATGTGAGCTCGTGATGACCCAGACTCCA 3' | (SEQ ID NO:64) | Unique 5' primer for the amplification of $V_L$ |
| (6) | 5' CCAGATGTGAGCTCGTCATGACCCAGTCTCCA 3' | (SEQ ID NO:65) | Unique 5' primer for the amplification of $V_L$ |
| (7) | 5' CCAGATGTGAGCTCTTGATGAGCCAAACTCAA 3' | (SEQ ID NO:66) | Unique 5' primer for the amplification of $V_L$ |
| (8) | 5' CCAGATGTGAGCTCGTGATAACCCAGGATGAA 3' | (SEQ ID NO:121) | Unique 5' primer for the amplification of $V_L$ |
| (9) | 5' GCAGCATTCTAGAGTTTCAGCTCCAGCTTGCC 3' | (SEQ ID NO:67) | Unique 3' primer for $V_L$ amplification |

TABLE 2-continued

| | | | |
|---|---|---|---|
| (10) | 5' CCGCCGTCTAGAACACTCATTCCTGTTGAAGCT 3' | (SEQ ID NO:68) | Unique 3' primer for $V_L$ amplification including the kappa constant region |
| (11) | 5' CCGCCGTCTAGAACATTCTGCAGGAGACAGACT 3' | (SEQ ID NO:69) | Unique 3' primer for $V_L$ amplification including the lambda constant region |
| (12) | 5' CCAGTTCCGAGCTCGTGATGACACAGTCTCCA 3' | (SEQ ID NO:70) | Unique 5' primer for $V_L$ amplification |
| (13) | 5' GCGCCGTCTAGAATTAACACTCATTCCTGTTGAA 3' | (SEQ ID NO:71) | Unique 3' primer for $V_L$ amplification |
| (14) | 5' CTATTAACTAGTAACGGTAACAGTGGTGCCTTGCC CCA 3' | (SEQ ID NO:72) | Unique 3' primer for $V_L$ amplification |
| (15) | 5' AGGCTTACTAGTACAATCCCTGGGCACAAT 3' | (SEQ ID NO:73) | Unique 3' primer for $V_H$ amplification |
| (16) | 5' GCCGCTCTAGAACACTCATTCCTGTTGAA 3' | (SEQ ID NO:74) | Unique 3' primer for $V_L$ amplification |
| (17) | 5' AGGTIIAICTICTCGAGTCTGC 3' | (SEQ ID NO:75) | Degenerate 5' primer containing inosine at 4 degenerate positions |
| (18) | 5' AGGTIIAICTICTCGAGTCAGC 3' | (SEQ ID NO:76) | Degenerate 5' primer containing inosine at 4 degenerate positions |
| (19) | 5' GTGCCAGATGTGAGCTCGTGATGACCCAGTCTCCA 3' | (SEQ ID NO:77) | Unique 5' primer for human kappa $V_L$ amplification |
| (20) | 5' TCCTTCTAGATTACTAACACTCTCCCCTGTTGAA 3' | (SEQ ID NO:78) | Unique 3' primer for human kappa $V_L$ amplification |
| (21) | 5' GCATTCTAGACTATTAACATTCTGTAGGGGC 3' | (SEQ ID NO:79) | Unique 3' primer for human lambda $V_L$ amplification |
| (22) | 5' CTGCACAGGGTCCTGGGCCGAGCTCGTGGTGACTC AG 3' | (SEQ ID NO:80) | Unique 5' primer for human lambda $V_L$ amplification |
| (23) | 5' AGITGCAIITGCTCGAGTCTGG 3' | (SEQ ID NO:81) | 5' degenerate primer for human $V_H$ amplification containing inosine at 3 degenerate positions |
| (24) | 5' GTGGGCATGTGTGAGTTGTGTCACTAGTTGGGGTT TTGAGCTC 3' | (SEQ ID NO:82) | Unique 3' primer for human $V_H$ amplification |
| (25) | 5' CGGACTAGTACAAGATTTGGGCTCTGCTTT 3' | (SEQ ID NO:83) | Unique 3' primer for human IgG1 $V_H$ amplification |

2. Production of a $V_H$ Coding Repertoire Enriched in FITC Binding Proteins

Fluorescein isothiocyanate (FITC) was selected as a ligand for receptor binding. It was further decided to enrich by immunization the immunological gene repertoire, i.e., $V_H$- and $V_L$-coding gene repertoires, for genes coding for anti-FITC receptors. This was accomplished by linking FITC to keyhole limpet hemocyanin (KLH) using the techniques described in Antibodies A Laboratory Manual, Harlow and Lowe, eds., Cold Spring Harbor, N.Y., (1988). Briefly, 10.0 milligrams (mg) of keyhold limpet hemocyanin and 0.5 mg of FITC were added to 1 ml of buffer containing 0.1 M sodium carbonate at pH 9.6 and stirred for 18 to 24 hours at 4 degrees C. (4 C). The unbound FITC was removed by gel filtration through Sephadex G-25.

The KLH-FITC conjugate was prepared for injection into mice by adding 100 μg of the conjugate to 250 μl of phosphate buffered saline (PBS). An equal volume of complete Freund's adjuvant was added and emulsified the entire solution for 5 minutes. A 129 $G_{1X+}$ mouse was injected with 300 μl of the emulsion. Injections were given subcutaneously at several sites using a 21 gauge needle. A second immunization with KLH-FITC was given two weeks later. This injection was prepared as follows: fifty μg of KLH-FITC were diluted in 250 μL of PBS and an equal volume of alum was admixed to the KLH-FITC solution. The mouse was injected intraperitoneally with 500 μl of the solution using a 23 gauge needle. One month later the mice were given a final injection of 50 μg of the KLH-FITC conjugate diluted to 200 μL in PBS. This injection was given intravenously in the lateral tail vein using a 30 gauge needle. Five days after this final injection the mice were sacrificed and total cellular RNA was isolated from their spleens.

Hybridoma PCP 8D11 producing an antibody immunospecific for phosphonate ester was cultured in DMEM media (Gibco Laboratories, Grand Island, N.Y.) containing 10 percent fetal calf serum supplemented with penicillin and streptomycin. About $5 \times 10^8$ hybridoma cells were harvested and washed twice in phosphate buffered saline. Total cellular RNA was prepared from these isolated hybridoma cells.

3. Preparation of a $V_H$-Coding Gene Repertoire

Total cellular RNA was prepared from the spleen of a single mouse immunized with KLH-FITC as described in Example 2 using the RNA preparation methods described by Chomczynski et al., Anal Biochem., 162:156–159 (1987) using the manufacturer's instructions and the RNA isolation kit produced by Stratagene Cloning Systems, La Jolla, Calif. Briefly, immediately after removing the spleen from the immunized mouse, the tissue was homogenized in 10 ml of a denaturing solution containing 4.0 M guanine isothiocyanate, 0.25 M sodium citrate at pH 7.0, and 0.1 M 2-mercaptoethanol using a glass homogenizer. One ml of sodium acetate at a concentration of 2 M at pH 4.0 was admixed with the homogenized spleen. One ml of phenol that had been previously saturated with $H_2O$ was also admixed to the denaturing solution containing the homogenized spleen. Two ml of a chloroform:isoamyl alcohol (24:1 v/v) mixture was added to this homogenate. The homogenate was mixed vigorously for ten seconds and maintained on ice for 15 minutes. The homogenate was then transferred to a thick-walled 50 ml polypropylene centrifuged tube (Fisher Scientific Company, Pittsburg, Pa.). The solution was centrifuged at 10,000×g for 20 minutes at 4 C. The upper RNA-containing aqueous layer was transferred to a fresh 50 ml polypropylene centrifuge tube and mixed with an equal volume of isopropyl alcohol. This solution was maintained at −20 C for at least one hour to precipitate the RNA. The solution containing the precipitated RNA was centrifuged at 10,000×g for twenty minutes at 4 C. The pelleted total cellular RNA was collected and dissolved in 3 ml of the denaturing solution described above. Three ml of isopropyl alcohol was added to the resuspended total cellular RNA and vigorously mixed. This solution was maintained at −20 C for at least 1 hour to precipitate the RNA. The solution containing the precipitated RNA was centrifuged at 10,000×g for ten minutes at 4 C. The pelleted RNA was washed once with a solution containing 75% ethanol. The pelleted RNA was dried under vacuum for 15 minutes and then resuspended in dimethylpyrocarbonate (DEPC) treated (DEPC—$H_2O$)$H_2O$.

Messenger RNA (mRNA) enriched for sequences containing long poly A tracts was prepared from the total cellular RNA using methods described in *Molecular Cloning A Laboratory Manual*, Maniatias et al., eds., Cold Spring Harbor Laboratory, New York, (1982). Briefly, one half of the total RNA isolated from a single immunized mouse spleen prepared as described above was resuspended in one ml of DEPC—$H_2O$ and maintained at 65 C for five minutes. One ml of 2× high salt loading buffer consisting of 100 mM Tris-HCl, 1 M sodium chloride, 2.0 mM disodium ethylene diamine tetraacetic acid (EDTA) at pH 7.5, and 0.2% sodium dodecyl sulfate (SDS) was added to the resuspended RNA and the mixture allowed to cool to room temperature. The mixture was then applied to an oligo-dT (Collaborative Research Type 2 or Type 3) column that was previously prepared by washing the oligo-dT with a solution containing 0.1 M sodium hydroxide and 5 mM EDTA and then equilibrating the column with DEPC—$H_2O$. The eluate was collected in a sterile polypropylene tube and reapplied to the same column after heating the eluate for 5 minutes at 65 C. The oligo dT column was then washed with 2 ml of high salt loading buffer consisting of 50 mM Tris-HCl at pH 7.5, 500 mM sodium chloride, 1 mM EDTA at pH 7.5 and 0.1% SDS. The oligo dT column was then washed with 2 ml of 1× medium salt buffer consisting of 50 mM Tris-HCl at pH 7.5, 100 mM sodium chloride 1 mM EDTA and 0.1% SDS. The messenger RNA was eluted from the oligo dT column with 1 ml of buffer consisting of 10 mM Tris-HCl at pH 7.5, 1 mM EDTA at pH 7.5 and 0.05% SDS. The messenger RNA was purified by extracting this solution with phenol/chloroform followed by a single extraction with 100% chloroform. The messenger RNA was concentrated by ethanol precipitation and resuspended in DEPC $H_2O$.

The messenger RNA isolated by the above process contains a plurality of different $V_H$ coding polynucleotides, i.e., greater than about $10^4$ different $V_H$-coding genes.

4. Preparation of a Single $V_H$ Coding Polyuclectide

Polynucleotides coding for a single $V_H$ were isolated according to Example 3 except total cellular RNA was extracted from monoclonal hybridoma cells prepared in Example 2. The polynucleotides isolated in this manner code for a single $V_H$.

5. DNA Homolog Preparation

In preparation for PCR amplification, mRNA prepared according to the above examples was used as a template for cDNA synthesis by a primer extension reaction. In a typical 50 µl transcription reaction, 5–10 ug of spleen or hybridoma mRNA in water was first hybridized (annealed) with 500 ng (50.0 pmol) of the 3' $V_H$ primer (primer 12 (SEQ ID NO:53) Table 1), at 65° C. for five minutes. Subsequently, the mixture was adjusted to 1.5 mM dATP, dCTP, dGTP and dTTP, 40 mM Tris-HCl at pH 8.0, 8 mM $MgCl_2$, 50 mM NaCl, and 2 mM spermidine. Moloney-Murine Leukemia virus Reverse transcriptase (Stratagene Cloning Systems), 26 units, was added and the solution was maintained for 1 hour at 37° C.

PCR amplification was performed in a 100 ul reaction containing the products of the reverse transcription reaction (approximately 5 ug of the cDNA/RNA hybrid), 300 ng of 3' $V_H$ primer (primer 12 (SEQ ID NO:53) of Table 1), 300 ng each of the 5' $V_H$ primers (primer 2–10 (SEQ ID NOS:42–51) of Table 1) 200 mM of a mixture of dNTP's, 50 mM KCl, 10 mM Tris-HCl pH 8.3, 15 mM $MgCl_2$, 0.1% gelatin and 2 units of Taq DNA polymerase. The reaction mixture was overlaid with mineral oil and subjected to 40 cycles of amplification. Each amplification cycle involved denaturation at 92° C. for 1 minute, annealing at 52° C. for 2 minutes and polynucleotide synthesis by Primer extension (elongation) at 72° C. for 1.5 minutes. The amplified $V_H$-coding DNA homolog containing samples were extracted twice with phenol/chloroform, once with chloroform, ethanol precipitated and were stored at −70° C. in 10 mM Tris-HCl, (pH, 7.5) and 1 mM EDTA.

Figure 1:
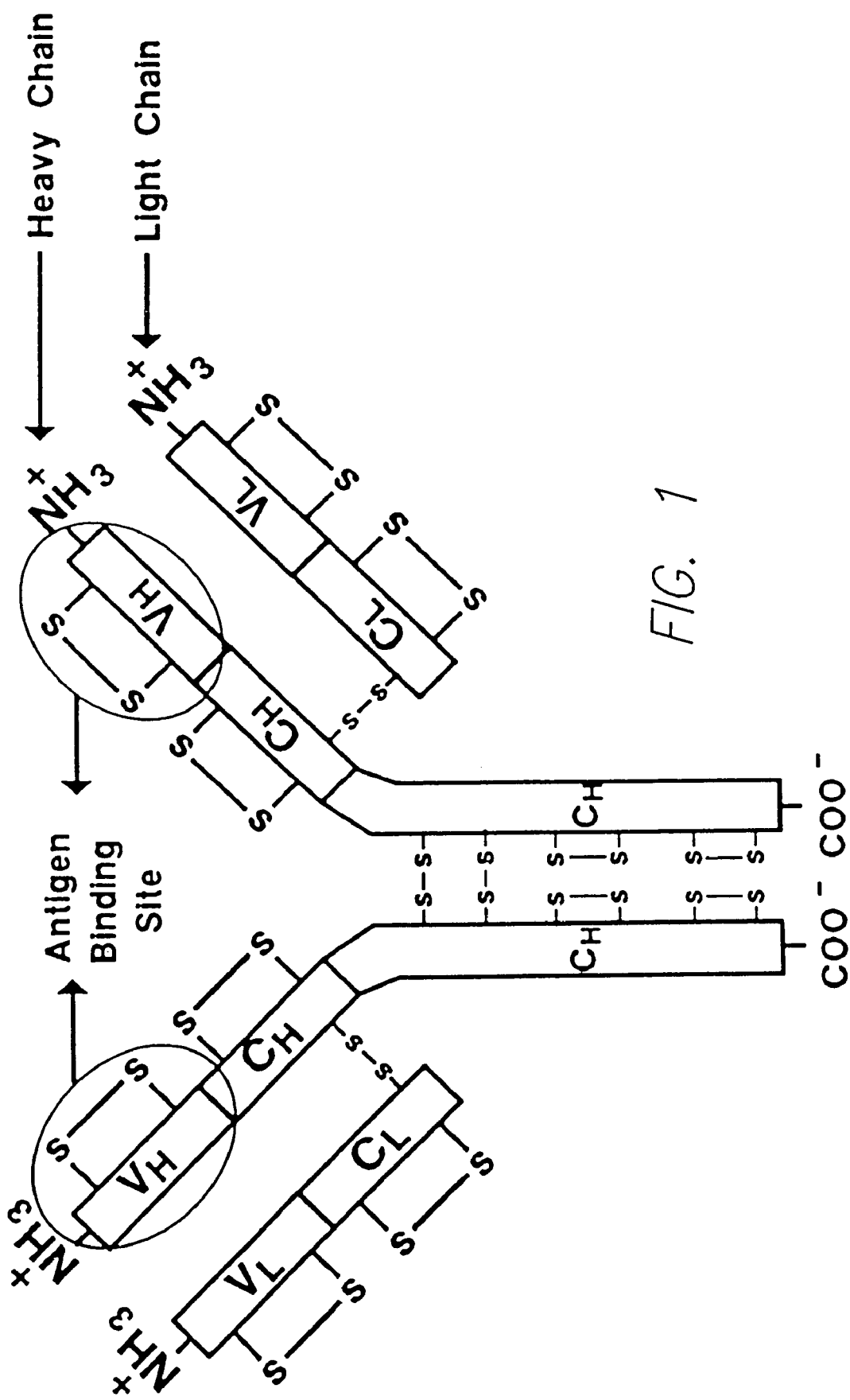
FIG. 1 Illustrates a schematic diagram of the immunoglobulin molecule showing the principal structural features. The circled area on the heavy chain represents the variable region ($V_H$), a polypeptide containing a biologically active (ligand binding) portion of that region, and a gene coding for that polypeptide, are produced by the methods of the present invention. Sequences L03, L35, L47 and L48 could not be classified into any predefined subgroups.
Figures 1, 2A:
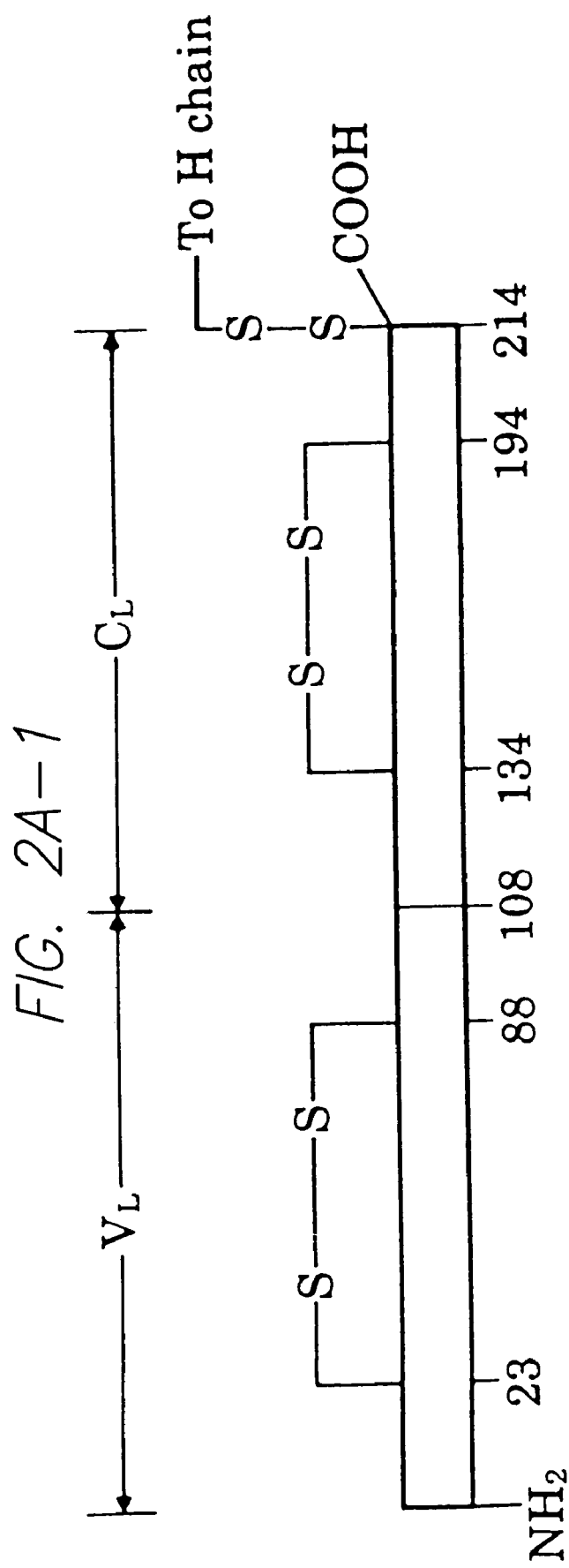
FIG. 2A Diagrammatic sketch of an H chain of human IgG (IgG1 subclass). Numbering is from the N-terminus on the left to the C-terminus on the right. Note the presence of four domains, each containing an intrachain disulfide bond (S—S) spanning approximately 60 amino acid residues. The symbol CHO stands for carbohydrate. The V region of the heavy (H) chain ($V_H$) resembles $V_L$ in having three hypervariable CDR (not shown).
Figures 2, 2A:
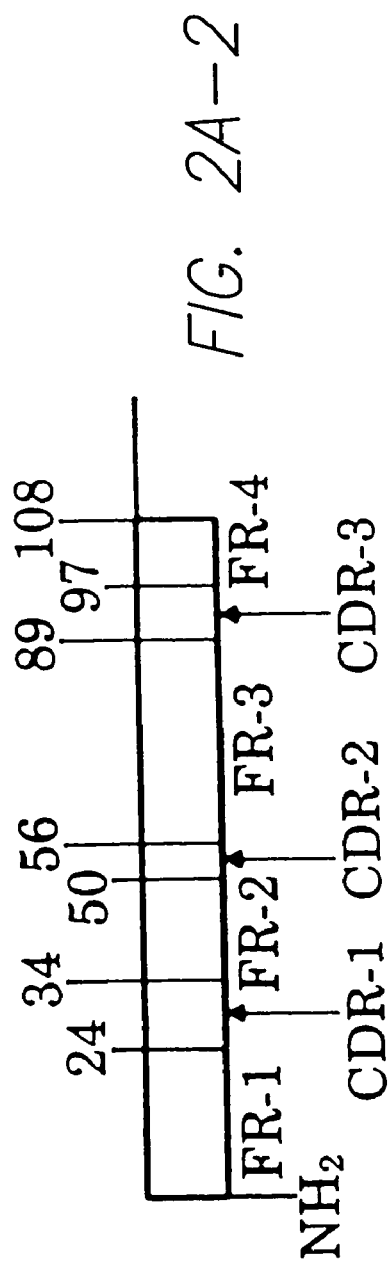
Figure 2B:
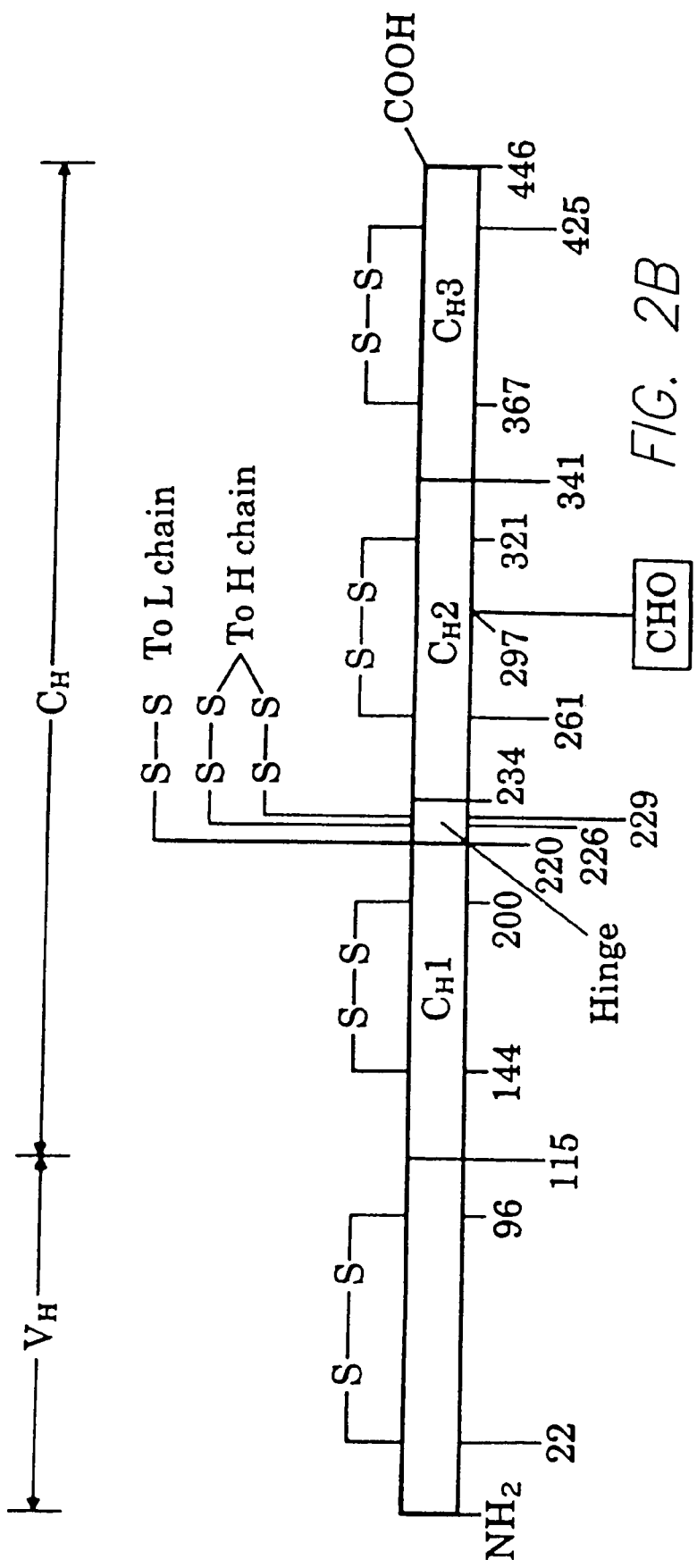
FIG. 2B Diagrammatic sketch of a human K chain (Panel 1). Numbering is from the N-terminus on the left to the C-terminus on the right. Note the intrachain disulfide bond (S—S) spanning about the same number of amino acid residues in the $V_L$ and $C_L$ domains. Panel 2 shows the locations of the complementarity-determining regions (CDR) in the $V_L$ domain. Segments outside the CDR are the framework segments (FR).
Figures 2, 3:
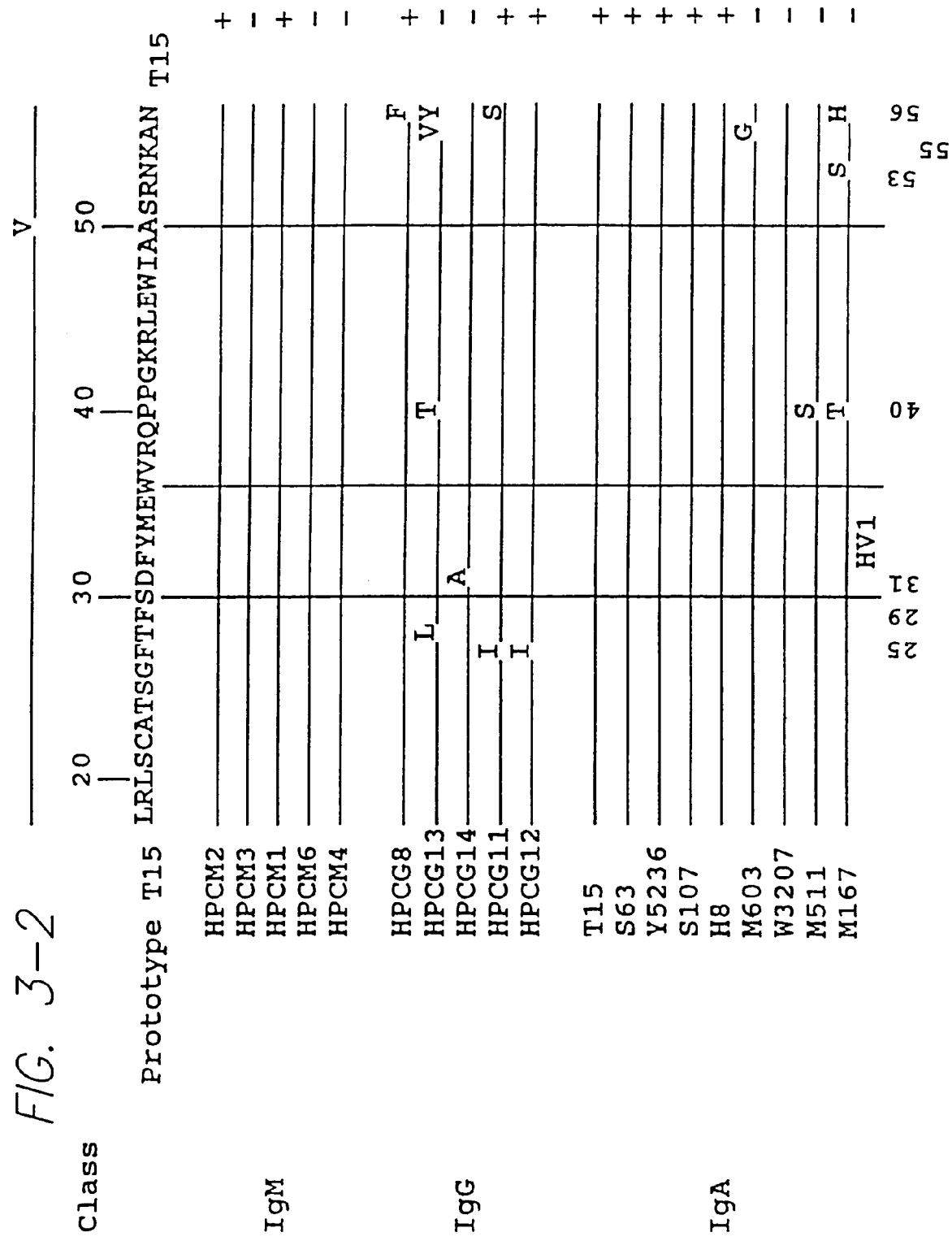
FIG. 3 Amino acid sequence of the $V_H$ regions of 19 mouse monoclonal antibodies with specificity for phosphorylcholine (SEQ ID NOS:1–9). The designation HP indicates that the protein is the product of a hybridoma. The remainder are myeloma proteins. (From Gearhart et al., Nature, 291:29, 1981.)
Figure 3:
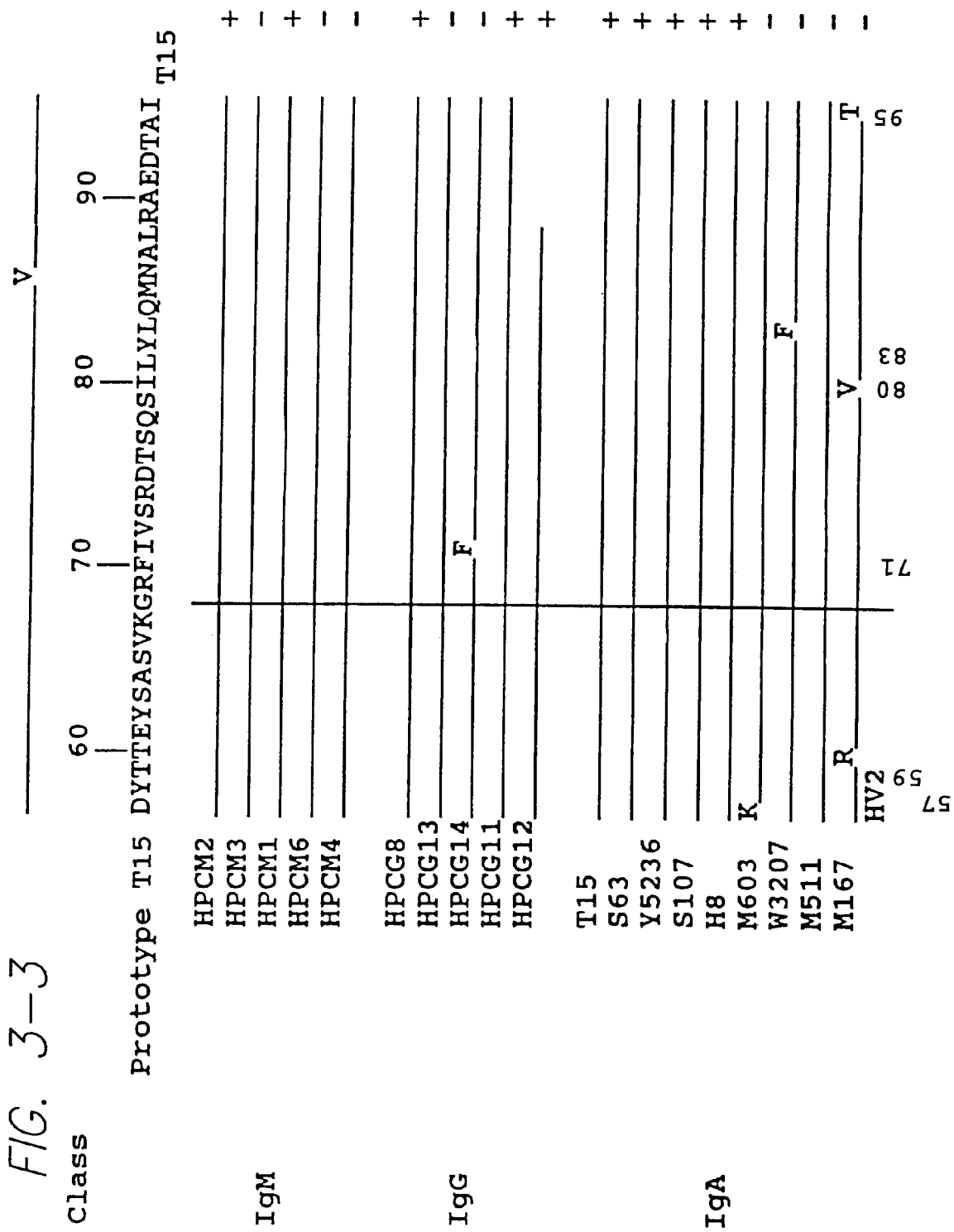

Using unique 5' primers (2–9 (SEQ ID NOS:42–49), Table 1), efficient $V_H$-coding DNA homolog synthesis and amplification from the spleen mRNA was achieved as shown in FIG. 3, lanes R17–R24. The amplified cDNA ($V_H$-coding DNA homolog) is seen as a major band of the expected size (360 bp). The intensities of the amplified $V_H$-coding polynucleotide fragment in each reaction appear to be similar, indicating that all of these primers are about equally efficient in initiating amplification. The yield, and quality of the amplification with these primers was reproducible.

Figure 4:
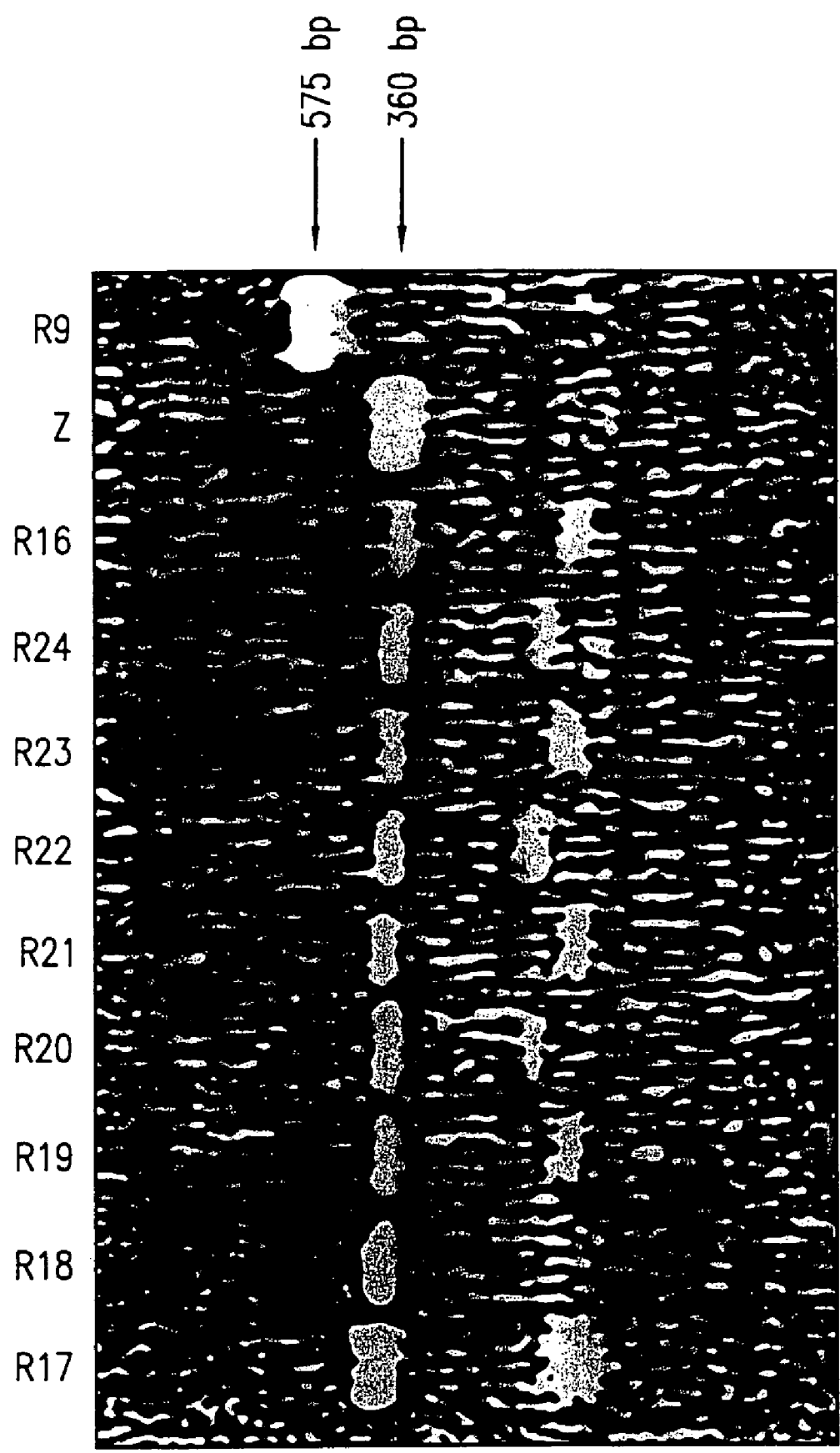
FIG. 4 Illustrates the results obtained from PCR amplification of mRNA obtained from the spleen of a mouse immunized with FITC. Lanes R17–R24 correspond to amplification reactions with the unique 5' primers (2–9, Table 1) and the 3' primer (12, Table 1), R16 represents the PCR reaction with the 5' primer containing inosine (10, Table 1) and 3' primer (12, Table 1). Z and R9 are the amplification controls; control Z involves the amplification of $V_H$ from a plasmid (PLR2) and R9 represents the amplification from the constant regions of spleen mRNA using primers 11 and 13 (Table 1).

The primer containing inosine also synthesized amplified $V_H$-coding DNA homologs from spleen mRNA reproducibly, leading to the production of the expected sized fragment, of an intensity similar to that of the other amplified cDNAs (FIG. 4, Lane R16). This result indicated that the presence of inosine also permits efficient DNA homolog synthesis and amplification. Clearly indicating how useful such primers are in generating a plurality of $V_H$-coding DNA homologs. Amplification products obtained from the constant region primers (primers 11 and 13 (SEQ ID NOS:52 & 55), Table 1) were more intense indicating that amplification was more efficient, possibly because of a higher degree of homology between the template and primers (FIG. 4, Lane R9). Based on these results, a $V_H$-coding gene library was constructed from the products of eight amplifications, each performed with a different 5' primer. Equal portions of the products from each primer extension reaction were mixed and the mixed product was then used to generate a library of $V_H$-coding DNA homolog-containing vectors.

DNA homologs of the $V_L$ were prepared from the purified mRNA prepared as described above. In preparation for PCR amplification, mRNA prepared according to the above examples was used as a template for cDNA synthesis. In a typical 50 ul transcription reaction, 5–10 ug of spleen or hybridoma mRNA in water was first annealed with 300 ng (50.0 pmol) of the 3' $V_L$ primer (primer 14 (SEQ ID NO:56), Table 1), at 65° C. for five minutes. Subsequently, the mixture was adjusted to 1.5 mM dATP, dCTP, dGTP, and dTTY, 40 mM Tris-HCl at pH 8.0, 8 mM $MgCl_2$, 50 mM NaCl, and 2 mM spermidine. Moloney-Murine Leukemia virus reverse transcriptase (Stratagene Cloning Systems), 26 units, was added and the solution was maintained for 1 hour at 37° C. The PCR amplification was performed in a 100 ul reaction containing approximately 5 ug of the cDNA/RNA hybrid produced as described above, 300 ng of the 3' $V_L$ primer (primer 14 (SEQ ID NO:56) of Table 1), 300 ng of the 5' $V_L$ primer (primer 15 (SEQ ID NO:57) of Table 1), 200 mM of a mixture of dNTP's, 50 mM KCl, 10 mM Tris-HCl pH 8.3, 15 MM $MgCl_2$, 0.1% gelatin and 2 units of Taq DNA polymerase. The reaction mixture was overlaid with mineral oil and subjected to 40 cycles of amplification. Each amplification cycle involved denaturation at 92° C. for 1 minute, annealing at 52° C. for 2 minutes and elongation at 72° C. for 1.5 minutes. The amplified samples were extracted twice with phenol/chloroform, once with chloroform, ethanol precipitated and were stored at −70° C. in 10 mM Tris-HCl at 7.5 and 1 mM EDTA.

6. Inserting DNA Homologs into Vectors

In preparation for cloning a library enriched in $V_H$ sequences, PCR amplified products (2.5 mg/30 ul of 150 mM NaCl, 8 mM Tris-HCl (pH 7.5), 6 mM $MgSO_4$, 1 mM DTT, 200 mg/ml bovine serum albumin (BSA) at 37 C were digested with restriction enzymes Xho 1 (125 units) and EcoR 1 (10 U) and purified on a 1% agarose gel. In cloning experiments which required a mixture of the products of the amplification reactions, equal volumes (50 ul, 1–10 ug concentration) of each reaction mixture were combined after amplification but before restriction digestion. After gel electrophoresis of the digested PCR amplified spleen mRNA, the region of the gel containing DNA fragments of approximately 350 bps was excised, electroeluted into a dialysis membrane, ethanol precipitated and resuspended in 10 mM Tris-HCl pH 7.5 and 1 mM EDTA to a final concentration of 10 ng/u 1. Equimolar amounts of the insert were then ligated overnight at 5 C to 1 ug of Lambda ZAP™ II vector (Stratagene Cloning Systems, La Jolla, Calif.) previously cut by EcoR I and Xho I. A portion of the ligation mixture (1 ul) was packaged for 2 hours at room temperature using Gigapack Gold packaging extract (Stratagene Cloning Systems, La Jolla, Calif.), and the packaged material was plated on XL1-blue host cells. The library was determined to consist of $2\times10^7$ $V_H$ homologs with less than 30% non-recombinant background.

The vector used above, Lambda Zap II is a derivative of the original Lambda Zap (ATCC # 40,298) that maintains all of the characteristics of the original Lambda Zap including 6 unique cloning sites, fusion protein expression, and the ability to rapidly excise the insert in the form of a phagemid (Bluescript SK−), but lacks the SAM 100 mutation, allowing growth on many Non-Sup F strains, including XL1-Blue. The Lambda Zap II was constructed as described in Short et al., *Nucleic Acids Res.*, 16:7583–7600, 1988, by replacing the Lambda S gene contained in a 4254 base pair (bp) DNA fragment produced by digesting Lambda Zap with the restriction enzyme NcoI. This 4254 by DNA fragment was replaced with the 4254 by DNA fragment containing the Lambda S gene isolated from Lambda gt10 (ATCC #40,179) after digesting the vector with the restriction enzyme NcoI. The 4254 bp DNA fragment isolated from lambda gt10 was ligated into the original Lambda Zap vector using T4 DNA ligase and standard protocols for such procedures described in *Current Protocols in Molecular Biology*, Ausubel et al., eds., John Wiley and Sons, New York, 1987.

In preparation of cloning a library enriched in $V_L$ sequences, 2 ug of PCR amplified products (2.5 mg/30 ul of 150 mM NaCl, 8 mM Tris-HCl (pH 7.5), 6 mM $MgSO_4$, 1 mM DTT, 200 mg/ml BSA. 37 C) were digested with restriction enzymes Nco 1 (30 units) and Spe 1 (45 units). The digested PCR amplified products were purified on a 1% agarose gel using standard electroelution technique described in *Molecular Cloning A Laboratory Manual*, Maniatis et al., eds., Cold Spring Harbor, N.Y., (1982). Briefly, after gel electroelution of the digested PCR amplified product the region of the gel containing the $V_L$-coding DNA fragment of the appropriate size was excised, electroelution into a dialysis membrane, ethanol precipitated and resuspended at a final concentration of 10 ng per ml in a solution containing 10 mM Tris-HCl at pH 7.5 and 1 mM EDTA.

An equal molar amount of DNA representing a plurality of different $V_L$-coding DNA homologs was ligated to a pBluescript SK− phagemid vector that had been previously cut with Nco I and Spe I. A portion of the ligation mixture was transformed using the manufacturer's instructions into Epicuian Coli XL1-Blue competent cells (Stragagene Cloning Systems, La Jolla, Calif.). The transformant library was determined to consist of $1.2\times10^3$ colony forming units/ug of $V_L$ homologs with less than 3% non-recombinant background.

7. Sequencing of Plasmids from the $V_H$-Coding cDNA Library

To analyze the Lambda Zap II phage clones the clones were excised from Lambda Zap into plasmids according to the manufacture's instructions (Stratagene Cloning System, La Jolla, Calif.). Briefly, phage plaques were cored from the agar plates and transferred to sterile microfuge tubes containing 500 μl a buffer containing 50 mM Tris-HCl at pH 7.5, 100 mM NaCl, 10 mM $MgSO_4$, and 0.01% gelatin and 20 uL of 15 chloroform.

For excisions, 200 ul of the phage stock, 200 ul of XL1-Blue cells ($A_{600}$=1.00) and 1 ul of R408 helper phage ($1\times10^{11}$ pfu/ml) were incubated at 37 C for 15 minutes. The excised plasmids were infected into XL1-Blue cells and plated onto LB plates containing ampicillin. Double stranded DNA was prepared from the phagemid containing cells according to the methods described by Holmes et al., *Anal. Biochem.*, 14:193, (1981). Clones were first screened for DNA inserts by restriction digests with either Pvu II or Bgl I and clones containing the putative $V_H$ insert were sequenced using reverse transcriptase according to the general method described by Sanger et al., *Proc. Natl. Acad. Sci, USA*, 74:5463–5467, (1977) and the specific modifications of this method provided in the manufacturer's instructions in the AMV reverse transcriptase $^{35}$S-dATP sequencing kit from Stratagene Cloning Systems, La Jolla, Calif.

8. Characterization of the Cloned $V_H$ Repertoire

The amplified products which had been digested with Xho I and EcoR I and cloned into Lambda ZAP, resulted in a cDNA library with $9.0\times10^5$ pfu's. In order to confirm that the library consisted of a diverse population of $V_H$-coding DNA homologs, the N-terminal 120 bases of 18 clones, selected at random from the library, were excised and sequenced (FIG. 5). To determine if the clones were of $V_H$ gene origin, the cloned sequences were compared with known $V_H$ sequences and $V_L$ sequences. The clones exhibited from 80 to 90% homology with sequences of known heavy chain origin and little homology with sequences of light chain origin when compared with the sequences available in *Sequences of Proteins of Immunological Interest* by Kabot et al., 4th ed., U.S. Dept. of Health and Human Sciences, (1987). This demonstrated that the library was enriched for the desired $V_H$ sequence in preference to other sequences, such as light chain sequences.

The diversity of the population was assessed by classifying the sequenced clones into predefined subgroups (FIG. 5 (SEQ ID NOS:20–37)). Mouse $V_H$ sequences are classified into eleven subgroups (FIG. 5). Mouse $V_H$ sequences are classified into eleven subgroups (I (A,B,), II (A,B,C), m (A,B,C,D,) V (A,B)] based on framework amino acid sequences described in *Sequences of Proteins of Immunological Interest* by Kabot et al., 4th ed., U.S. Dept. of Health and Human Sciences, (1937); Dildrop, *Immunology Today*, 5:84, (1984); and Brodeur et al., *Eur. J. Immunol.*, 14; 922, (1984). Classification of the sequenced clones demonstrated that the cDNA library contained $V_H$ sequences of at least 7 different subgroups. Further, a pairwise comparison of the homology between the sequenced clones showed that no two sequences were identical at all positions, suggesting that the population is diverse to the extent that it is possible to characterize by sequence analysis.

Six of the clones (L 36–50 (SEQ ID NOS:27, 24, 34, 20, 35, 37, 31), FIG. 5) belong to the subclass III B and had very similar nucleotide sequences. This may reflect a preponderance of mRNA derived from one or several related variable genes in stimulated spleen, but the data does not permit ruling out the possibility of a bias in the amplification process.

9. $V_H$-Expression Vector Construction

The main criterion used in choosing a vector system was the necessity of generating the largest number of Fab fragments which could be screened directly. Bacteriophage lambda was selected as the expression vector for three reasons. First, in vitro packaging of phage DNA is the most efficient method of reintroducing DNA into host cells. Second, it is possible to detect protein expression at the level of single phage plaques. Finally, the screening of phage libraries typically involve less difficulty with nonspecific binding. The alternative, plasmid cloning vectors, are only advantageous in the analysis of clones after they have been identified. This advantage is not lost in the present system because of the use of lambda zap, thereby permitting a plasmid containing the heavy chain, light chain, or Fab expressing inserts to be excised.

To express the plurality Of $V_H$-coding DiiA homologs in an *E. coli* host cell, a vector was constructed that placed the $V_H$-coding DNA homologs in the proper reading frame, provided a ribosome binding site as described by Shine et al., *Nature*, 254:34, 1975, provided a leader sequence directing the expressed protein to the periplasmic space, provided a polynucleotide sequence that coded for a known epitope (epitope tag) and also provided a polynucleotide that coded for a spacer protein between the $V_H$-coding DNA homolog and the polynucleotide coding for the epitope tag. A synthetic DNA sequence containing all of the above polynucleotides and features was constructed by designing single stranded polynucleotide segments of 20–40 bases that would hybridize to each other and form the double stranded synthetic DNA sequence shown in FIG. 6. The individual single-stranded polynucleotides ($N_1$–$N_{12}$) are shown in Table 3 (SEQ ID NOS:85–96).

Polynucleotides 2, 3, 9–4', 11, 10–5', 6, 7 and 8 were kinased by adding 1 μl of each polynucleotide (0.1 ug/ul) and 20 units of $T_4$ polynucleotide kinase to a solution containing 70 mM Tris-HCl at pH 7.6, 10 mM $MgCl_2$, 5 mM DTT, 10 mM 2ME, 500 micrograms per ml of BSA. The solution was maintained at 37° C. for 30 minutes and the reaction stopped by maintaining the solution at 65° C. for 10 minutes. The two end polynucleotides 20 ng of polynucleotides N1 (SEQ ID NO:85) and polynucleotides N12 (SEQ ID NO:95), were added to the above kinasing reaction solution together with 1/10 volume of a solution containing 20.0 mM Tris-HCl at pH 7.4, 2.0 MM $MgCl_2$ and 50.0 mM NaCl. This solution was heated to 70° C. for 5 minutes and allowed to cool to room temperature, approximately 25° C. over 1.5 hours in a 500 ml beaker of water. During this time period all 10 polynucleotides annealed to form the double stranded synthetic DNA insert shown in FIG. 6A (SEQ ID NO:38). The individual polynucleotides were covalently linked to each other to stabilize the synthetic DNA insert by adding 40 μl of the above reaction to a solution containing 50 mM Tris-HCl at pH 7.5, 7 MM $MgCl_2$, 1 MM DTT, 1 mM adenosine triphosphate (ATP) and 10 unit of T4 DNA ligase. This solution was maintained at 37° C. for 30 minutes and then the T4 DNA ligase was inactivated by maintaining the solution at 65° C. for 10 minutes. The end polynucleotides were kinased by mixing 52 μl of the above reaction, 4 μl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes. The completed synthetic DNA insert was ligated directly into a lambda Zap II vector that had been previously digested with the restriction enzymes Not I and Xho I. The ligation mixture was packaged according to the manufacture's instructions using Gigapack II Gold packing extract available from Stratagene Cloning Systems, La Jolla, Calif. The packaged ligation mixture was plated on XL1 blue cells (Stratagene Cloning Systems, San Diego, Calif.). Individual lambda Zap II plaques were cored and the inserts excised according to the in vivo excision protocol provided by the manufacturer, Stratagene Cloning Systems, La Jolla, Calif. This in vivo excision protocol moves the cloned insert from the lambda Zap II vector into a plasmid vector to allow easy manipulation and sequencing. The accuracy of the above cloning steps was confirmed by sequencing the insert using the Sanger dideoxide method described in by Sanger et al., *Proc. Natl. Acad. Sci USA*, 74:5463–5467, (1977) and using the manufacture's instructions in the AMV Reverse Transcriptase $^{35}$S-ATP sequencing kit from Stratagene Cloning Systems, La Jolla, Calif.

Figure 7:
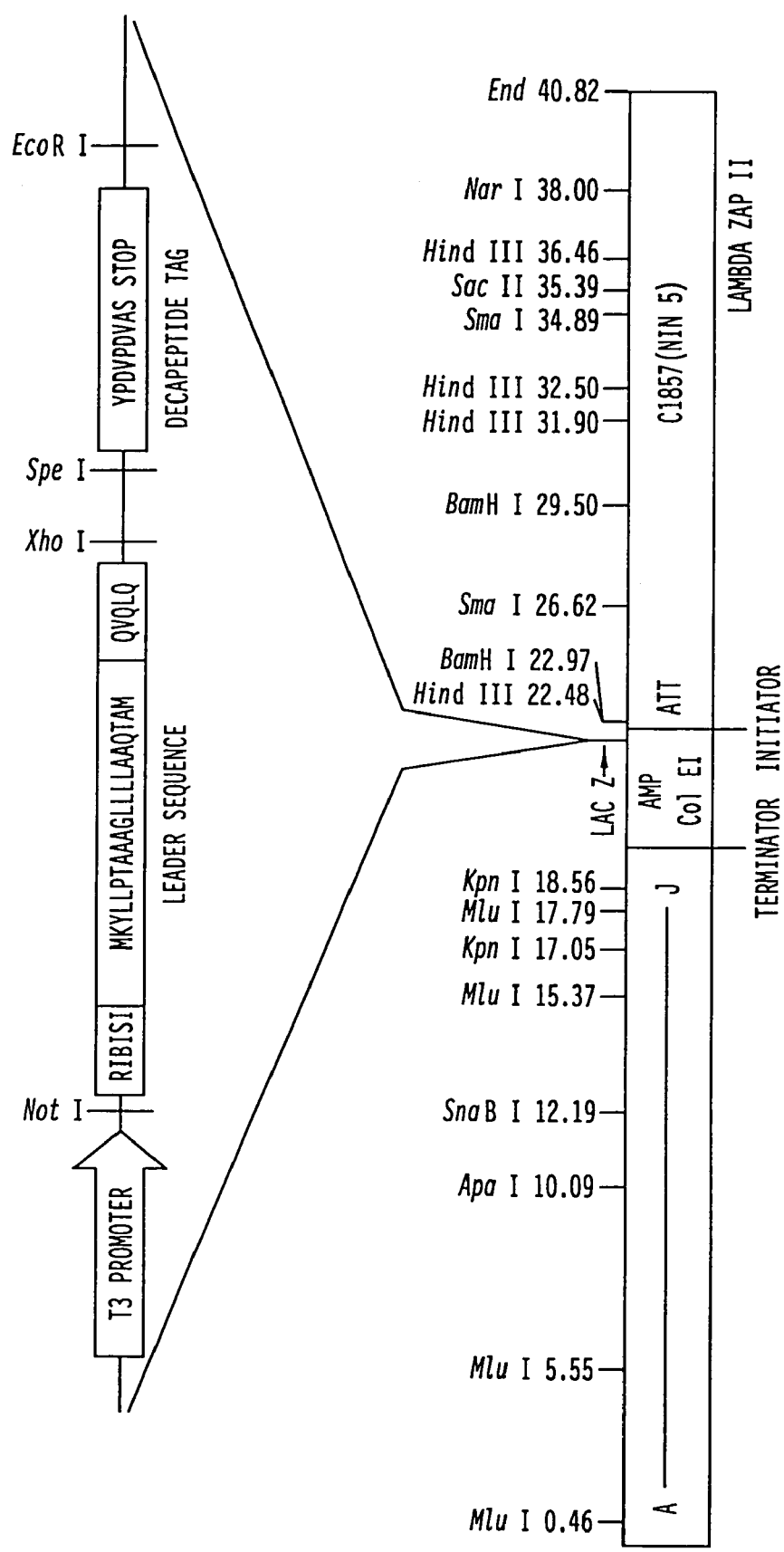
FIG. 7 The major features of the bacterial expression vector Lambda Zap II $V_H$ ($V_H$-expression vector) are shown. The synthetic DNA sequence from FIG. 6 is shown at the top along with the $T_3$ polymerase promoter from Lambda Zap II. The orientation of the insert in Lambda Zap II is shown. The $V_H$-DNA homologs are inserted into the Xho I and Spe I restriction enzyme sites. The $V_H$ DNA are inserted into the Xho I and Spe I site and the read through transcription produces the decapeptide epitope (tag) that is located just 3' of the cloning sites.

The sequence of the resulting $V_H$ expression vector is shown in FIG. 6A (SEQ ID NO:38) and FIG. 7.

TABLE 3

| N1) | 5' GGCCGCAAATTCTATTTCAAGGAGACAGTCAT 3' | (SEQ ID NO:85) |
|---|---|---|
| N2) | 5' AATGAAATACCTATTGCCTACGGCAGCCGCTGGATT 3' | (SEQ ID NO:86) |

TABLE 3-continued

| | | | |
|---|---|---|---|
| N3) | 5' | GTTATTACTCGCTGCCCAACCAGCCATGGCCC 3' | (SEQ ID NO:87) |
| N4) | 5' | AGGTGAAACTGCTCGAGAATTCTAGACTAGGTTAATAG 3' | (SEQ ID NO:88) |
| N5) | 5' | TCGACTATTAACTAGTCTAGAATTCTCGAG 3' | (SEQ ID NO:89) |
| N6) | 5' | CAGTTTCACCTGGGCCATGGCTGGTTGGG 3' | (SEQ ID NO:90) |
| N7) | 5' | CAGCGAGTAATAACAATCCAGCGGCTGCCGTAGGCAATAG 3' | (SEQ ID NO:91) |
| N8) | 5' | GTATTTCATTATGACTGTCTCCTTGAAATAGAATTTGC 3' | (SEQ ID NO:92) |
| N9-4) | 5' | AGGTGAAACTGCTCGAGATTTCTAGACTAGTTACCCGTAC 3 | (SEQ ID NO:93) |
| N11) | 5' | GACGTTCCGGACTACGGTTCTTAATAGAATTCG 3' | (SEQ ID NO:94) |
| N12) | 5' | TCGACGAATTCTATTAAGAACCGTAGTC 3' | (SEQ ID NO:95) |
| N10-5) | 5' | CGGAACGTCGTACGGGTAACTAGTCTAGAAATCTCGAG 3' | (SEQ ID NO:96) |

10. $V_L$ Expression Vector Construction

To express the plurality of $V_L$ coding polynucleotides in an *E. coli* host cell, a vector was constructed that placed the $V_L$ coding polynucleotide in the proper reading frame, provided a ribosome binding site as described by Shine et al., *Nature*, 254:34, (1975), provided a leader sequence directing the expressed protein to the periplasmic space and also provided a polynucleotide that coded for a spacer protein between the $V_L$ polynucleotide and the polynucleotide coding for the epitope tag. A synthetic DNA sequence containing all of the above polynucleotides and features was constructed by designing single stranded polynucleotide segments of 20–40 bases that would hybridize to each other and form the double stranded synthetic DNA sequence shown in FIG. 6B (SEQ ID NO:39). The individual single-stranded polynucleotides ($N_1$–$N_8$) are shown in Table 3 (SEQ ID NOS:85–91).

Polynucleotides N2 (SEQ ID NO:86), N3 (SEQ ID NO:87), N4 (SEQ ID NO:88, N6 (SEQ ID NO:90), N7 (SEQ ID NO:91) and N8 (SEQ ID NO:92) were kinased by adding 1 μl of each polynucleotide and 20 units of $T_4$ polynucleotide kinase to a solution containing 70 mM Tris-HCl at pH 7.6, 10 mM $MgCl_2$, 5 mM DDT, 10 mM 2ME, 500 micrograms per ml of BSA. The solution was maintained at 37° C. for 30 minutes and the reaction stopped by maintaining the solution at 65° C. for 10 minutes. The two end polynucleotides 20 ng of polynucleotides N1 (SEQ ID NO:85) and polynucleotides N5 (SEQ ID NO:89) were added to the above kinasing reaction solution together with 1/10 volume of a solution containing 20.0 mM Tris-HCl at pH 7.4, 2.0 MM $MgCl_2$ and 50.0 mM NaCl. This solution was heated to 70° C. for 5 minutes and allowed to cool to room temperature, approximately 25° C., over 1.5 hours in a 500 ml beaker of water. During this time period all the polynucleotides annealed to form the double stranded synthetic DNA insert. The individual polynucleotides were covalently linked to each other to stabilize the synthetic DNA insert with adding 40 μl of the above reaction to a solution containing 50 ul Tris-HC I at pH 7.5, 7 mM $MgCl_2$, 1 mM DTT, 1 mM ATP and 10 units of T4 DNA ligase. This solution was maintained at 37° C. or 30 minutes and then the T4 DNA ligase was inactivated by maintaining the solution at 65° C. for 10 minutes. The end polynucleotides were kinased by mixing 52 μl of the above reaction, 4 μl of a solution recontaining 10 mM ATP and 5 units of T4 polynucleotide kinase. This solution was maintained at 37° C. for 30 minutes and then the T4 polynucleotide kinase was inactivated by maintaining the solution at 65° C. for 10 minutes. The completed synthetic DNA insert was ligated directly into a lambda Zap II vector that had been previously digested with the restriction enzymes Not I and Xho I. The ligation mixture was packaged according to the manufacture's instructions using Gigapack II Gold packing extract available from Stratagene Cloning Systems, La Jolla, Calif. The packaged ligation mixture was plated on XL1-Blue cells (Stratagene Cloning Systems, La Jolla, Calif.). Individual lambda Zap II plaques were cored and the inserts excised according to the in vivo excision protocol provided by the manufacturer, Stratagene Cloning Systems, La Jolla, Calif. and described in Short et al., *Nucleic Acids Res.*, 16:7583–7600, 1988. This in vivo excision protocol moves the cloned insert from the lambda Zap II vector into a phagemid vector to allow easy manipulation and sequencing and also produces the phagemid version of the $V_L$ expression vectors. The accuracy of the above cloning steps was confirmed by sequencing the insert using the Sanger dideoxide method described by Sanger et al., *Proc. Natl. Acad. Aci. USA*, 74:5463–5467, (1977) and using the manufacturer's instructions in the AMV reverse transcriptase $^{35}$S-dATP sequencing kit from Stratagene Cloning Systems, La Jolla, Calif. The sequence of the resulting $V_L$ expression vector is shown in FIG. 6 and FIG. 8.

The $V_L$ expression vector used to construct the library was the phagemid produced to allow the DNA of the, $V_L$ expression vector to be determined. The phagemid was produced, as detailed above, by the in vivo excision process from the Lambda Zap $V_L$ expression vector (FIG. 8). The phagemid version of this vector was used because the Nco I restriction enzyme site is unique in this version and thus could be used to operatively linked the $V_L$ DNA homologs into the expression vector.

11. $V_L$II-Expression Vector Construction

Figure 9:
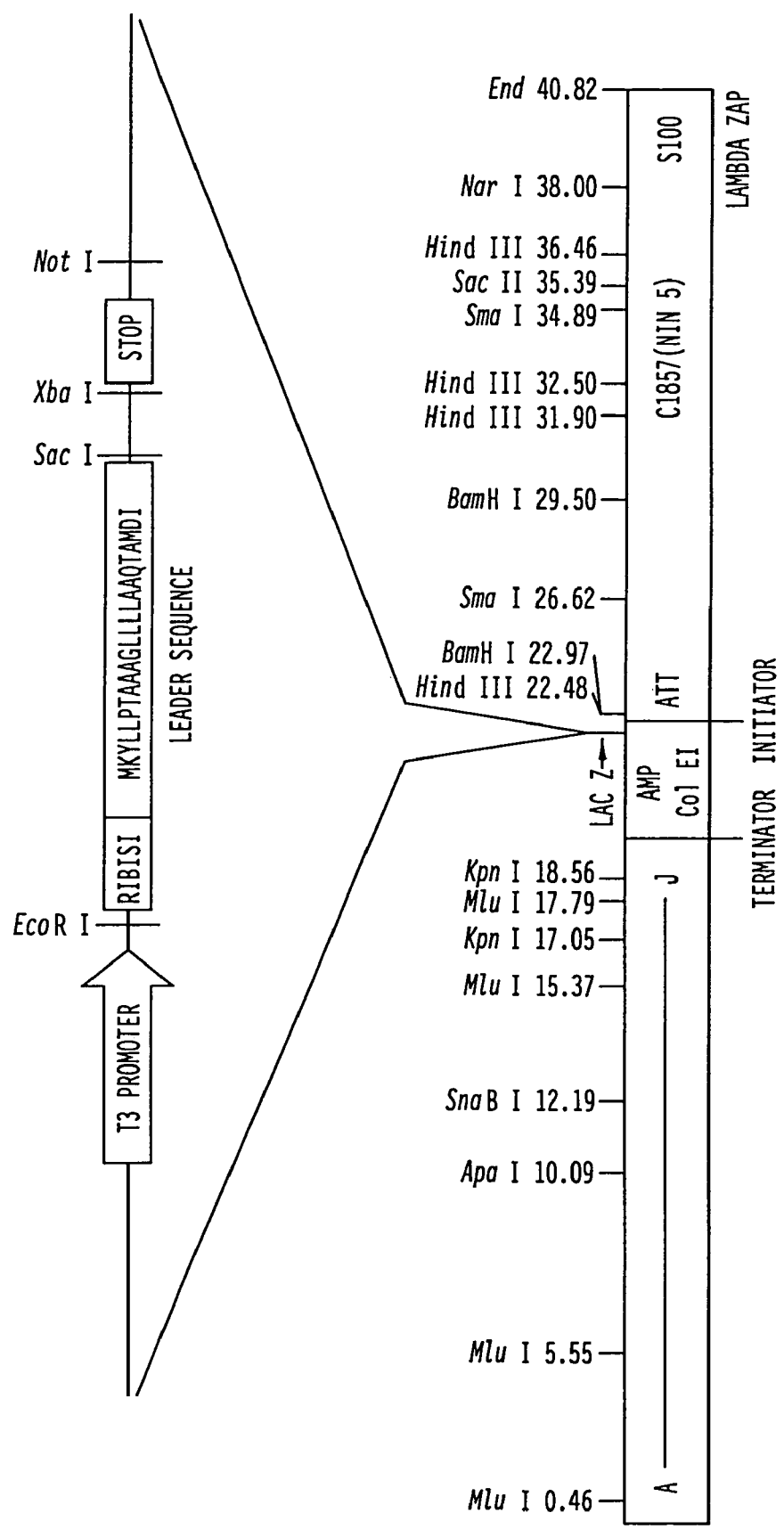
FIG. 9A modified bacterial expression vector Lambda Zap II $V_L$II. This vector is constructed by inserting this synthetic DNA sequence, (SEQ ID NO:40)
TGAATTCTAAACTAGTCGCCAAGGAGACAGTCATAATGAATCGAACTTAA

To express the plurality of $V_L$-coding DNA homologs in an *E. coli* host cell, a vector was constructed that placed the $V_L$-coding DNA homologs in the proper reading frame, provided a ribosome binding site as described by Shine et al., *Nature*, 254:34, 1975, provided the Pel B gene leader sequence that has been previously used to successfully secrete Fab fragments in *E. coli* by Lei et al., *J. Bac.*, 169:4379 (1987) and Better et al., *Science*, 240:1041 (1988), and also provided a polynucleotide containing a restriction endonuclease site for cloning. A synthetic DNA sequence containing all of the above polynucleotides-and features was constructed by designing single stranded polynucleotide segments of 20–60 bases that would hybridize to each other and form the double stranded synthetic DNA sequence shown in FIG. 10 (SEQ ID NO:41). The sequence of each individual single-stranded polynucleotides (01–08) within the double stranded synthetic DNA sequence is shown in Table 4 (SEQ ID NOS:86; 87; 97; 98; 99; 100; 101; 102).

lambda Zap II plaques were cored and the inserts excised according to the in vivo excision protocol provided by the manufacturer, Stratagene Cloning Systems, La Jolla, Calif. This in vivo excision protocol moves the cloned insert from the lambda Zap II vector into a plasmid vector to allow easy manipulation and sequencing. The accuracy of the above cloning steps was confirmed by sequencing the insert using the manufacture's instructions in the AMV Reverse Transcriptase $^{35}$S-dATP sequencing kit from Stratagene Cloning Systems, La Jolla, Calif. The sequence of the resulting $V_L$II-expression vector is shown in FIG. 9 and FIG. 11.

TABLE 4

| | |
|---|---|
| 01) 5' TGAATTCTAAACTAGTCGCCAAGGAGACAGTCAT 3' | (SEQ ID NO:97) |
| 02) 5' AATGAAATACCTATTGCCTACGGCAGCCGCTGGATT 3' | (SEQ ID NO:86) |
| 03) 5' GTTATTACTCGCTGCCCAACCAGCCATGGCC 3' | (SEQ ID NO:87) |
| 04) 5' GAGCTCGTCAGTTCTAGAGTTAAGCGGCCG 3' | (SEQ ID NO:98) |
| 05) 5' GTATTTCATTATGACTGTCTCCTTGGCGACTAGTTTAGAATTCAAGCT 3' | (SEQ ID NO:99) |
| 06) 5' CAGCGAGTAATAACAATCCAGCGGCTGCCGTAGGCAATAG 3' | (SEQ ID NO:100) |
| 07) 5' TGACGAGCTCGGCCATGGCTGGTTGGG 3' | (SEQ ID NO:101) |
| 08) 5' TCGACGGCCGCTTAACTCTAGAAC 3' | (SEQ ID NO:102) |

Polynucleotides 02, 03, 04, 05, 06 and 07 were kinased by adding 1 μl (0.1 ug/μl) of each polynucleotide and 20 units of T$_4$ polynucleotide kinase to a solution containing 70 mM Tris-HCl at pH 7.6, 10 mM magnesium chloride (MgCl), 5 mM dithiothreitol (DTT), 10 mM 2-mercaptoethanol (2ME), 500 micrograms per ml of bovine serum albumin. The solution was maintained at 37 C for 30 minutes and the reaction stopped by maintaining the solution at 65 C for 10 minutes. The 20 ng each of the two end polynucleotides, 01 and 08, were added to the above kinasing reaction solution together with 1/10 volume of a solution containing 20.0 mM Tris-HCl at pH 7.4, 2.0 mM MgCl and 15.0 mM sodium chloride (NaCl). This solution was heated to 70 C for 5 minutes and allowed to cool to room temperature, approximately 25 C, over 1.5 hours in a 500 ml beaker of water. During this time period all 8 polynucleotides annealed to form the double stranded synthetic DNA insert shown in FIG. 9. The individual polynucleotides were covalently linked to each other to stabilize the synthetic DNA insert by adding 40 μl of the above reaction to a solution containing 50 ml. Tris-HCl at pH 7.5, 7 ml MgCl, 1 mm DTT, 1 mm ATP and 10 units of T4 DNA ligase. This solution was maintained at 37 C for 30 minutes and then the T4 DNA ligase was inactivated by maintaining the solution at 65 C for 10 minutes. The end polynucleotides were kinased by mixing 52 μl of the above reaction, 4 μl of a solution containing 10 mM ATP and 5 units of T4 polynucleotide kinase. This solution was maintained at 37 C for 30 minutes and then the T4 polynucleotide kinase was inactivated by maintaining the solution at 65 C for 10 minutes. The completed synthetic DNA insert was ligated directly into a lambda Zap II vector that had been previously digested with the restriction enzymes Not I and Xho I. The ligation mixture was packaged according to the manufacture's instructions using Gigapack II Gold packing extract available from Stratagene Cloning Systems, La Jolla, Calif. The packaged ligation mixture was plated on XL1 blue cells (Stratagene Cloning Systems, San Diego, Calif.). Individual 12. $V_H + V_L$ Library Construction To prepare an expression library enriched in $V_H$ sequences, DNA homologs enriched in $V_H$ sequences were prepared according to Example 6 using the same set of 5' primers but with primer 12A (Table 1 (SEQ ID NO:54)) as the 3' primer. These homologs were then digested with the restriction enzymes Xho I and Spe I and purified on a 1% agarose gel using the standard electroelution technique described in *Molecular Cloning A Laboratory Manual*, Maniatis et al., eds., Cold Spring Harbor, N.Y., (1982). These prepared $V_H$ DNA homologs were then directly inserted into the $V_H$ expression vector that had been previously digested with Xho I and Spe I.

The ligation mixture containing the $V_H$ DNA homologs were packaged according to the manufacturers specifications using Gigapack Gold II Packing Extract (Stratagene Cloning Systems, La Jolla, Calif.). The expression libraries were then ready to be plated on XL-1 Blue cells.

To prepare a library enriched in $V_L$ sequences, PCR amplified products enriched in $V_L$ sequences were prepared according to Example 6. These $V_L$ DNA homologs were digested with restriction enzymes Nco I and Spe I. The digested $V_L$ DNA homologs were purified on a to agarose gel using standard electroelusion techniques described in *Molecular Cloning A Laboratory Manual*, Maniatis et al., eds., Cold Spring Harbor, N.Y. (1982). The prepared $V_L$ DNA homologs were directly inserted into the $V_L$ expression vector that had been previously digested with the restriction enzymes Nco I and Spe I. The ligation mixture containing the $V_L$ DNA homologs were transformed into XL-1 blue competent cells using the manufacturer's instructions (Stratagene Cloning Systems, La Jolla, Calif.).

13. Inserting $V_L$ Coding DNA Homologs into $V_L$ Expression Vector

In preparation for cloning a library enriched in sequences, PCR amplified products (2.5 ug/30 ul of 150 mM $V_L$ NaCl, 8 mM Tris-HCl (pH 7.5), 6 mM MgSO$_4$, 1 mM DTT, 200 ug/ml BSA at 37 C were digested with restriction enzymes sac 1 (125 units) and Xba 1 (125 units) and purified on a 1% agarose gel. In cloning experiments which required a mixture of the products of the amplification reactions equal volumes (50 ul, 1–10 ug concentration) of each reaction mixture were combined after amplification but before restriction digestion. After gel electrophoresis of the digested PCR amplified spleen mRNA, the region of the gel containing DNA fragments of approximate 350 bps was excised, electroeluted into a dialysis membrane, ethanol precipitated and resuspended in a TE solution containing 10 mM Tris-HCl pH 7.5 and 1 mM EDTA to a final concentration 50 ng/ul.

The $V_L$II-expression DNA vector was prepared for cloning by admixing 100 ug of this DNA to a solution containing 250 units each of the restriction endonucleases. Sac I and Xba I (both from Boehringer Mannheim, Indianapolis, Ind.) and a buffer recommended by the manufacturer. This solution was maintained at 37 from 1.5 hours. The solution was heated at 65 C for 15 minutes top of inactivate the restriction endonucleases. The solution was chilled to 30 C and 25 units of heat-killable (HK) phosphatase (Epicenter, Madison, Wis.) and $CaCl_2$ were admixed to it according to the manufacturer's specifications. This solution was maintained at 30 C for 1 hour. The DNA was purified by extracting the solution with a mixture of phenol and chloroform followed by ethanol precipitation. The $V_L$II expression vector was now ready for ligation to the $V_L$ DNA homologs prepared in the above examples.

DNA homologs enriched in $V_L$ sequences were prepared according to Example 5 but using a 5' light chain primer and the 3' light chain primer shown in Table 2. Individual amplification reactions were carried out using each 5' light chain primer in combination with the 3' light chain primer. These separate $V_L$ homolog containing reaction mixtures were mixed and digested with the restriction endonucleases Sac 1 and Xba 1 according to Example 6. The $V_L$ homologs were purified on a 1% agarose gel using the standard electroelution technique described in *Molecular Cloning A Laboratory Manual*, Maniatis et al., eds., Cold Spring Harbor, N.Y., (1982). These prepared $V_L$ DNA homologs were then directly inserted into the Sac 1-Xba cleaved $V_L$II-expression vector that was prepared above by ligating 3 moles of $V_L$ DNA homolog inserts with each mole of the $V_L$II-expression vector overnight at 5 C. $3.0×10^5$ plague forming units were obtained after packaging the DNA with Gigapack II Bold (Stratagene Cloning Systems, La Jolla, Calif.) and 50% were recombinants.

14. Randomly Combining $V_H$ and $V_L$ DNA Homologs on the Same Expression Vector The $V_L$II-expression library prepared in Example 13 was amplified and 500 ug of $V_L$II-expression library phage DNA prepared from the amplified phage stock using the procedures described in *Molecular Cloning: A Laboratory Manual*, Maniatis et al., eds., Cold Spring Harbor Laboratory, Cold Spring Harbor, N.Y. (1982), 50 ug of this $V_L$II-expression library phage DNA was maintained in a solution containing 100 units of MLuI restriction endonuclease (Boehringer Mannheim, Indianapolis, Ind.) in 200 ul of a buffer supplied by the endonuclease manufacturer for 1.5 hours at 37 C. The solution was then extracted with a mixture of phenol and chloroform. The DNA was then ethanol precipitated and resuspended in 100 ul of water. This solution was admixed with 100 units of the restriction endonuclease EcoR I (Boehringer Mannheim, Indianapolis, Ind.) in a final volume of 200 ul of buffer containing the components specified by the manufacturer. This solution was maintained at 37 C for 1.5 hours and the solution was then extracted with a mixture of phenol and chloroform. The DNA was ethanol precipitated and the DNA resuspended in TE.

The $V_H$ expression library prepared in Example 12 was amplified and 500 ug of $V_H$ expression library page DNA prepared using the methods detailed above. 50 ug of the $V_H$ expression library phage DNA was maintained in a solution containing 100 units of Hind III restriction endonuclease (Boehringer Mannheim, Indianapolis, Ind.) in 200 ul of a buffer supplied by the endonuclease manufacturer for 1.5 hours at 37 C. The solution was then extracted with a mixture of phenol and chloroform saturated with 0.1 M Tris-HCl at pH 7.5. The DNA was then ethanol precipitated and resuspended in 100 ul of water. This solution was admixed with 100 units of the restriction endonuclease EcoR I (Boehringer Mannheim, Indianapolis, Ind.) in a final volume of 200 ul of buffer containing the components specified by the manufacturer. This solution was maintained at 37 C for 1.5 hours and the solution was then extracted with a mixture of phenol and chloroform. The DNA was ethanol precipitated and the DNA resuspended in TE.

The restriction digested $V_H$ and $V_L$II-expression Libraries were ligated together. The ligation reaction consisted of 1 ug of $V_H$ and 1 ug of $V_L$II phage library DNA in a 10 ul reaction using the reagents supplied in a ligation kit purchased from Stratagene Cloning Systems (La Jolla, Calif.). After ligation for 16 hr at 4 C, 1 ul of the ligated the phage DNA was packaged with Gigapack Gold II packaging extract and plated on XL 1-blue cells prepared according to the manufacturers instructions. A portion of the $3×10^6$ clones obtained were used to determine the effectiveness of the combination. The resulting $V_H$ and $V_L$ expression vector is shown in FIG. 11.

Clones containing both $V_H$ and $V_L$ were excised from the phage to pBluescript using the in vitro excision protocol described by Short et al., *Nucleic Acid Research*, 16:7583–7600 (1988). Clones chosen for excision expressed the decapeptide tag and did not cleave X-gal in the presence of 2 mM IPTG thus remaining white. Clones with these characteristics represented 30% of the library. 50% of the clones chosen for excision contained a $V_H$ and $V_L$ as determined by restriction analysis. Since approximately 30% of the clones in the $V_H$ library expressed the decapeptide tag and 50% of the clones in the $V_L$II library contained a $V_L$ sequence it was anticipated that no more than 150 of the clones in the combined library would contain both $V_H$ and clones. The actual number obtained was 15% of the library indicating that the process of combination was very efficient.

15. Segregating DNA Homologs For a $V_H$ Antigen Binding Protein

To segregate the individual clones containing DNA that code for a $V_H$ antigen binding protein, the titre $V_H$ expression library prepared according to Example 11 was determined. This library titration was performed using methods well known to one skilled in the art. Briefly, serial dilutions of the library were made into'a buffer containing 100 mM NaCl, 50 mM Tris-HCl at pH 7.5 and 10 MM $MgSO_4$. Ten ul of each dilution was added to 200 ul of exponentially growing *E. coli* cells and maintained at 37 C for 15 minutes to allow the phage to absorb to the bacterial cells. Three ml of top agar consisting of 5 g/L NaCl, 2 g/L of $MgSO_4$, 5 g/L yeast extract, 10 g/L NZ amine (casein hydrolysate) and 0.7% melted, 50 C agarose. The phage, the bacteria and the top agar were mixed and then evenly distributed across the surface of a prewarmed bacterial agar plate (5 g/L NaCl, 2 g/L $MgSO_4$, 5 g/L yeast extract, 10 g/L NZ amine (casein hydrolysate) and 15 g/L Difco agar. The plates were maintained at 37 C for 12 to 24 hours during which time period the lambda plaques developed on the bacterial lawn. The lambda plaques were counted to determined the total number of plaque forming units per ml in the original library.

The titred expression library was then plated out so that replica filters could be made from the library. The replica filters will be used to later segregate out the individual clones in the library that are expressing the antigens binding proteins of interest. Briefly, a volume of the titred library that would yield 20,000 plaques per 150 millimeter plate was added to 600 ul of exponentially growing E. coli cells and maintained at 37 C for 15 minutes to allow the phage to absorb to the bacterial cells. Then 7.5 ml of top agar was admixed to the solution containing the bacterial cells and the absorbed phage and the entire mixture distributed evenly across the surface of a prewarmed bacterial agar plate. This process was repeated for a sufficient number of plates to plate out a total number of plaques at least equal to the library size. These plates were then maintained at 37° C. for 5 hours. The plates were then overlaid with nitrocellulose filters that had been pretreated with a solution containing 10 mM isopropyl-beta-D-thiogalactopyranosid (IPTG) and maintained at 37 C for 4 hours. The orientation of the nitrocellulose filters in relation to the plate were marked by punching a hole with a needle dipped in waterproof ink through the filter and into the bacterial plates at several locations. The nitrocellulose filters were removed with forceps and washed once in a TBST solution containing 20 mM Tris-HCL at pH 7.5, 150 mM NaCl and 0.05% monolaurate (tween-20). A second nitrocellulose filter that had also been soaked in a solution containing 10 mM IPTG was reapplied to the bacterial plates to produce duplicate filters. The filters were further washed in a fresh solution of TBST for 15 minutes. Filters were then placed in a blocking solution consisting of 20 mM Tris-HCl at pH 7.5, 150 mM NaCL and to BSA and agitated for 1 hour at room temperature. The nitrocellulose filters were transferred to a fresh blocking solution containing a 1 to 500 dilution of the primary antibody and gently agitated for at least 1 hour at room temperature. After the filters were agitated in the solution containing the primary antibody the filters were washed 3 to 5 times in TBST for 5 minutes each time to remove any of the residual unbound primary antibody. The filters were transferred into a solution containing fresh blocking solution and a 1 to 500 to a 1 to 1,000 dilution of alkaline phosphatase conjugated secondary antibody. The filters were gently agitated in the solution for at least 1 hour at room temperature. The filters were washed 3 to 5 times in a solution of TBST for at least 5 minutes each time to remove any residual unbound secondary antibody. The filters were washed once in a solution containing 20 mM Tris-HCl at pH 7.5 and 150 mM NaCL. The filters were removed from this solution and the excess moisture blotted from them with filter paper. The color was developed by placing the filter in a solution containing 100 M Tris-HCl at pH 9.5, 100 mM NaCl, 5 mM $MgCl_2$, 0.3 mg/ml of nitro Blue Tetrazolium (NBT) and 0.15 mg/ml of 5-bromo-4-chloro-3-indolyl-phosphate (BLIP) for at least 30 minutes at room temperature. The residual color development solution was rinsed from the filter with a solution containing 20 mM Tris-HCl at pH 7.5 and 150 mM NaCl. The filter was then placed in a stop solution consisting of 20 mM Tris-HCl at pH 2.9 and 1 mM EDTA. The development of an intense purple color indicates at positive result. The filters are used to locate the phage plaque that produced the desired protein. That phage plaque is segregated and then grown up for further analysis.

Several different combinations of primary antibodies and second antibodies were used. The first combination used a primary antibody immunospecific for a decapeptide that will be expressed only if the $V_H$ antigen binding protein is expressed in the proper reading frame to allow read through translation to include the decapeptide epitope covalently attached to the $V_H$ antigen binding protein. This decapeptide epitope and an antibody immunospecific for this decapeptide epitope was described by Green et al., *Cell* 28:477 (1982) and Niman et al., *Proc. Nat. Acad. Sci. U.S.A.* 80:4949 (1983). The sequence of the decapeptide recognized is shown in FIG. 11. A functional equivalent of the monoclonal antibody that is immunospecific for the decapeptide can be prepared according to the methods of Green et al. and Niman et al. The secondary antibody used with this primary antibody was a goat antimouse IgG (Fisher Scientific). This antibody was immunospecific for the constant region of mouse IgG and did not recognize any portion of the variable region of heavy chain. This particular combination of primary and secondary antibodies when used according to the above protocol determined that between 25% and 300 of the clones were expressing the decapeptide and therefore these clones were assumed to also be expressing a $V_H$ antigen binding protein.

In another combination the anti-decapeptide mouse monoclonal was used as the primary antibody and an affinity purified goat anti-mouse Ig, commercially available as part of the picoBlue immunoscreening kit from Stratagene Cloning System, La Jolla, Calif., was use as the secondary antibody. This combination resulted in a large number of false positive clones because the secondary antibody also immunoreacted with the $V_H$ of the heavy chain. Therefore this antibody reacted with all clones expressing any $V_H$ protein and this combination of primary and secondary antibodies did not specifically detect clones with the $V_H$ polynucleotide in the proper reading frame and thus allowing expressing of the decapeptide.

Several combinations of primary and secondary antibodies are used where the primary antibody is conjugated to fluorescein isothiocyanate (FITC) and thus the immunospecificity of the antibody was not important because the antibody is conjugated to the preselected antigen (FITC) and it is that antigen that should be bound by the $V_H$ antigen binding proteins produced by the clones in the expression library. After this primary antibody has bound by virtue that is FITC conjugated mouse monoclonal antibody p2 5764 (ATCC #HB-9505). The secondary antibody used with this primary antibody is a goat anti-mouse Ig[6] (Fisher Scientific, Pittsburg, Pa.) conjugated to alkaline phosphatase. Using the method described in *Antibodies A Laboratory Manual*, Harlow and Lowe, eds., Cold Springing Harbor, N.Y., (1983). If a particular clone in the $V_H$ expression, library, expresses a $V_H$ binding protein that binds the FITC covalently coupled to the primary antibody, the secondary antibody binds specifically and when developed the alkaline phosphate causes a distinct purple color to form.

The second combination of antibodies of the type uses a primary antibody that is FITC conjugated rabbit anti-human IgG (Fisher Scientific, Pittsburg, Pa.). The secondary antibody used with this primary antibody is a goat anti-rabbit IgG conjugated to alkaline phosphatase using the methods described in *Antibodies A Laboratory Manual*, Harlow and Lane, eds., Cold Spring Harbor, N.Y., (1988). If a particular clone in the $V_H$ expression library expresses a $V_H$ binding protein that binds the FITC conjugated to the primary antibody, the secondary antibody binds specifically and when developed the alkaline phosphatase causes a distinct purple color to form.

Another primary antibody was the mouse monoclonal antibody p2 5764 (ATCC tt HB-9505) conjugated to both FITC and 125 I. The antibody would be bound by any $V_H$ antigen binding proteins expressed. Then because the antibody is also labeled with $^{125}$I, an autoradiogram of the filter is made instead of using a secondary antibody that is conjugated to alkaline phosphatase. This direct production of an autoradiogram allows segregation of the clones in the library expressing a $V_H$ antigen binding protein of interest.

16. Segregating DNA Homologs For a $V_H$ and $V_L$ that Form an Antigen Binding $F_v$ To segregate the individual clones containing DNA homologs that code for a $V_H$ and a $V_L$ that form an antigen binding $F_v$, the $V_H$ and $V_L$ expression library was titred according to Example 15. The titred expression library was then screened for the presence of the decapeptide tag expressed with the $V_H$ using the methods described in Example 15. DNA was then prepared from the clones to express the decapeptide tag. This DNA was digested with the restriction endonuclease PvuII to determine whether these clones also contained a $V_L$ DNA homolog. The slower migration of a PvuII restriction endonuclease fragment indicated that the particular clone contained both a $V_H$ and a $V_L$ DNA homolog.

The clones containing both a $V_H$ and a $V_L$ DNA homolog were analyzed to determine whether these clones produced an assembled $F_v$ protein molecule from the $V_H$ and $V_L$ DNA homologs.

The $F_v$ protein fragment produced in clones containing both $V_H$ and $V_L$ was visualized by immune precipitation of radiolabeled protein expressed in the clones. A 50 ml culture of LB broth (5 g/L yeast extract, 10 g/L and tryptone 10 g/L NaCl at pH 7.0) containing 100 ug/ul of ampicillin was inoculated with E. Coli harboring a plasmid contain a $V_H$ and a $V_L$. The culture was maintained at 37 C with shaking until the optical density measured at 550 nm was 0.5 culture then was centrifuged at 3,000 g for 10 minutes and resuspended in 50 ml of M9 media (6 g/L $Na_2HPO_4$, 3 g/L $KH_2PO_4$, 0.5 g/L NaCl, 1 g/L $NH_4Cl$, 2 g/L glucose, 2 MM $MgSO_4$ and 0.1 M$MgSO_4$ $CaCl_2$ supplemented with amino acids without methionine or cysteine. This solution was maintained at 37 C for 5 minutes and then 0.5 mCi of $^{35}$S as $HSO_4$ (New England Nuclear, Boston, Mass.) was added and the solution was further maintained at 37 C for an additional 2 hours. The solution was then centrifuged at 3000×g and the supernatant discarded. The resulting bacterial cell pellet was frozen and thawed and then resuspended in a solution containing 40 mM Tris pH 8.0, 100 mM sucrose and 1 mM EDTA. The solution was centrifuged at 10000×g for 10 minutes and the resulting pellet discarded. The supernatant was admixed with 10 ul of anti-decapeptide monoclonal antibody and maintained for 30–90 minutes on ice. 40 ul of protein G coupled to sepharose beads (Pharmacia, Piscataway, N.J.) was admixed to the solution and the added solution maintained for 30 minutes on ice to allow an immune precipitate to form. The solution was centrifuged at 10,000×g for 10 minutes and the resulting pellet was resuspended in 1 ml of a solution containing 100 mM Tris-HCl at pH 7.5 and centrifuged at 10,000×g for 10 minutes. This procedure repeated twice. The resulting immune precipitate pellet loaded onto a PhastGel Homogenous 20 gel (Pharmacia, Piscataway, N.J.) according to the manufacturer's directions. The gel was dried and used to expose X-ray film.

The resulting autoradiogram is shown in FIG. 12. The presence of assembled $F_v$ molecules can be seen by the presence of $V_L$ that was immunoprecipitated because it was attached to the $V_H$-decapeptide tag recognized by the precipitating antibody.

17. Construction of Selectable $V_H$ and $V_L$ Expression

A. Construction of the Mutant S Gene Expression Plasmid

The bacteria phage lambda S gene has been shown to be directly involved in lysis as described by Reader et al., Virology, 43:607–622 (1971). The S gene encodes a 107 amino acid polypeptide that is responsible for a lethal event in the cytoplasmic membrane that allows the release of the R gene product into the periplasm of the cell where it degrades the peptidoglycan as described by Garrett et al., J. Virology, 44:886–892 (1982). The dominant S gene mutant ($S_{100}$ SAM 5) is a mutation that has been shown to interfere with the formation of the normal S protein membrane channel thus preventing cell lysis. See Raab et al., J. Mol. Biol., 199:95–105 (1988). This mutant S gene is dominant because when it is expressed, even in the presence of the wild type S protein it prevents lysis of the bacterial cell. The $S_{100}$ SAM 5 dominant mutation also contains an amber mutation and therefore requires the expression of a suppressor tRNA in the bacterial cell in order for mutant S protein to be produced. Further, this amber mutation allows the growth of bacteria containing the mutant S gene construct without lysis because without this amber suppressing tRNA no functional S gene protein is produced.

The dominant S gene from Lambda Zap Sam 5 was isolated using the polymerase chain reaction. Briefly, Lambda Zap Sam 5 DNA was isolated using the methods described in Molecular Cloning: A Laboratory Manual, Maniatis et al., eds., Cold Spring Harbor, N.Y. (1962). Lambda Zap Sam 5 DNA, 0.1 ug, was admixed with a buffer containing 150 ng of primer RG15 (Table 5 (SEQ ID NO:103)) and 150 ng of primer RG16 (Table 5 (SEQ ID NO:104)), 0.25 mM each of dTTP, dCTP, dGTP, and DATP (dNTPs), 50 mM KCl, 10 mM Tris-HCl at pH 8.3, 1.5 mM MgCl2, and 0.15% sterile gelatin. The resulting solution was heated to 91° C. for five minutes and then placed in a 54 C water bath for five minutes. 0.5 microliters of Taq polymerase (Perkin Elmer-Cetus, Norwalk, Conn.) was added and the solution overlaid with a layer of mineral oil.

The solution was then placed in a DNA Thermal Cycler (Perkin-Elmer Cetus, Norwalk, Conn.) and subjected to the following temperature and time conditions: (1) 72 C for two minutes to allow for primer extension, (2) 91° C. for one minute to heat denature the duplex DNA and (3) 54 C for two minutes to allow the single-stranded nucleic acids to hybridize. The same solution was subjected to further cycles of steps (1), (2), and (3) for a total of thirty cycles according to the manufacturer's instructions. The cycled solution was then maintained at 72 C for ten minutes and then stored at 4 C until used.

The mutant S gene DNA produced by the above polymerase chain reaction was digested with the restriction endonucleases Hind III and Bgl II. Briefly, one half of the polymerase chain reaction product produced above was purified by phenol extraction followed by ethanol precipitation. The DNA was then admixed with a solution containing 100 mM NaCl, 10 mM Tris-HCl atpH7.7, 19 mM $MgCl_2$, 1 mMDTT, 100 ug/ml BSA, 20 units of Hind III and 10 units of Bgl II. This solution was maintained at 37 C for one hour. The efficiency of this restriction endonuclease digestion was determined by gel electrophoresis according to the methods described in Current Protocols in Molecular Biology, Ausubel et al., eds., John Wiley and Sons, New York (1987).

One half of the polymerase chain reaction product was digested with the restriction endonucleases Sau 3A and Bgl II. Briefly, the DNA was admixed with a buffer containing 100 mM NaCl, 10 mM Tris-HCl at pH 7.7, 10 mM MgCl$_2$, 1 mM DTT, 100 ug/ml bovine serum albumin (BSA), 10 units of Sau 3A, and 10 units of Bgl II (Stratagene, La Jolla, Calif.). This solution was maintained at 37 C for one hour. The efficiency of this restriction endonuclease digestion was determined by gel electrophoresis.

The resulting predominant, approximately 500 base pair bands were isolated and purified on agarose gels according to the procedures described in *Molecular Cloning: A Laboratory Manual*, Maniatis et al., eds., Cold Spring Harbor, N.Y. (1982). The DNA was purified from the agarose slices by electroelution according to the methods described in *Molecular Cloning: A Laboratory Manual*, Maniatis et al., eds., Cold Spring Harbor, N.Y. (1982). The electroeluted DNA was purified by phenol extraction followed by ethanol precipitation.

The mutant S gene was inserted into pBluescript KS+ (Stratagene) that had been previously digested with the restriction endonuclease Hind III and BamH I. Briefly, the pBluescript KS+ was admixed with a buffer containing 100 mM Nacl, 10 mM Tris-HCl at pH 7.7, 10 mM MgCl$_2$, 1 nJ4 DTT, 100 ug/ml BSA, 40 units of BamH I and 40 units of Hind III (Stratagene). This solution was maintained at 37 C for one hour. The pBluescript KS+ containing solution was then adjusted to pH 8.0 by adding Tris-HCl at pH 8.0 to a final concentration of 0.1 M. Five units of calf intestinal alkaline phosphatase (Stratagene) was added to this solution and the solution maintained at 37 C for 30 minutes. The calf intestine alkaline phosphatase was then inactivated by maintaining the solution at 65 C for 10 minutes. The pBluescript KS+ was then purified by phenol extraction followed by ethanol precipitation. The restriction endonuclease cleaned pBluescript KS+ was then resuspended in a solution containing 10 mM Tris-HCl at pH 8.0 and 1 mM EDTA.

The mutant S gene was inserted (ligated) into the pBluescript vector prepared above by digestion with Hind III and BamH I restriction endonuclease. Briefly, 1 ul of pBluescript vector that had been previously cut with Hind III and BamH I was admixed with 1 ul of the mutant S gene insert prepared above 1 ul of a buffer containing 0.66 M Tris-HCl at pH 7.6, 50 MM MgCl$_2$, 50 mM Dithiothreitol (DTT) and 1 ul of a solution containing 10 mM ATP and 0.5 ul (4 units) of T4 DNA ligase (Stratagene). This solution was maintained at 37 C for one hour.

The ligation mixture was transformed in XL1 Blue cells (Stratagene) according to the manufacture's directions.

The accuracy of the above cloning steps is confirmed by DNA sequencing.

B. Selectable $V_H$-Expression Vector Construction

To add the ability to select against expression vectors not containing $V_H$-coding DNA homologs, a suppressor tRNA gene was inserted into the V,-Expression vector prepared in Example 9. The selectable $V_H$-Expression vector was prepared by inserting a synthetic DNA sequence containing the suppresser tRNA gene and DNA sequence coding for the decapeptide tag into the $V_H$-Expression vector prepared in Example 9 that had been previously cleaved with the restriction endonucleases Xho I and Eco RI.

A synthetic DNA sequence containing the suppressor tRNA gene and polynucleotide sequence coding for decapeptide tag was constructed by designing single stranded polynucleotide segments of 20–40 bases that would hybridize to each other and form the double stranded synthetic DNA sequence shown in FIG. 18A (SEQ ID NO:119). The individual single-stranded polynucleotides are shown in Table 5 (SEQ ID NO:118).

TABLE 5

| | | |
|---|---|---|
| R615) | 5'-AATAAGCTTGATCTATCAGTAATCGACC-3' | (SEQ ID NO:103) |
| R616) | 5'-ATTAGATCTGAATTCTGACGTCCGTTATCAG-3' | (SEQ ID NO:104) |
| 926) | 5'-GATCCGCTTCCCGATAAGGGAGCAGGCCAGTAAAAGCATTACCTGTGGTGGGGTTC-3' | (SEQ ID NO:105) |
| 927) | 5'-CCGAGCGGCCAAAGGGAGCAGACTCTAAATCTGCCGTCATCGACTTCGAAG-3' | (SEQ ID NO:106) |
| 928) | 5'-GTTCGAATCCTTCCCCCACCACCATCACTTTCAAAAGTCCGA-3' | (SEQ ID NO:107) |
| 929) | 5'-CTAGTCGGACTTTTGAAAGTGATGGTGGTGGGGGAAGGATTCGAACCTTCGAAGTC-3' | (SEQ ID NO:108) |
| 930) | 5'-GATGACGGCAGATTTAGAGTCTGCTCCCTRTTGGCCGCTCGGGAACCCCACC-3' | (SEQ ID NO:109) |
| 931) | 5'-ACAGGTAATGCTTTTACTGGCCTGCTCCCTTATCGGGAAGCG-3' | (SEQ ID NO:110) |
| 970) | 5'TCGAGCGCC-3' | (SEQ ID NO:111) |
| 971) | 5'-GATCGGCGC-3' | (SEQ ID NO:112) |
| 972) | 5'-CTAGGGCCT-3' | (SEQ ID NO:113) |
| 973) | 5'-CTAGAGGCC-3' | (SEQ ID NO:114) |
| 974) | 5'-CGCCC-3' | (SEQ ID NO:115) |
| 978) | 5'-GATCGGGCGAGCT-3' | (SEQ ID NO:116) |
| AB23) | 5'-CTAGTTACCCGTACGACGTTCCGGACTACGCTTCTTAATAG-3' | (SEQ ID NO:117) |
| AB24) | 5'-AATTCTATTAAGAAGCGTAGTCCGGAACGTCGACGGTAA-3' | (SEQ ID NO:118) |

Polynucleotides 926, 927, 928, AB23, 971, 931, 930 and 929 were kinased by adding 1.0±1 of each polynucleotide (0.1 ug/ul) and 20 units of $T_4$, polynucleotide kinase to a solution containing 70 mM Tris-HCl at pH 7.6, 10 mM $MgCl_2$, 5 mM DTT, 10 mM 2ME, 500 micrograms per ml of BSA. The solution was maintained at 37 C for 30 minutes and the reaction stopped by maintaining the solution at 65 C for 10 minutes.

The required polynucleotides were annealed to form the synthetic DNA sequence shown in FIG. 18A (SEQ ID NO:119). Briefly, the following solutions of polynucleotides were admixed to 1/10 volume of a solution containing 20.0 mM Tris HCl at pH 7.4, 2.0 mM Mg $CL_2$ and 50.0 mM NaCl: 5 ul of separate, 2.5 ug/ml solutions containing the kinased polynucleotides 926, 927, 928, 929, 930 and 930; 4 ul of separate, 2.0 ug/ml solutions containing the unkinased polynucleotide AB24 and the kinased polynucleotide AB23; 2 ul of separate, 1.0 ug/ml solutions containing the kinased polynucleotide 971, and the unkinased polynucleotide 970.

This solution was heated to 70° C. for 5 minutes and allowed to cool to 40° C. over 1.5 hours in a 500 ml beaker of water. During this time period all 10 polynucleotides annealed to form the double stranded synthetic DNA insert shown in FIG. 18A (SEQ ID NO:119). The individual polynucleotides were covalently linked to each other to stabilize the synthetic DNA insert by admixing all of the above reaction (46.6 ul) to a solution containing 50 mM Tris-HCl at pH 7.5, 7 mM $MgCl_2$, 1 mM DDT, 1 mM adenosine triphosphate (ATP) and 10 units of T4 DNA ligase to form a ligation reaction admixture. This admixture was maintained at 37° C. for 1 hour and then the T4 DNA ligase was inactivated by maintaining the solution at 65° C. for 15 minutes. The end polynucleotides were kinased by admixing all of the above ligation reaction admixture reaction, 6 gl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes. The completed synthetic DNA insert (FIG. 18A (SEQ ID NO:119)) was ready for ligation to the $V_H$-Expression vector (FIG. 7) that had been previously digested with the restriction endonucleases Xho I and Eco RI.

The $V_H$-Expression vector (FIG. 7) was digested with the restriction endonucleases Xho I and Eco RI according to the manufacturers recommendations. Briefly, 50 ug the $V_H$-Expression vector (38.5 ul), 225 units of Xho I (Stratagene) and 150 units of Eco RI (Stratagene), were admixed to a universal restriction endonuclease buffer consisting of 50 mM Tris-HCl at pH 7.7, 10 mM $MgCl_2$, 50 mM NaCl and 100 ug/ml BSA to form a digestion admixture. The digestion admixture was maintained at 37 C for 2 hours.

The digestion admixture was then adjusted to pH 8.0 by adding a solution of 1.0 m Tris-HCl at pH 8.0 to a final concentration of 0.1 M. 2.5 units of calf intestine alkaline phosphatase (Stratagene) was added to this solution and the resulting solution maintained at 37 C for 30 minutes. The calf intesine alkaline phosphatase was inactivated by maintaining the solution at 65 C for 10 minutes. The $V_H$-Expression vector DNA was then purified by phenol extraction followed by ethanol precipitation. The restriction endonuclease cleaved $V_H$-Expression vector DNA was then resuspended in 50 ul of a solution containing 10 mM Tris-HCl at pH 8.0 and 1 mM EDTA.

The synthetic DNA insert prepared above was inserted into the restriction endonuclease cleaved $V_H$-Expression vector. Briefly, 1 ug of Xho I and Eco RI cleaved $V_H$-Expression vector, 2 ul of synthetic DNA insert (0.5 ug) and 0.5 ul (4 units) of T4 DNA ligase (Stratagene) was admixed to a solution containing 66 mM Tris-HCl at pH 7.6, 5.0 mM $MgCl_2$, 5.0 mM DTT and 1.0 mM ATP to form a ligation admixture. The ligation admixture was maintained at 37 C for 2 hours. The ligation mixture was then packaged according to the manufacturer's instructions using Gigapack II Gold packing extract available from Stratagene. The packaged ligation mixture was then plated on XL1 blue cells (Stratagene).

Figure 19A:
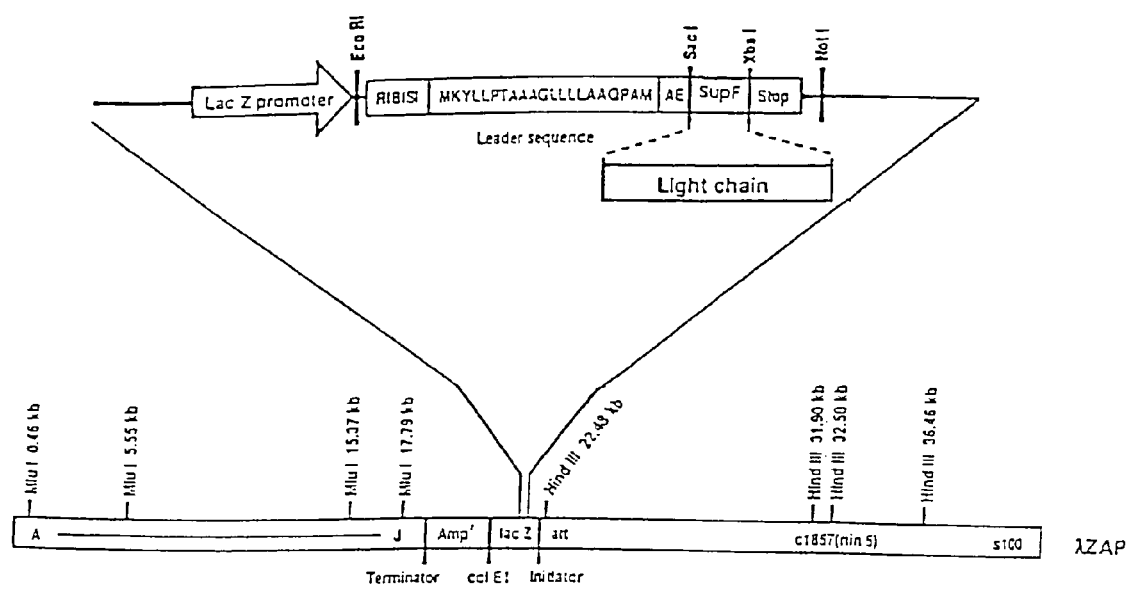

Individual lambda phage plaques were selected for DNA sequencing by selecting individual plaques that hybridized to polynucleotides contained in the synthetic DNA insert according to the method described in *Current Protocols in Molecular Biology*, Ausubel et al., eds., John Wiley and Sons, New York (1987). The selectable $V_H$ expression vector is shown in FIG. 19A.

C. Selectable $V_L$-Expression Vector Construction

To add the ability to select against expression vectors not containing $V_L$-coding DNA homologs, a suppressor tRNA gene was inserted into the $V_L$-Expression vector prepared in Example 11. The selectable $V_L$-Expression vector was prepared by inserting a synthetic DNA sequence containing the suppressor tRNA gene and DNA sequence coding for the decapeptide tag into the $V_L$-Expression vector prepared in Example 11 that had been previously cleaved with the restriction endonucleases Sac I and Xba I.

A synthetic DNA sequence containing the suppressor tRNA gene and polynucleotide sequence coding for decapeptide tag was constructed by designing single stranded polynucleotide segments of 20–40 bases that would hybridize to each other and form the double stranded synthetic DNA sequence shown in FIG. 18B (SEQ ID NO:120). The individual single-stranded polynucleotides are shown in Table 5 (SEQ ID NOS:103–118).

Polynucleotides 926, 927, 928, 929, 930, 972 and 975, were kinased by adding 1.0 gl of each polynucleotide (0.1 ug/ul) and 20 units of $T_4$ polynucleotide kinase to a solution containing 70 mM Tris-HCl at pH 7.6, 10 MM $MgCl_2$, 5 MM DTT, 10 mM 2ME, 100 micrograms per ml of BSA. The solution was maintained at 37 C for 30 minutes and the reaction stopped by maintaining the solution at 65 C for 10 minutes.

The required polynucleotides were annealed to form the synthetic DNA sequence shown in FIG. 18B (SEQ ID NO:120). Briefly, the following solutions of polynucleotides were admixed to 1/10 volume of a solution containing 20.0 mM Tris HCl at pH 7.4, 2.0 mM $MgCL_2$ and 50.0 mM NaCl: 5 ul of separate, 2.5 ug/ml solutions containing the kinased polynucleotides 926, 927, 928, 929, 930 and 931; 2 ul of separate, 2.0 ug/ml solutions containing the unkinased polynucleotides 974 and 973, acid the kinased polynucleotides 972 and 975.

This solution was heated to 70° C. for 5 minutes and allowed to cool to 40 C over 1.5 hours in a 500 ml beaker of water. During this time period all 10 polynucleotides annealed to form the double stranded synthetic DNA insert shown in FIG. 18B (SEQ ID NO:120). The individual polynucleotides were covalently linked to each other to stabilize the synthetic DNA insert by admixing all of the above reaction (42.2 ul) to a solution containing 50 mM Tris-HCl at pH 7.5, 7 mM $MgCl_2$, 1 mM DDT, 1 mM adenosine triphosphate (ATP) and 10 units of T4 DNA ligase to form a ligation reaction admixture. This admixture was maintained at 37° C. for 1 hour and then the T4 DNA ligase was inactivated by maintaining the solution at 65° C. for 15 minutes. The end polynucleotides were kinased by admixing all of the above ligation reaction admixture reaction, 6 μl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes, the completed synthetic DNA insert (FIG. 18B (SEQ ID NO:120)) was ready for ligation to the Expression vector (FIG. 9) that had been previously digested with the restriction endonucleases Sac I and Xba I.

The $V_L$-Expression vector (FIG. 9) was digested with the restriction endonucleases Sac I and Xba I, according to the manufacturer's recommendations. Briefly, 5.0 ug the $V_L$-Expression vector (30.5 ul), 50 units of Sac I (Stratagene) and 50 units of Xba I (Stratagene), were admixed to a universal restriction endonuclease buffer consisting of 10 mM Tris-HCl at pH 7.7, 10 mM $MgCL_2$, 100 mM NaCl and 100 ug/ml BSA to form a digestion admixture. The digestion admixture was maintained at 37 C for 2 hours.

The digestion admixture was then adjusted to pH 8.0 by adding a solution of 1.0 m Tris-HCl at pH 8.0 to a final concentration of 0.1M. 2.5 units of calf intestine alkaline phosphatase (Stratagene) was added to this solution and the resulting solution maintained at 37 C for 30 minutes. The calf intestine alkaline phosphatase was inactivated by maintaining the solution at 65 C for 10 minutes. The $V_L$-Expression vector DNA was then purified by phenol extraction followed by ethanol precipitation. The restriction endonuclease cleaved $V_L$-Expression vector DNA was the resuspended in 50 ul of a solution containing 10 mM Tris-HCl at pH 8.0 and 1 mM EDTA.

The synthetic DNA insert prepared above was inserted into the restriction endonuclease cleaved $V_L$-Expression vector. Briefly, 1 ug of Sac I and Xba I cleaved $V_L$-Expression vector, 2 ul of synthetic DNA insert (0.5 ug) and 0.5 ul (4 units) of T4 DNA ligase (Stratagene) was admixed to a solution containing 66 mM Tris-HCl at pH 7.6, 5.0 MM $MgCl_2$, 5.0 mM DTT and 1.0 mM ATP to form a ligation admixture. The ligation admixture was maintained at 37° C. for 2 hours. The ligation mixture was packaged according to the manufacturer's instructions using Gigapack II Gold packing extract available from Stratagene. The packaged ligation mixture was plated on XL1 blue cells (Stratagene).

Figure 19B:
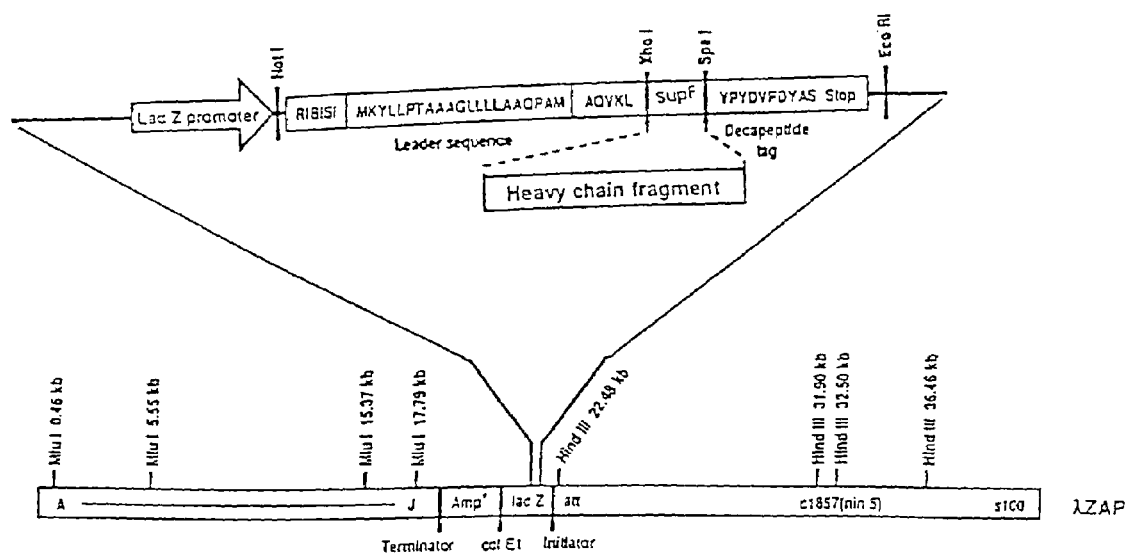

Individual lambda phage plaques were selected for DNA sequencing by screening for plaques that hybridized to polynucleotides contained in the synthetic DNA insert according to the methods described in *Molecular Cloning: A Laboratory Manual*, Maniatis et al., eds., Cold Spring Harbor, N.Y. (1989). The selectable $V_L$ expression vector is shown in FIG. 19B.

D. Construction of a Selectable $V_L$ and $V_H$-Expression Vector

The $V_H$-Expression vector prepared in Example 17B is modified so that it does not contain any Xho I or Spe I restriction endonuclease sites. This modification of this vector is accomplished using a set of polynucleotides and methods similar to the methods described in Example 17B.

The $V_L$-Expression vector prepared in Example 17C is modified so that it does not contain any Sac I or Xba I restriction endonuclease sites. This modification of the $V_L$-Expression vector is accomplished using a set of polynucleotides and methods well known in the art and similar to the methods described in Example 17C. The modified $V_L$-Expression vector and the modified $V_H$-Expression vector are combined to produce a selectable $V_L$ and $V_H$ Expression vector. Briefly, the modified $V_H$-Expression vector is digested with the restriction endonucleases Eco RI and Hind III using the conditions recommended by the enzyme manufacturer and is digested with the restriction endonucleases Eco RI and Mlu I. The restriction endonuclease cleaved $V_H$ and $V_L$ Expression vectors are the ligated together using standard techniques to form the selectable $V_H$ and $V_L$ Expression vector shown in FIG. 20.

The $V_H$ and $V_L$ Expression vector contains 2 suppressors tRNA genes, one is replaced by the $V_H$ DNA homolog and the other is replaced by the $V_L$ DNA homolog. Therefore, when the vector contains both a $V_H$ and a $V_L$ DPTA homolog, the vector does not contain a suppressor tRNA gene allowing the $V_H$ and $V_L$ containing vector to produce phage plaques under the appropriate selection conditions.

E. Inserting DNA Homolocrs into the Selectable DNA Expression Vectors $V_H$ coding and/or $V_L$ coding DNA homologs prepared in Example 5 are inserted into the $V_H$+$V_L$ expression vector, the $V_H$ expression vector, or the $V_L$ expression vector using the provided restriction endonuclease sites. The $V_H$ coding DNA homologs are typically inserted into the provided Xho I and Spe I restriction endonuclease sites (FIG. 20) using standard procedures. The $V_L$ coding DNA homologs are typically inserted into the provided restriction endonuclease sites (FIG. 20). Therefore, depending on the particular expression vector selected, the methods described herein produce an expression vector containing a $V_H$ coding DNA homolog alone, a $V_L$ coding DNA homolog alone, or a $V_H$ and a $V_L$ DNA homolog.

The $V_H$ coding DNA homologs may be inserted into the expression vector first, followed by the $V_L$ DNA homologs. Alternatively, the $V_L$ coding homologs may be inserted first followed by the $V_H$ coding homologs. Either insertion order allows the random recombination of a library of $V_H$ coding DNA homologs with a library $V_L$ coding DNA homologs. After the $V_H$ homologs have been inserted into the $V_H$+$V_L$ expression vector, the expression vector can be grown to produce more of the $V_H$ containing expression vector. The $V_L$ coding DNA homologs can then be inserted into the $V_H$+$V_L$ expression vector. Any of these procedures will allow the production of a large combinatorial library.

F. Selection of $V_H$ and/or $V_L$ DNA Homolog Containing Phage

A strong selection system is employed in order to reduce the number of expression vectors present library that do not contain $V_H$ and/or $V_L$ DNA homologs. The selection system combines the dominant Lambda S gene mutation with the suppressor tRNA that is present in $V_H$ and/or $V_L$ expression vectors. When the suppressor tPITA is in the final. The present in the expression vector, the mutant Lambda S protein is produced preventing the lysis of the infected cell and thereby preventing the formation of a phage plaque. When a DNA homolog replaces the suppressor tRNA, the expression vector can produce a phage plaque. In order to detect a $V_H$ and/or $V_L$ the $V_H$ and/or $V_L$ expression vector must produce a phage plaque because without plaque production there is not enough $V_H$+$V_L$ expressed to detect. Therefore, phages not containing a $V_H$ and/or $V_L$ will not be detected.

To accomplish this selection, appropriate host bacterial cells containing the mutant S gene plasmid produced in Example 17A are infected with the desired expression vector library. Only the expression vectors without suppressor tRNA genes, the expression vectors containing DNA homologs, produce phage plaques.

18. Generation of a Large Combinatorial Library of the Immunoglobulin Repertoire in Phage Vectors suitable for expression of $V_H$, $V_L$, $F_V$ and Fab sequences are diagrammed in FIGS. 7 and 9. As previously discussed, the vectors were constructed by modification of Lambda Zap by inserting synthetic oligonucleotides into the multiple cloning site. The vectors were designed to be antisymmetric with respect the Not I and EcoR I restriction sites which flank the cloning and expression sequences. As described below, antisymmetry in the placement of restriction sites in a linear vector like bacteriophage is the essential feature of the system which allows a library expressing light chains to be combined with one expressing heavy chains to construct combinatorial Fab expression libraries. Lambda Zap II $V_L$II (FIG. 9) is designed to serve as a cloning vector for light chain fragments and Lambda Zap II $V_H$ (FIG. 7) is designed to serve as a cloning vector for heavy chain sequences in the initial step of library construction. These vectors are engineered to efficiently clone the products of PCR amplification with specific restriction sites incorporated at each end.

A. PCR Amplification of Antibody Fragments

The PCR amplification of mRNA isolated from spleen cells with oligonucleotides which incorporate restriction sites into the ends of the amplified product can be used to clone and express heavy chain sequences including Fd and kappa chain sequences. The oligonucleotide primers used for these amplifications are presented in Tables 1 and 2. The primers are analogous to those which have been successfully used in Example 5 for amplification of $V_H$ sequences. The set of 5' primers for heavy chain amplification were identical to those previously used to amplify $V_H$ and those for light chain amplification were chosen on similar principles, Sastry et al., *Proc. Natl. Acad. Sci. USA*, 8G: 5728 (1989) and Orland et al., *Proc Natl. Acad. Sci. USA*, 8G:3833 (1989). The unique 3' primers of heavy (IgGi) and light (k) chain sequences were chosen to include the cysteines involved in heavy-light chain disulfide bond formation. At this stage no primer was constructed to amplify lambda light chains since they constitute only a small fraction of murine antibodies. In addition, $F_v$ fragments have been constructed using a 3' primer which is complementary to the mRNA in the J (joining) region (amino acid 128) and a set of unique 5' primers which are complementary to the first strand cDNA in the conserved IT-terminal region of the processed protein. Restriction endonuclease recognition sequences are incorporated into the primers to allow for the cloning of the amplified fragment into a lambda phage vector iii a predetermined reading frame for expression.

B. Library Construction

The construction of a combinatorial library was accomplished in two steps. In the first step, separate heavy and light chain libraries were constructed in Lambda Zap II $V_H$ and Lambda Zap II $V_L$ II respectively. In the second step, these two libraries were combined at the antisymmetric EcoR1 sites present in each vector. This resulted in a library of clones each of which potentially co-expresses a heavy and a light chain. The actual combinations are random and do not necessarily reflect the combinations present in the B-cell population in the parent animal. Lambda Zap II $V_H$ expression vector has been used to create a library of heavy chain sequences from DNA obtained by PCR amplification of mRNA isolated from the spleen of a 129 $G_{IX}$+ mouse previously immunized with p-nitrophenyl phosphonamidate (NPN) antigen 1 according to formula I (FIG. 13) conjugated to keyhole limpet hemocyanin (KLH).

The NPN-KLH conjugate was prepared by admixture of 250 ul of a solution containing 2.5 mg of NPN according to formula 1 (FIG. 13) in dimethylformamide with 750 ul of a solution containing 2 mg of KLH in 0.01 M sodium phosphate buffer (pH 7.2). The two solutions were admixed by slow addition of the NPN solution to the KLH solution while the KLH solution was being agitated by a rotating stirring bar. Thereafter the admixture was maintained at 4° for 1 hour with the same agitation to allow conjugation to proceed. The conjugated NPN-KLH was isolated from the nonconjugated NPN and KLH by gel filtration through Sephadex G-25. The isolated NPN-KLH conjugate was used in mouse immunizations as described in Example 2.

The spleen mRNA resulting from the above immunizations was isolated and used to create a primary library of $V_H$ gene sequences using the Lambda Zap II $V_H$ expression vector. The primary library contains $1.3 \times 10^5$ pfu and has been screened for the expression of the decapeptide tag to determine the percentage of clones expressing Fd sequences. The sequence for this peptide is only in frame for expression following the cloning of a Fd (or $V_H$) fragment into the vector. At least 80% of the clones in the library express Fd fragments based on immuno-detection of the decapeptide tag.

The light chain library was constructed in the same way as the heavy chain and shown to contain $2.5 \times 10^6$ members. Plaque screening, using an anti-kappa chain antibody, indicated that 60% of the library contained expressed light chain inserts. This relatively small percentage of inserts probably resulted from incomplete dephosphorylation of vector after cleavage with Sac I and Xba I.

Once obtained, the two libraries were used to construct a combinatorial library by crossing them at the EcoR I site. To accomplish the cross, DNA was first purified from each library. The light chain library was cleaved with MluI restriction endonuclease, the resulting 5' ends dephosphorylated and the product digested with EcoR I. This process cleaved the left arm of the vector into several pieces but the right arm containing the light chain sequences, remained intact. In a parallel fashion, the DNA of heavy chain library was cleaved with HindIII, dephosphorylated and cleaved with EcoR I, destroying the right arm but leaving the left arm containing the heavy chain sequences intact. The DNA's so prepared were then combined and ligated. After ligation only clones which resulted from combination of a right arm of light chain-containing clones and a left arm of heavy chain-containing clones reconstituted a viable phage. After ligation and packaging, $2.5 \times 10^7$ clones were obtained. This is the combinatorial Fab expression library that was screened to identify clones having affinity for NPN. To determine the frequency the phage clones which co-express the light and heavy chain fragments, duplicate lifts of the light chain, heavy chain and combinatorial libraries were screened as above for light and heavy chain expression. In this study of approximately 500 recombinant phage approximately 60% co-expressed light and heavy chain proteins.

C. Antigen Binding

All three libraries, the light chain, the heavy chain and Fab were screened to determine if they contained recombinant phage that expressed antibody fragments binding NPN. In a typical procedure 30,000 phage were plated and duplicate lifts with nitrocellulose screened for binding to NPN coupled to 125I labeled BSA (FIG. 15). Duplicate screens of 80,000 recombinant phage from the light chain library and a similar number from the heavy chain library did not identify any clones which bound the antigen. In contrast, the screen of a similar number of clones from the Fab expression library identified many phage plaques that bound NPN (FIG. 15). This observation indicates that under conditions where many heavy chains in combination with light chains bind to antigen the same heavy or light chains alone do not. Therefore, in the case of NPN, it is believed that there are many heavy and light chains that only bind antigen when they are combined with specific light and heavy chains respectively.

To assess the ability to screen large numbers of clones and obtain a more quantitative estimate of the frequency of antigen binding clones in the combinatorial library, one million phage plaques were screened and approximately 100 clones which bound to antigen were identified. For six clones which were believed to bind NPN, a region of the plate containing the positive and approximately 20 surrounding bacteriophage plaques was "cored", replated, and screened with duplicate lifts (FIG. 15). As expected, approximately one in twenty of the phage specifically bind to antigen. "Cores" of regions of the plated phage believed to be negative did not give positives on replating.

To determine the specificity of the antigen-antibody interaction, antigen binding was competed with free unlabeled antigen as shown in FIG. 16. Competition studies showed that individual clones could be distinguished on the basis of antigen affinity. The concentration of free haptens required for complete inhibition of binding varied between 10–100× $10^9$ M suggesting that the expressed Fab fragments had binding constants in the nanomolar range.

D. Composition of the Clones and Their Expressed Products

In preparation for characterization of the protein products able to bind NPN as described in Example 18C, a plasmid containing the heavy and light chain genes was excised from the appropriate "cored" bacteriophage plaque using M13 mp8 helper phage. Mapping of the excised plasmid demonstrated a restriction pattern consistent with incorporation of heavy and light chain sequences. The protein products of one of the clones was analyzed by ELISA and Western blotting to establish the composition of the NPN binding protein. A bacterial supernate following IPTG induction was concentrated and subjected to gel filtration. Fractions in the molecular weight range 40–60 kD were pooled, concentrated and subjected to a further gel filtration separation. As illustrated in FIG. 17, ELISA analysis of the eluting fractions demonstrated that NPN binding was associated with a protein of molecular weight about 50 kD which immunological detection showed contained both heavy and light chains. A Western blot (not shown) of a concentrated bacterial supernate preparation under non-reducing conditions was developed with anti-decapeptide antibody. This revealed a protein band of molecular weight of 50 kD. Taken together these results are consistent with NPN binding being a function of Fab fragments in which heavy and light chains are covalently linked.

E. Comparison of the Properties of the In Vivo Repertoire Versus the Phage Combinatorial Library In this example a relatively restricted library was prepared because only a limited number of primers were used for PCR amplification of Fd sequences. The library is expected to contain only clones expressing kappa/gammal sequences. However, this is not an inherent limitation of the method since additional primers can be added to amplify any antibody class or subclass. Despite this restriction we were able to isolate a large number of antigen binding clones.

A central issue arising from this work is how a phage library prepared as described herein compares with the in vivo antibody repertoire in terms of size, characteristics of diversity, and ease of access.

The size of the mammalian antibody repertoire is difficult to judge but a figure of the order of $10^6$–$10^8$ different antigen specificities is often quoted. With some of the reservations discussed below, a phage library of this size or larger can readily be constructed by a modification of the current method. In fact once an initial combinatorial library has been constructed, heavy and light chains can be shuffled to obtain libraries of exceptionally large numbers. In principle, the diversity characteristics of the naive (unimmunized) in vivo repertoire and corresponding phage library are expected to be similar in that both involve a random combination of heavy and light chains. However, different factors will act to restrict the diversity expressed by an in vivo repertoire and phage library. For example a physiological modification such as tolerance will restrict the expression of certain antigenic specificities from the in vivo repertoire but these specificities may still appear in the phage library. On the other hand, bias in the cloning process may introduce restrictions into the diversity of the phage library. For example the representation of mRNA for sequences expressed by stimulated B-cells can be expected to predominate over those of unstimulated cells because of higher levels of expression.

Different source tissues (e.g., peripheral blood, bone marrow or regional lymph nodes) and different PCR primers (e.g., ones expected to amplify different antibody classes) may result in libraries with different diversity characteristics.

Another difference between in vivo repertoire and phage library is that antibodies isolated from the former may have benefited from affinity maturation due to somatic mutations after combination of heavy and light chains whereas the latter randomly combines the matured heavy and light chains. Given a large enough phage library derived from a particular in vivo repertoire, the original matured heavy and light chains will be recombined. However, since one of the potential benefits of this new technology is to obviate the need for immunization by the generation of a single highly diverse "generic" phage library, it would be useful to have methods to optimize sequences to compensate for the absence of somatic mutation and clonal selection. Three procedures are made readily available through the methods of the present invention. First, saturation mutagenesis may be performed on the CDR's and the resulting Fabs can be assayed for increased function. Second, a heavy or a light chain of a clone which binds antigen can be recombined with the entire light or heavy chain libraries respectively in a procedure identical to the one used to construct the combinatorial library. Third, iterative cycles of the two above procedures can be performed to further optimize the affinity or catalytic properties of the immunoglobulin. It should be noted that the latter two procedures are not permitted in B-cell clonal selection which suggests that the methods described here may actually increase the ability to identify optimal sequences.

Access is the third area where it is of interest to compare the in vivo antibody repertoire and phage library. In practical terms the phage library is much easier to access. The screening methods allow one to survey at least 50,000 clones per plate so that $10^6$ antibodies can be readily examined in a day. This factor alone should encourage the replacement of hybridoma technology with the methods described here. The most powerful screening methods utilize selection which may be accomplished by incorporating selectable markers into the antigen such as leaving groups necessary for replication of auxotrophic bacterial strains or toxic substituents susceptible to catalytic inactivation. There are also further advantages related to the fact that the in vivo antibody repertoire can only be accessed via immunization which is a selection on the basis of binding affinity. The phage library is not similarly restricted. For example, the only general method to identify antibodies with catalytic properties has been by pre-selection on the basis of affinity of the antibody to a transition state analogue. No such restrictions apply to the in vitro library where catalysis can, in principle, be assayed directly. The ability to directly assay large numbers of antibodies for function may allow selection for catalysts in reactions where a mechanism is not well defined or synthesis of the transition state analog is difficult. Assaying for catalysis directly eliminates the bias of the screening procedure for reaction mechanisms pejorative to a synthetic analog and therefore simultaneous exploration of multiple reaction pathways for a given chemical transformation are possible.

The methods disclosed herein describe generation of Fab fragments which are clearly different in a number of important respects from intact (whole) antibodies. There is undoubtedly a loss of affinity in having monovalent Fab antigen binders but this can be compensated by selection of suitably tight binders. For a number of applications such as diagnostics and biosensors it may be preferable to have monovalent Fab fragments. For applications requiring Fc effector functions, the technology already exists for extending the heavy chain gene and expressing the glycosylated whole antibody in mammalian cells.

The ideas presented here address the bottle neck in the identification and evaluation of antibodies. It is now possible to construct and screen at least three orders of magnitude more clones with mono-specificity than previously possible. The potential applications of the method should span basic research and applied sciences. The foregoing is intended as illustrative of the present invention but not limiting. Numerous variations and modifications can be effected without departing from the true spirit and scope of the invention.

What is claimed is:

1. A degenerate 5' primer that hybridizes to a region of a $V_H$ immunoglobulin domain, wherein the primer consists of 15 to 25 nucleotides and is substantially complementary to a nucleotide sequence conserved in any one of the leader or first framework regions.

2. The primer of claim 1, wherein the region is the first framework of the variable region.

3. The primer of claim 1, wherein the primer consists of the sequence of 5'-AGGT(C/G)(C/A)A(G/A)CT(G/T)CTC-GAGTC(T/A)GG-3'.

4. The primer of claim 1, wherein the primer comprises a nucleotide sequence defining an endonuclease recognition site.

5. A pair of primers suitable for amplifying a $V_H$-coding region, wherein the first primer is a primer according to claim 1, and wherein the second primer hybridizes with a nucleotide sequence conserved at the 5' end of the non-coding strand.

* * * * *